(12) United States Patent
Zafiris

(10) Patent No.: US 12,029,874 B2
(45) Date of Patent: Jul. 9, 2024

(54) DIALYSIS PATIENT CONNECTOR AND METHOD FOR PRIMING

(71) Applicants: BAXTER INTERNATIONAL INC., Deerfield, IL (US); BAXTER HEALTHCARE SA, Glattpark (CH)

(72) Inventor: John Zafiris, Hawthorn Woods, IL (US)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 548 days.

(21) Appl. No.: 17/159,539

(22) Filed: Jan. 27, 2021

(65) Prior Publication Data

US 2021/0228856 A1 Jul. 29, 2021

Related U.S. Application Data

(60) Provisional application No. 62/967,217, filed on Jan. 29, 2020.

(51) Int. Cl.
*A61M 39/02* (2006.01)
*A61M 1/14* (2006.01)
(Continued)

(52) U.S. Cl.
CPC ........ *A61M 39/0247* (2013.01); *A61M 1/153* (2022.05); *A61M 1/154* (2022.05);
(Continued)

(58) Field of Classification Search
CPC .............. A61M 39/0247; A61M 39/24; A61M 2039/027; A61M 2039/0273; A61M 2205/7527
See application file for complete search history.

(56) References Cited

U.S. PATENT DOCUMENTS 6,758,971 B1 7/2004 Haight
2003/0018288 A1* 1/2003 Ludt ................... A61M 1/3646
134/22.12

(Continued)

FOREIGN PATENT DOCUMENTS

EP 2252345 B1 9/2016

OTHER PUBLICATIONS

International Search Report for PCT/US2021/015235 dated May 10, 2021—5 pages.
(Continued)

*Primary Examiner* — Dung T Ulsh
(74) *Attorney, Agent, or Firm* — K&L Gates LLP

(57) ABSTRACT

A patient connector for dialysis is disclosed. In an example, a patient connector includes a housing including an inlet and an outlet and defining at least one aperture. The patient connector also includes a seal initially blocking the outlet and a hydrophobic filter covering the at least one aperture of the housing. The patient connector further includes a check valve positioned and arranged to prevent air from being vented from the housing via the at least one aperture and through the hydrophobic filter when the housing is under atmospheric pressure or negative pressure. The check valve is configured to allow air to be vented from the housing via the at least one aperture and through the hydrophobic filter when the housing is under positive pressure.

6 Claims, 26 Drawing Sheets

(51) Int. Cl.
*A61M 1/16* (2006.01)
*A61M 1/28* (2006.01)
*A61M 39/24* (2006.01)
*A61M 60/113* (2021.01)
*A61M 60/279* (2021.01)
*A61M 60/37* (2021.01)

(52) U.S. Cl.
CPC .......... *A61M 1/155* (2022.05); *A61M 1/1563* (2022.05); *A61M 1/1565* (2022.05); *A61M 1/159* (2022.05); *A61M 1/166* (2014.02); *A61M 1/167* (2014.02); *A61M 1/285* (2013.01); *A61M 1/288* (2014.02); *A61M 39/24* (2013.01); *A61M 60/113* (2021.01); *A61M 60/279* (2021.01); *A61M 60/37* (2021.01); *A61M 1/1524* (2022.05); *A61M 2039/027* (2013.01); *A61M 2039/0273* (2013.01); *A61M 2205/127* (2013.01); *A61M 2205/3331* (2013.01); *A61M 2205/3368* (2013.01); *A61M 2205/3653* (2013.01); *A61M 2205/50* (2013.01); *A61M 2205/7527* (2013.01)

(56) References Cited

U.S. PATENT DOCUMENTS

| | | |
|---|---|---|
| 2006/0195064 A1 | 8/2006 | Plahey et al. |
| 2017/0209644 A1* | 7/2017 | Browka ................ A61M 5/165 |
| 2019/0060544 A1 | 2/2019 | Childers |
| 2019/0316948 A1 | 10/2019 | Karol et al. |
| 2021/0331123 A1 | 10/2021 | Fischer et al. |

OTHER PUBLICATIONS

Written Opinion for PCT/US2021/015235 dated May 10, 2021—410 pages.
European Office Action, Application No. 21707491.3-1113 dated Sep. 6, 2022—3 pages.
European Office Action, Application No. 21706786.7-1113 dated Sep. 6, 2022—3 pages.
International Preliminary Report on Patentability dated Jul. 28, 2022—11 pages.
International Preliminary Report on Patentability for PCT/US2021/015235 dated Apr. 5, 2022.

* cited by examiner

US 12,029,874 B2

DIALYSIS PATIENT CONNECTOR AND METHOD FOR PRIMING

PRIORITY CLAIM

This application claims priority to and the benefit of U.S. Provisional Patent Application Ser. No. 62/967,217, filed on Jan. 29, 2020, the entire disclosure of which is hereby incorporated by reference.

TECHNICAL FIELD

The present disclosure relates generally to medical fluid therapies and more particularly to medical fluid therapy systems that are capable of producing medical fluid at the point of use.

BACKGROUND

Certain medical fluid therapies employ presterilized bags of treatment fluid. For example, peritoneal dialysis is typically performed in a patient's home. There are different types of peritoneal dialysis, including continuous ambulatory peritoneal dialysis ("CAPD") and automated peritoneal dialysis ("APD"). CAPD is a manual treatment in which the patient typically drains used dialysis fluid from the patient's peritoneal cavity and then causes fresh dialysis fluid to refill the peritoneal cavity. The fresh dialysis fluid is left to dwell for a period of time to remove waste, toxins and excess water into the dialysis fluid, after which the used fluid is drained to begin a new cycle.

APD is performed by a machine, which is sometimes referred to as a cycler because it performs the same cycles described above for CAPD. APD is typically performed at night, while the patient sleeps, and while the patient's indwelling peritoneal catheter is connected to a patient line extending to the APD machine. As with CAPD, if the patient at the start of treatment is full with used peritoneal dialysis ("PD") fluid, the APD machine initially drains the used fluid to a dedicated drain bag or to a house drain. Next, the APD machine fills the patient with fresh peritoneal dialysis fluid, which is left to dwell for a period of time to remove waste, toxins and excess water into the dialysis fluid. The APD machine repeats the above cycle until a prescribed amount of fresh peritoneal dialysis fluid has been delivered to the patient.

CAPD and APD typically use multiple bags per treatment, for example, two to four bags. CAPD may be performed multiple times during the day, while nighttime APD may be accompanied by a midday manual exchange. The number of bags per day multiplied by the number of days between treatment fluid deliveries results in the patient having to store boxes upon boxes of solution in their home. In many instances, a wall of a room is dedicated to storing PD solution and supplies.

Another way that medical fluid therapy fluids or solutions are prepared is to do so at the place of treatment, which is sometimes termed "online generation". Hemodialysis ("HD"), which cleans the patient's blood as opposed to using the patient's peritoneal cavity, typically makes HD dialysis fluid online. To do so, water first has to be purified to a level that is safe for treatment. Once HD concentrates have been added to the purified water, the resulting HD dialysis fluid is passed through a dialyzer, which also receives the patient's blood, to exchange waste, toxins and excess patient water across the dialyzer membranes and into the HD dialysis fluid. HD treatments are most often performed in a dialysis center, in which a large batch of highly purified water may be made for multiple HD dialysis machines located within the center.

In the center, noisy water purification equipment, such as pumps and reverse osmosis ("RO") units, can be located in a different room or otherwise away from the patient area. Also, because water purification may be centralized for multiple machines, equipment cost is reduced. Attempts have been made to make water purification units for home therapy systems, such as home dialysis systems. Some of the attempts have included a multitude of different purification technologies, such as carbon pretreatment packs, RO filtration, electrodeionization ("EDI"), resin beds, ultraviolet ("UV") radiation, ultrafiltration and others. While the combination of such technologies may yield ultrapure water, the resulting systems are complicated and expensive.

A need exists accordingly for an improved dialysis system that reduces the amount of space and disposable waste associated with premade dialysis fluid and that improves the current issues associated with water purification devices and online dialysis fluid generation.

SUMMARY

The devices, systems and methods of the present disclosure attempt to remedy the above-described problems. In one embodiment, the system provides a non-invasive measurement of volume and flow, which allows for any type of dialysis fluid pump to be used. From a simplicity of disposable standpoint, the most desirable pump is a peristaltic pump, which simply requires a pumping tube to operate with a peristaltic pump actuator. Peristaltic pumps are known to be less accurate than other types of fluid pumps, such as membrane pumps, and to become less accurate over time as the peristaltic pump tubing degrades. The present system and method provide a rigid, vertically disposed clamshell holder that accepts a flexible, vertically disposed and sterilized container or bag for receiving fresh dialysis fluid, used dialysis fluid, saline, purified water and concentrates for mixing dialysis fluid, or other medical fluid.

As whichever fluid fills the vertically disposed bag, the bag where the fluid is located conforms exactly (or near exactly) to the shape of the vertically disposed clamshell holder. The filling fluid also increases pressure within the sterilized bag. The control unit uses a relationship between pressure and head height to calculate fluid volume. With all other dimensions of the vertically disposed clamshell holder known except for the height of fluid within the bag, solving for the head height based on a measured pressure allows the volume of fluid in the bag at a given time to be calculated. Calculating a difference between head heights and dividing the difference by a time between pressure measurements allows a flowrate to be determined.

In an embodiment, one or more pressure sensors are located at the bottom of the clamshell holder, e.g., is fixed within an opening or mounting structure formed in the lower portion of a panel of the clamshell holder. The pressure sensor may include a pressure pouch that is mounted to or into the panel of the clamshell holder, wherein the pressure pouch makes contact with the vertically disposed container or bag. The pressure pouch holds air or other pressure transition medium that transfers the pressure due to medical fluid within the vertically disposed bag to a pressure transducer, such as a load cell, strain gauge, and/or compensated microelectromechanical systems ("MEMS") pressure sensor. The pressure transducer outputs a signal indicative of the pressure and thus the head height of medical fluid within the bag to a microprocessor, which determines head height, multiplies the head height by the cross-sectional area of the clamshell holder to determine volume and divides the volume over a time delta to determine flowrate.

In one embodiment, the system is configured not to completely fill the vertically disposed bag so that the bag does not apply pressure to the medical fluid located therein. Also, the top of the bag is not constrained by the clamshell holder so as not to pressurize the bag. Additionally, the bag and clamshell holder overlap so that the liquid filled cross-sectional area is defined by the known dimensions of the clamshell holder as opposed to the welds or seems of the container or bag.

It is contemplated to install one or more liquid level sensors in or on one of the panels of the rigid clamshell holder to maintain a baseline level of medical fluid within the flexible bag. The baseline level of fluid serves multiple purposes. First, the bottom of the clamshell holder and thus the disinfected bag may be angled, rounded or otherwise changing in cross-section to help direct fluid to an inlet/outlet and so that the bag does not have to be formed with a flat bottom. The change in cross-section may cause the bag to not be perfectly aligned with the clamshell holder. Also, the contacting of the one or more pressure sensor with bottom of the bag may cause misalignment between the bag and the clamshell holder. In an embodiment, the liquid below baseline is not taken into account in the volume or baseline determination, such that each of the discrepancies just described existing below the baseline level may be discarded.

The liquid level sensor may be, for example, a non-invasive capacitive sensor that senses the level of medical fluid within the flexible container or bag. The sensor outputs, for example, upon a patient fill or upon an effluent drain when the liquid level falls to the sensor level, such that the fill or drain may be discontinued until additional fresh or used dialysis fluid is introduced into the flexible bag. The establishment of a baseline level via sensor also ensures that a fill of fresh or used dialysis fluid into the flexible bag is commenced with the liquid level at or above the baseline level. In an embodiment, two or more level sensors are provided so that one or more upper warning level may be detected prior to reaching a level below which the current cycle needs to be interrupted. In other embodiments, the level of the medical fluid may instead be determined by measuring a water column head pressure.

In an embodiment a delivery tube extends out of the bottom of the sterilized flexible bag. The delivery tube allows the different medical fluids to flow into and out of the bag. In an embodiment, the delivery tube is placed in selective communication with a pump, such as a peristaltic pump, which pumps medical fluid to or from flexible bag, e.g., through one or more valve. In an alternative embodiment, a low cost gravity fed system is provided that does not use a pump, but instead, under computerized valve control, allows fresh fluid to flow from a fresh fluid clamshell holder and flexible bag to the patient for treatment, and used fluid to flow from the patient, under computerized valve control, to a used fluid clamshell holder and flexible bag. The fresh and used fluid clamshell holders and flexible bags operate just as described above, except that they are one-way with fluid only flowing out or into the containers or bags. The fresh fluid clamshell and flexible bag allow monitoring of volume and flowrate of fresh dialysis fluid to the patient. The used fluid clamshell holder and flexible bag allow monitoring of volume and flowrate of used dialysis fluid removed from the patient. The difference between the two is the patient's ultrafiltration ("UF") removal.

In an embodiment, an inline medical fluid heater is located between the pump and the patient to heat the dialysis fluid to patient temperature, e.g., 37° C., prior to delivery to the patient. The inline heater may be an inductive heater in which the disposable component of the inductive heater is, like the pump, a single tube or a tube that is folded or provided with a fitting such that the tube reverses direction 180 degrees. The tube, or each leg of the dual tube, is provided with a susceptor, which may be any medically safe material having the the ability to absorb electromagnetic energy and convert the energy to heat. In an embodiment, the susceptor is made of a medically safe material that exhibits properties of an efficient susceptor, such as 400 series stainless steel, 18-0 magnetic stainless steel, titanium, and combinations and alloys thereof. The susceptor may have a smooth contour to limit its effect on pressure drop in the medical fluid, a changing contour, e.g., mesh or brillo pad, to increase surface area contact with the medical fluid, or a combination of both.

The tubes including the susceptors are fitted within an inductive coil, which may be a conductive copper coil. The copper coil is provided as part of the dialysis machine and is covered by a plastic machine panel (or other material that is not heated by the energized coil) so that a user cannot accidently touch the coil. The inductive coil is connected electrically to power electronics, such as a resonant circuit and driver electronics. The driver electronics are placed under the control of a computerized control unit, which controls the driver electronics to cause power to be supplied to the driver electronics and the induction coil when needed, e.g., when fresh dialysis fluid is flowing to the patient and when feedback from one or more dialysis fluid temperature sensor indicates to the control unit that fluid heating is needed.

In an embodiment, an upstream temperature sensor is housed with the machine and is located so as to sense the temperature of cool dialysis fluid upstream of the one or more susceptor. A downstream temperature sensor is housed with the machine and is located so as to sense the temperature of heated dialysis fluid downstream of the one or more susceptors and heading to the patient. The temperature sensors may be non-contact (e.g., thermopile) sensors, so that there is no invasive or direct fluid contact. The control unit may use the temperature sensor feedback and control power to the resonant circuit and inductive coil using on/off control, proportional-integral-derivative ("PID") control, fuzzy logic control and combinations thereof. In an embodiment, the power supplied to the power electronics is around one kilowatt.

The inductive system is safe for the user. The susceptors in an embodiment increase in temperature only a few degrees above the target temperature, e.g., 37° C., and are cooled immediately by the dialysis fluid. The temperatures of the tubes carrying the susceptors are not appreciably higher than the target temperature. The temperature sensors have been found to operate well when positioned more than 12.5 mm (one-half inch) from the tubes carrying the fluid to be sensed. Thus close and precise positioning of the disposable tubes with respect to the temperature sensors is not overly critical.

The inductive, inline heating of the present disclosure is advantageous for at least one reason including: being non-invasive or non-contact, having a quick heating response time, operating with a low cost and space saving disposable, having a high power coupling resulting in efficient heating, requiring lower cost electronics, control and sensing, and heating accurately.

Prior to delivering dialysis fluid to the patient, the disposable set, and most importantly the patient line, is primed so that air is not delivered to the patient and volumetric accuracy is not compromised. Existing priming methods typically involve many manual steps and impose a high cognitive load that may strain patients and make the therapy more error prone, potentially exposing patients to harm. The present system and method contemplate the provision of a patient line connector that, once connected to the patient's transfer set, self-primes and then opens to allow dialysis fluid to be delivered to and removed from the patient. The patient does not have to handle the connector during the priming operation in one embodiment.

The connector in one embodiment includes a hydrophobic membrane that is normally sealed closed by a check valve. Under positive pressure during priming, the check valve opens, allowing the priming fluid, e.g., fresh dialysis fluid, to push air out of the patient line and out of the patient connector, through the hydrophobic membrane or vent. The hydrophobic membrane allows air from the patient line to pass through the membrane. Once there is no more air in the patient line, the hydrophobic membrane prevents the dialysis fluid or other priming liquid from passing through the membrane, such that pressure builds in the patient line.

The end of the patient connector is originally sealed via a solid seal, which prevents air from entering the patient's transfer set and aids in forcing the air out through the hydrophobic vent. In one embodiment, the material and thickness of the solid seal are selected so that the seal ruptures open under the pressure that builds after all (or substantially all) of the patient line air has been vented through the hydrophobic membrane. Here, the seal may be provided with score lines or grooves of narrowed thickness so that the solid seal ruptures in a uniform and repeatable way. For example, the score lines may form and X or cross, which tends to rupture at the junction of the score lines and then tear along the score lines outwardly towards the cylindrical connector wall.

In an alternative embodiment, a cutting member is provided, which is not moved while air is being purged from the hydrophobic member of the patient connector, but is moved after the air has been purged and upon the building of fluid pressure trapped in part by the hydrophobic membrane and the solid seal. The cutting member may be in the form of a cylindrical spike made of a resilient and low coefficient of friction material, such as teflon, which is confined to translate within the patient connector over a short distance that is enough to puncture and tear the solid seal. The puncture may occur along the outer rim of the solid seal and the tear may occur along the spike as it translates through the seal. In an embodiment, a portion of the seal remains attached to the patient connector so that the seal is not carried to an undesirable place and so that the seal does not inadvertently reseal the patient connector closed.

In one implementation, which is used with either the punctured or cut solid seal embodiments described above, an outer housing of the patient connector is perforated or provided with a series of holes that allow air to be vented from the patient line under positive pressure. The hydrophobic membrane is provided as a cylinder that has an outer diameter that fits snugly within an inner diameter of the perforated outer housing. The check valve is provided in the form of an elastomeric sleeve, which is stretched so as to be compressed over the outside of the outer housing, covering the series of holes. Under positive pressure, the elastomeric sleeve is stretched open to allow air vented through the hydrophobic membrane and the series of holes to escape to the atmosphere. When negative pressure is applied to the patient line, e.g., for draining the patient, the elastomeric sleeve is press-fit due to its elastic nature and sucked under the negative pressure to the outer housing, covering the holes of the outer housing. In this manner, ambient air is prevented at all times from entering the patient line.

In an alternative implementation, which is not used with the punctured and cut solid seal embodiments described above, first and second members are provided and are hinged to an inner wall of the housing. The members are also each spring biased, e.g., with a stainless steel or medically safe plastic spring, wherein the springs are each initially pulled apart and thus biased to close and to rotate their respective member along its hinge point. The members are also initially latched together in a manner preventing the springs from rotating the first and second members. One of the members is positioned to block dialysis fluid flow into the patient's transfer set. The latching of the members forms a latched member and a latching member. Air is vented through a check valve and hydrophobic membrane arrangement as described above, such that air may escape when the patient line is placed under positive pressure but is prevented from entering the patient line when placed under negative pressure. The pressure in the patient connector while air is being vented through the hydrophobic membrane is not enough to rotate the latched member so as to come free from the latching member. However, when the priming fluid, e.g., fresh dialysis fluid, reaches and wets the hydrophobic membrane, the pressure in the patient connector increases enough to release the latched member from the latching member, such that both members are thereafter rotated via the stretched springs returning to their unbiased position. The members remain in the rotated position regardless of whether they are placed under positive or negative fluid pressure to allow dialysis fluid to flow in either direction through the patient connector and the transfer set.

The patient connectors of the present disclosure reduce the manual effort involved with priming. The connectors also remove a potential source of contamination. The patient is allowed the freedom to connect to the patient line whenever the patient desires instead of being tied to a sequence of priming steps. In some instances, the patient connectors disclosed herein shorten therapy setup time by more than half compared to typical therapy setups. The patient connectors also eliminate or reduce spillage associated with current priming techniques. The use of the patient connectors disclosed herein enable a patient to connect to a patient line then go to sleep as a dialysis system performs self-tests, disposable integrity tests, and priming.

Any of the above-disclosed structures and associated methodologies may be used in connection with premade dialysis fluid, for example, fluid provided in one or more bag to perform a peritoneal dialysis ("PD") treatment. It is contemplated, however, to use any one, or more, or all of the above-disclosed structures and associated methodologies with online dialysis fluid generation, such as online PD fluid generation. The online generation of PD fluid involves the addition of concentrates to water that has been purified to a level that is safe for delivery to the patient. The present system and method contemplate the use of a purified water generation unit that uses distillation to perform at least the bulk of the purification. The primary components of the water distillation unit may include a water tank for receiving tap water or other unpurified water, a heater for boiling the unpurified water to create steam, and a condenser to cool the steam to produce highly purified water, wherein impurities from the water are vented and/or collected at the bottom of the heater and delivered to drain. In an alternative embodiment, the tap water tank is not provided and tap water is instead delivered to the heater via house water pressure.

One or more type of finishing (polishing and/or sterilizing) filter may be located downstream from the condenser, such as, an electrodionization ("EDI") filter, a de-ionization resin filter, and/or one or more ultrafilter. The downstream finishing filter(s) in an embodiment further purifies the water exiting the condenser from a level of pure or ultrapure to being water for injection ("WFI") or of an injectable quality, which is suitable for use to form either peritoneal dialysis ("PD") fluid or a replacement fluid for a blood treatment therapy, such as hemofiltration ("HF") or hemodiafiltration ("HDF").

Optionally, a carbon filter may be placed between the water tank (or house water connection) and the heater to remove chloramines from the tap water prior to reaching the heater. Additionally, a pressure sensor may be located so as to sense pressure in the steam line located between the heater and the condenser. A vent line may be located downstream from the pressure sensor. Valves may be placed in the steam line and the vent line to selectively allow an overpressure in the steam line to be vented to atmosphere and/or volatiles that are freed from the heated water to be vented to atmosphere.

A temperature sensor is located in one embodiment so as to sense the temperature of the purified water exiting the condenser to ensure that the water is safe to be delivered to the point of use, e.g., a mixing location to be combined with concentrates to form a dialysis fluid. A pressure relief valve is also located along the condenser exit line in an embodiment to relieve excess pressure in the purified water prior to reaching the at least one finishing filter, if provided, or to the point of use if the at least one finishing filter is not provided.

The water distillation or purification unit may also include multiple conductivity sensors, such as a first conductivity sensor located adjacent to the temperature sensor in the condenser exit line and a second conductivity sensor located just prior to the exit of the WFI from the water distillation unit, e.g., just downstream from the at least one finishing filter.

In an embodiment, each of the heater, condenser, valves, pressure sensors, temperature sensor and conductivity sensors are under microprocessor control of the control unit for the overall system, which may include one or more processor and one or more memory. In an embodiment, the control unit includes a user interface having a display device under control of a video controller in communication with the at least one processor and the at least one memory. The control unit determines when purified water or WFI is needed and, for example, how much (e.g., data concerning demand). In an embodiment, the control unit also controls the temperature of the purified water or WFI that is outputted. In this manner, the distillation unit may lessen the burden on the inline heater described herein.

In one embodiment, the water is heated by applying a large AC electrical potential to a pair of electrodes that are submerged in the tap water, wherein the electrodes are separated from each other such that current has to pass through the tap water to complete an electrical circuit. The electrodes are made of a medically compatible and at least somewhat electrically conductive material, such as stainless steel (e.g., 304 or 316) or titanium. The electrodes in an embodiment each include baffles that are interleaved within baffles of the other electrode, so as to increase the overall surface area of adjacently juxtaposed electrode material. The increased surface area increases the speed at which the heater boils the tap water.

The heater in one embodiment includes an electrically and thermally insulative disposable lining fitted into a rigid base into which the disposable electrodes are placed and held fixed in a non-contacting relationship. Electrical leads are inserted sealingly through a wall of the base and are placed into electrical communication with the electrodes. The electrical leads are connected to a power source, which for example is configured to apply 1000 to 2000 Watts of power to the electrical leads and therefore to the electrodes and tap water located between the electrodes.

A cover, e.g., an electrically and thermally insulative cover, is removeably, e.g., hingedly, connected to the base, such that the cover allows access to the disposable liner electrodes for replacement. The cover in one embodiment provides two ports, one for connection to a water source (tank or tap water directly), and another for connection to a steam line, which carries steam from the heater to the condenser.

As is known, the process of distillation involves separating components or substances, in the present case volatiles, from a liquid, in one example tap water, using selective boiling and condensation. The volatiles of the present distillation process are either collected at the bottom of the base of the heater and discharged intermittently from the heater to a drain via a drain valve, are removed via the disposable liner or tray, and/or are vented through a vent in a vent line extending from the top of the heater. It has been found that the more volatile substances are vented to the atmosphere, while the least volatile substances are flushed to the drain or removed via the disposable tray or liner. Water is of intermediate volatility. The most volatile substances boil first and the resultant gas is vented. Water boils next and the resulting gas (steam) is condensed back into liquid. The least volatile parts (including some water) never boil and are flushed to drain or removed via the disposable instead.

In one embodiment, the condenser includes a condensing coil, which is made of a thermally conductive and medically safe material, such as stainless steel (e.g., 304 or 316) or titanium. Plural heat fins, such as highly thermally conductive copper heat fins, are attached to the coil, e.g., via soldering, welding, brazing, gluing and/or mechanical connection. The heat fins conduct heat away from the coil and the steam located within the coil. The coil includes an inlet and an outlet, wherein the inlet is located at the top of the coil and the outlet is located at the bottom of the coil. In this manner, steam from the heater enters into inlet the top of the coil, while highly purified water exits the outlet at the bottom of the coil.

The condenser also includes a fan, which is located inside of the coil and associated heat fins. The fan in an embodiment has upper and lower fan blade holders that are attached respectively to upper and lower fixtures via bearings, such as ball or roller bearings. The upper and lower fan blade holders spin around a vertical axis of rotation extending through the centers of each of the bearings. The fan's blades are in an embodiment vertically disposed paddles or baffles that are formed with (e.g., a single molded piece) or are connected to the upper and lower fan blade holders so as to extend radially from the vertical axis of rotation. The upper and lower bearings are placed in a rotationally fixed relationship with upper and lower fixtures, so as to hold the fan blades firmly in place but allow the blades to spin freely about the central, vertical axis of the fan. In an alternative embodiment, the fan blades may be held fixed to a vertical shaft that extends along and spins around the length of the central, vertical axis of rotation.

The output shaft of a fan motor is coupled via a direct coupler, or via a geared or belt and pulley relationship as desired, to one of the fan blade holders. In operation, the fan motor, under control of the control unit for the dialysis system causes the fan blade holder, the blades connected to the holder, and an opposing holder holding the other end of the fan blades to spin. The spinning of the blades pulls air in from above and below and drives air radially outwardly and over the copper heat fins connected to the condenser coil, causing convective heat transfer away from the steam traveling through the condenser coil.

In an embodiment, the control unit of the dialysis system is configured to receive a desired purified water exit temperature. The control unit in turn accesses a look-up table or algorithm that correlates the purified water exit temperature with the speed of the fan and boiler power. The control unit in turn sets the boiler power and fan speed to be the correlated fan speed for the desired water exit temperature. In this embodiment, the fan motor for the fan is a variable speed motor and the boiler power is variable. Providing water at a temperature elevated above ambient is advantageous for PD or blood treatment applications, which require the resulting mixed dialysis fluid to be at or near body temperature, e.g., 37° C., as discussed above for the inductive heater. Here, heating energy required by the inductive heater is conserved.

In an alternative embodiment, the fan motor is a single speed motor and the outlet condenser temperature of the purified water is whatever temperature is achieved via the single speed. It is contemplated in alternative embodiments to provide other types of cooling for the condensing operation, such as water cooling. For example, if a tap water storage tank is provided, it is contemplated to place the condensing coil, e.g., without heat fins, which may again be made be from a medically safe material, such as, stainless steel (e.g., 304, 316) or titanium, in the tap water tank to (i) cool the steam from the heater and (ii) preheat the tap water so that power usage at the heater is reduced. Here, the control unit is programmed to make sure enough tap water is present in the water tank to adequately cool the condensing coil, even if some of the tap water is not eventually purified and is provided instead only for cooling. Multiple water cooled heat exchangers may be provided if desired to condense the steam.

In an embodiment, the system pump (e.g., peristaltic pump) pumps purified water, e.g., WFI, to the vertically disposed and sterilized bag located within the vertically disposed clamshell holder. To form dialysis fluid from the WFI, the system of the present disclosure adds concentrate and mixes the WFI and concentrate. In an embodiment, the sterilized bag is provided with one or more sterilized tube that is preloaded with one or more concentrate capsule. A slideable plug, e.g., rubber plug, is located at the end of each sterilized tube. The plug is fitted in an airtight manner within the tube so as to maintain the sterility of the bag, tube and concentrate capsules. The slideable plug, the concentrate capsules, and the tube are sized so that the plug and capsules are held press-fittingly within the tube so that neither the plug nor the capsules move until the plug is acted upon as discussed below. The press-fitting of the capsules is enough to hold the capsules in place regardless of the orientation of the sterilized bag. In an alternative embodiment, a thin rupturable seal may be formed or fitted within the tube, capturing the concentrate capsules between the plug and seal.

The dialysis machine, e.g., at the clamshell holder, provides dispensing actuators, for example, a dispensing actuator for each concentrate capsule containing tube. When the user loads the sterilized bag with concentrate tubes into the clamshell holder, the user also connects the end of each concentrate tube with one of the dispensing actuators. In one embodiment, the user inserts each concentrate tube over an extender located within each dispensing actuator so that the slideable plug within the concentrate tube is abutted against one of the ends of the extender. The extender includes gear teeth extending from a stem in one embodiment, which mesh with mating teeth of one or more rotating gear located within each dispensing actuator. The one or more rotating gear is driven, for example, by a stepper motor, which may index the extender over short and precise distances to in turn translate the plug within the sterilized concentrate tube a short distance, which dispenses one or more concentrate capsule into the WFI located within the sterilized bag.

The control unit of the overall dialysis system is programmed to cause the stepper motor or other indexer to index the extender a preset distance one or more time during treatment to mix one or more supply of fresh dialysis fluid. Each index may cause one or more concentrate capsule to be delivered to the WFI. As mentioned above, multiple dispensing actuators may be provided, e.g., one for indexing electrolyte capsules and another for indexing osmotic agent capsules. Those two actuators may also be used to dispense other types of capsules, such as pH buffers and diagnostic agents. Or, additional actuators may be provided to dispense the additional capsules. When treatment is completed, the control unit may be programmed to cause the stepper motor or other indexer to reverse direction and pull the extender from the concentrate tube and retreat to a starting position for the next treatment.

The concentrate capsules may include an outer gel coating forming a sphere or spherocylinder (cylinder with semispherical ends). The gel coating may hold a powder or liquid depending on the type of concentrate. The powder or liquid may have a highest possible concentration so that the capsule is as small as possible. The quantity and concentration of the powdered or liquid concentrate are selected to as to be mixed with a known volume of WFI located within the sterile flexible bag held by the clamshell holder to form a desired dialysis fluid when fully mixed, e.g., a 1.5%, 2.5% or 4.25% dextrose PD solution.

The control unit is configured to cause the system pump to circulate the WFI and concentrate capsules from and back into the sterile bag multiple times, perhaps reversing direction, so that the gel coatings dissolve, allowing the concentrate powder or liquids to mix homogeneously with the WFI. The control unit may also control the inline heater to partially or fully heat the dialysis fluid during the mixing sequence. In an embodiment, the sterile bag is only partially filled with WFI when the one or more concentrate capsule is added during the mixing sequence to help homogenize the solution more quickly. The remainder of the WFI is then added to reach the desired dialysis fluid formulation. Proportioning is performed on a volumetric basis as described, however, analyzing solution conductivity may be performed alternatively or as a confirmation.

As mentioned above, it is contemplated to provide one or more diagnostic capsule, which is stored as the last capsule in an electrolyte or osmotic agent tube (or in a separate tune), and which is inserted into a known amount of effluent pumped into the sterilized bag at the end of treatment. It is contemplated to let the diagnostic capsule dissolve into the effluent, after which the patient brings the effluent bag to a clinic for analysis. It is also contemplated for the dialysis system to provide onsite diagnostic equipment, e.g., as part of the dialysis machine, which analyzes the effluent solution. Here, after inserting the one or more diagnostic capsule, the control unit may cause the effluent and capsule to mix in a manner described above. Once the diagnostic concentrate is dispersed homogenously with the effluent, the effluent solution is analyzed. In one embodiment, the effluent solution is analyzed by modulating a light array across a spectrum of wavelengths and measuring the incident light with a photodiode sensor array, which provides more nuanced data as opposed to while light or a color camera.

Diagnostic capsules may be provided to detect white blood cells or other markers of peritonitis. The capsules may additionally be formulated to look for urea, electrolytes, and phosphates, for example. It is contemplated that the control unit of the system be connected to a server, which may be accessed by any one or more of the provider of the system, a clinician, a doctor's office, a service portal, or a patient website. The effluent data may be tracked, e.g., by the patient's clinician or doctor, to determine the effectiveness of therapy, look for peritonitis or other patient condition needing attention, and possibly to send an updated patient prescription from the clinician or doctor, through the server, to the dialysis system to run a modified treatment.

While some of the effluent may be used for analysis and sampling as described, it is also contemplated to regenerate the remainder, or at least some of the remainder, of the effluent into purified water, e.g., WFI, for a next treatment. Here, the system pump pumps the effluent to the tap water tank of the water distillation unit. The distillation unit removes the water from the effluent, vaporizing and venting or collecting and discarding effluent residuals. For PD, it is contemplated that the tap water tank of the water distillation unit be sized to hold twice the patient's fill volume worth of tap water. For instance, if the patient's fill volume is 1.5 liters, the tap water tank may be sized to hold three or more liters of tap water. At the start of treatment, 1.5 liters of tap water is purified into WFI, sent to the flexible bag in the clamshell holder, mixed to produce dialysis fluid, and delivered to the patient. While dwelling within the patient, the second 1.5 liters of tap water is purified into WFI, sent to the flexible bag in the clamshell holder, and mixed to produce dialysis fluid, which waits until the patient dwell and drain to the purification unit of the first fill is completed. The second batch of dialysis fluid is then delivered to the patient. The effluent residing in the purification unit is then purified into WFI, and the above cycle is repeated.

In light of the disclosure herein and without limiting the disclosure in any way, in a first aspect of the present disclosure, which may be combined with any other aspect listed herein, a dialysis fluid apparatus includes: a flexible dialysis fluid container; a holder structured such that the flexible dialysis fluid container is held vertically within the holder and conforms to a shape of the holder; a pressure sensor positioned and arranged to sense a pressure of a fluid held within the flexible dialysis fluid container; and a control unit configured to (i) store at least one cross-sectional area of the flexible dialysis fluid container, (ii) calculate a head height using the pressure of the fluid held within the flexible dialysis fluid container, and (iii) calculate a volume of the fluid held within the flexible dialysis fluid container using the cross-sectional area and the head height.

In a second aspect of the present disclosure, which may be combined with any other aspect listed herein, the flexible dialysis fluid container includes a flexible bag.

In a third aspect of the present disclosure, which may be combined with any other aspect listed herein, the holder is structured as a clamshell having open sides.

In a fourth aspect of the present disclosure, which may be combined with any other aspect listed herein, the control unit is configured to calculate the head height as a difference in head height of the fluid held within the flexible dialysis fluid container prior to and after a delivery of the fluid to or from the flexible dialysis fluid container.

In a fifth aspect of the present disclosure, which may be combined with any other aspect listed herein, the head height is a first head height and the volume is a first volume, and wherein the control unit is configured to calculate a second head height and a second volume of the fluid held within the flexible dialysis fluid container using the second head height.

In a sixth aspect of the present disclosure, which may be combined with any other aspect listed herein, a cross-sectional area for the calculation of the second volume is the same as the cross-sectional area for the calculation of the first volume.

In a seventh aspect of the present disclosure, which may be combined with any other aspect listed herein, a cross-sectional area for the calculation of the second volume is different than the cross-sectional area for the calculation of the first volume.

In an eighth aspect of the present disclosure, which may be combined with any other aspect listed herein, the control unit is further configured to (i) store a lookup table that correlates the measured pressure of the fluid held within the flexible dialysis fluid container with cross-sectional area and (ii) obtain the different cross-sectional areas using the lookup table and the first and second measured pressures corresponding respectively to the first and second head heights.

In a ninth aspect of the present disclosure, which may be combined with any other aspect listed herein, the control unit is further configured to determine a difference between the first and second volumes to determine an amount of the fluid delivered to or removed from the flexible dialysis fluid container.

In a tenth aspect of the present disclosure, which may be combined with any other aspect listed herein, the control unit is further configured to determine a flowrate of the fluid delivered to or removed from the flexible dialysis fluid container by dividing the difference between the first and second volumes by a time duration between the first and second measured pressures corresponding respectively to the first and second head heights.

In an eleventh aspect of the present disclosure, which may be combined with any other aspect listed herein, the control unit is further configured to determine the flowrate on a periodic basis.

In a twelfth aspect of the present disclosure, which may be combined with any other aspect listed herein, calculating head height in (ii) of the first aspect is dependent on the density of the fluid, and wherein the control unit stores a look-up table that correlates fluid density to fluid type.

In a thirteenth aspect of the present disclosure, which may be combined with any other aspect listed herein, calculating head height in (ii) of the first aspect is dependent on the density of the fluid, and wherein the control unit is configured such that when the fluid held within the flexible dialysis fluid container is mixed, the control unit uses different densities for different head height calculations.

In a fourteenth aspect of the present disclosure, which may be combined with any other aspect listed herein, the dialysis fluid apparatus includes a level sensor placed in operable communication with the flexible dialysis fluid container, the level sensor outputting to the control unit, the control unit configured to at least one of (i) cause an alarm or (ii) halt delivery of the fluid to or removal of the fluid from the flexible dialysis fluid container when a level of the fluid falls so as to be detected by the level sensor.

In a fifteenth aspect of the present disclosure, which may be combined with any other aspect listed herein, the level sensor is located so as to sense an area above the flexible dialysis fluid container that transitions in cross-sectional area towards a delivery tube in fluid communication with the flexible dialysis fluid container.

In a sixteenth aspect of the present disclosure, which may be combined with any other aspect listed herein, the pressure sensor includes a pressure pouch in pressure transmission communication with a pressure transducer, the pressure pouch mounted to the holder such that the flexible dialysis fluid container contacts the pressure pouch.

In a seventeenth aspect of the present disclosure, which may be combined with any other aspect listed herein, a dialysis fluid apparatus includes: a flexible dialysis fluid container; a peristaltic pump tube placed in fluid communication with the flexible dialysis fluid container; a holder structured such that the flexible dialysis fluid container is held vertically within the holder and conforms to a shape of the holder; a pressure sensor positioned and arranged to sense a pressure of a fluid pumped to or from the flexible dialysis fluid container via the peristaltic pump tube; and a control unit configured to (i) store at least one cross-sectional area of the flexible dialysis fluid container, (ii) calculate a head height using the pressure of the fluid pumped to or from the flexible dialysis fluid container via the peristaltic pump tube, and (iii) calculate a volume of the fluid held within the flexible dialysis fluid container using the cross-sectional area and the head height.

In an eighteenth aspect of the present disclosure, which may be combined with any other aspect listed herein, the peristaltic pump tube is additionally placed in selective fluid communication with at least one of: a fluid source, a fluid heater, or a patient line.

In a nineteenth aspect of the present disclosure, which may be combined with any other aspect listed herein, a dialysis fluid apparatus includes: a flexible dialysis fluid container; a holder structured such that the flexible dialysis fluid container is held vertically within the holder and conforms to a shape of the holder; a pressure sensor including a pressure pouch positioned and arranged to contact a bottom of the flexible dialysis fluid container and a pressure transducer in pressure transmission communication with the pressure pouch to sense a pressure of a fluid held within the flexible dialysis fluid container; and a control unit configured to (i) store at least one cross-sectional area of the flexible dialysis fluid container, (ii) calculate a head height using the pressure of the fluid held within the flexible dialysis fluid container, and (iii) calculate a volume of the fluid held within the flexible dialysis fluid container using the cross-sectional area and the head height.

In a twentieth aspect of the present disclosure, which may be combined with any other aspect listed herein, the pressure pouch and the pressure transducer are in pneumatic communication.

In a twenty-first aspect of the present disclosure, which may be combined with any other aspect listed herein, an inductive dialysis fluid heater includes: a cylindrical tube including an inner diameter from 4.00 mm to 12.7 mm; a susceptor located within the cylindrical tube; an inductive coil extending around the cylindrical tube in a non-contacting arrangement; and power electronics in electrical communication with the inductive coil and configured to supply an electrical current to the inductive coil, causing the susceptor to heat.

In a twenty-second aspect of the present disclosure, which may be combined with any other aspect listed herein, the power electronics includes a resonant circuit.

In a twenty-third aspect of the present disclosure, which may be combined with any other aspect listed herein, the power electronics includes driver electronics for the resonant circuit.

In a twenty-fourth aspect of the present disclosure, which may be combined with any other aspect listed herein, the susceptor is at least substantially smooth to mitigate a pressure drop caused by the susceptor.

In a twenty-fifth aspect of the present disclosure, which may be combined with any other aspect listed herein, the susceptor is provided in the form of a mesh.

In a twenty-sixth aspect of the present disclosure, which may be combined with any other aspect listed herein, the cylindrical tube is a first cylindrical tube and the susceptor is a first susceptor, and which includes a second cylindrical tube and a second susceptor located within the second cylindrical tube, and wherein inductive coil extends around the first and second cylindrical tubes.

In a twenty-seventh aspect of the present disclosure, which may be combined with any other aspect listed herein, the second cylindrical tube has a same inner diameter as the first cylindrical tube.

In a twenty-eighth aspect of the present disclosure, which may be combined with any other aspect listed herein, the first and second cylindrical tubes are connected by a U-shaped connector.

In a twenty-ninth aspect of the present disclosure, which may be combined with any other aspect listed herein, the first and second cylindrical tubes are first and second tube portions folded 180 degrees from a single tube.

In a thirtieth aspect of the present disclosure, which may be combined with any other aspect listed herein, the inductive dialysis fluid heater includes a downstream temperature sensor located so as to sense a temperature of fluid heated by the first and second susceptors and an upstream temperature sensor located so as to sense a temperature of the fluid prior to being heated, the first and second temperature sensors outputting to a control unit controlling the power electronics.

In a thirty-first aspect of the present disclosure, which may be combined with any other aspect listed herein, the inductive dialysis fluid heater includes a downstream temperature sensor located so as to sense a temperature of fluid heated by the susceptor and an upstream temperature sensor located so as to sense a temperature of the fluid prior to being heated, the first and second temperature sensors outputting to a control unit controlling the power electronics.

In a thirty-second aspect of the present disclosure, which may be combined with any other aspect listed herein, a dialysis system includes: a disposable set including a tube, and a susceptor located within the cylindrical tube; a machine enclosure including an opening sized to accept the cylindrical tube; an inductive coil located within the machine enclosure and extending around the cylindrical tube when the cylindrical tube is inserted into the opening; and power electronics located within the machine enclosure, the power electronics in electrical communication with the inductive coil and configured to supply an electrical current to the inductive coil, causing the susceptor to heat.

In a thirty-third aspect of the present disclosure, which may be combined with any other aspect listed herein, the cylindrical tube is a first cylindrical tube and the susceptor is a first susceptor, and which includes a second cylindrical tube and a second susceptor located within the second cylindrical tube, and wherein inductive coil extends around the first and cylindrical tubes when inserted into the opening.

In a thirty-fourth aspect of the present disclosure, which may be combined with any other aspect listed herein, the first and second cylindrical tubes are connected by a U-shaped connector.

In a thirty-fifth aspect of the present disclosure, which may be combined with any other aspect listed herein, the first and second cylindrical tubes are first and second tube portions folded 180 degrees from a single tube.

In a thirty-sixth aspect of the present disclosure, which may be combined with any other aspect listed herein, the dialysis fluid system includes (i) a downstream temperature sensor located within the machine enclosure so as to sense a temperature of fluid heated by the first and second susceptors when the disposable set is mounted to the machine enclosure and (ii) an upstream temperature sensor located within the machine enclosure so as to sense a temperature of the fluid prior to being heated when the disposable set is mounted to the machine enclosure.

In a thirty-seventh aspect of the present disclosure, which may be combined with any other aspect listed herein, the dialysis fluid system includes a control unit, the first and second temperature sensors outputting to the control unit controlling the power electronics.

In a thirty-eighth aspect of the present disclosure, which may be combined with any other aspect listed herein, the dialysis fluid system includes (i) a downstream temperature sensor located within the machine enclosure so as to sense a temperature of fluid heated by the susceptor when the disposable set is mounted to the machine enclosure and (ii) an upstream temperature sensor located within the machine enclosure so as to sense a temperature of the fluid prior to being heated when the disposable set is mounted to the machine enclosure.

In a thirty-ninth aspect of the present disclosure, which may be combined with any other aspect listed herein, the machine enclosure presents a pump actuator, and wherein the disposable set includes a pumping portion for operation with the pump actuator.

In a fortieth aspect of the present disclosure, which may be combined with any other aspect listed herein, the pumping portion includes a cylindrical tube which is the same as or is in fluid communication with the cylindrical tube housing the susceptor.

In a forty-first aspect of the present disclosure, which may be combined with any other aspect listed herein, a patient connector for dialysis includes: a housing including an inlet and an outlet and defining at least one aperture; a seal initially blocking the outlet; a hydrophobic filter covering the at least one aperture; and a check valve positioned and arranged to prevent air from being vented from the housing via the at least one aperture and through the hydrophobic filter when the housing is under atmospheric pressure or negative pressure, the check valve configured to allow air to be vented from the housing via the at least one aperture and through the hydrophobic filter when the housing is under positive pressure.

In a forty-second aspect of the present disclosure, which may be combined with any other aspect listed herein, the hydrophobic filter is configured to allow air under positive pressure from a patient line connected to the patient connector to be vented through the at least one aperture and to disallow a liquid from escaping through the at least one aperture after the liquid has traveled through the patient line to reach the connector.

In a forty-third aspect of the present disclosure, which may be combined with any other aspect listed herein, the seal initially blocking the outlet is configured to rupture under pressure from the liquid after reaching the connector and building pressure against the seal.

In a forty-fourth aspect of the present disclosure, which may be combined with any other aspect listed herein, the seal is configured to rupture due to at least one of its thickness or geometry.

In a forty-fifth aspect of the present disclosure, which may be combined with any other aspect listed herein, the seal is scored to provide rupture lines.

In a forty-sixth aspect of the present disclosure, which may be combined with any other aspect listed herein, the patient connector includes a cutting member located within the housing so as to be moved by the liquid reaching the connector to open the seal.

In a forty-seventh aspect of the present disclosure, which may be combined with any other aspect listed herein, the housing is cylindrical and which includes a cylindrical spike translated by the liquid reaching the connector to pierce the seal.

In a forty-eighth aspect of the present disclosure, which may be combined with any other aspect listed herein, the patient connector includes a spring-loaded latched member holding the seal so as to initially block the outlet and a spring-loaded latching member latching the latched member so as to prevent the latched member from moving due to its spring-loading to unblock the outlet, and wherein the liquid reaching the connector causes the latched member to become unlatched from the latching member and to move due to its spring-loading so that the seal unblocks the outlet.

In a forty-ninth aspect of the present disclosure, which may be combined with any other aspect listed herein, the hydrophobic filter is positioned to cover the at least one aperture along an outer wall of the housing, and wherein the check valve is biased to press the hydrophobic filter against the outer wall.

In a fiftieth aspect of the present disclosure, which may be combined with any other aspect listed herein, the hydrophobic filter is positioned to cover the at least one aperture along an inner wall of the housing.

In a fifty-first aspect of the present disclosure, which may be combined with any other aspect listed herein, the housing and the hydrophobic filter are cylindrical and the hydrophobic filter is located coaxially within the housing so as to cover the at least one aperture along the inner wall of the housing.

In a fifty-second aspect of the present disclosure, which may be combined with any other aspect listed herein, the check valve includes an elastomeric sleeve that press-fits over the cylindrical housing so as to cover the at least one aperture, the elastomeric sleeve expanding under positive pressure to allow air to be vented from the housing through the hydrophobic filter and at least one aperture.

In a fifty-third aspect of the present disclosure, which may be combined with any other aspect listed herein, the housing defines a plurality of apertures and the elastomeric sleeve is cylindrical and sized to cover each of the plurality or apertures.

In a fifty-fourth aspect of the present disclosure, which may be combined with any other aspect listed herein, a patient connector for dialysis includes: a housing including an inlet and an outlet and defining at least one aperture; a seal initially blocking the outlet; a hydrophobic filter covering the at least one aperture along an inner wall of the housing; and an elastomeric sleeve that press-fits over the housing (e.g., connected to the housing) so as to cover the at least one aperture, the elastomeric sleeve expanding under positive pressure to allow air to be vented from the housing through the hydrophobic filter and at least one aperture.

In a fifty-fifth aspect of the present disclosure, which may be combined with any other aspect listed herein, the housing and the hydrophobic filter are cylindrical and the hydrophobic filter is located coaxially within the housing so as to cover the at least one aperture along the inner wall of the housing.

In a fifty-sixth aspect of the present disclosure, which may be combined with any other aspect listed herein, a dialysis fluid priming method includes: configuring a patient connector such that a patient can connect the connector to the patient's indwelling catheter connector prior to delivery of dialysis fluid through a patient line in fluid communication with the patient connector; and enabling the patient to thereafter cause dialysis fluid to be delivered through the patient line, wherein the patient connector (i) allows the dialysis fluid to vent air through the connector, and (ii) allows the dialysis fluid to establish fluid communication between the connector and the patient's indwelling catheter after the air has been vented through the catheter.

In a fifty-seventh aspect of the present disclosure, which may be combined with any other aspect listed herein, the patient connector closes an opening allowing the air to be vented under atmospheric or negative pressure and opens the opening allowing the dialysis fluid to vent the air through the connector under positive pressure from the incoming dialysis fluid.

In a fifty-eighth aspect of the present disclosure, which may be combined with any other aspect listed herein, the patient connector provides a seal configured to rupture under pressure from the dialysis fluid to allow the dialysis fluid to establish fluid communication between the connector and the patient's indwelling catheter.

In a fifty-ninth aspect of the present disclosure, which may be combined with any other aspect listed herein, the patient connector provides a cutting member configured to be moved by the incoming dialysis fluid to pierce a seal to establish fluid communication between the connector and the patient's indwelling catheter.

In a sixtieth aspect of the present disclosure, which may be combined with any other aspect listed herein, the patient connector provides interlocking members that are unlocked by the incoming dialysis fluid to pierce a seal to establish fluid communication between the connector and the patient's indwelling catheter.

In a sixty-first aspect of the present disclosure, which may be combined with any other aspect listed herein, a dialysis fluid container includes: a fluid enclosure for holding a fluid; a tube connected to the enclosure; a plug located press-fittingly within the tube; and at least one concentrate capsule located within the tube between the plug and the enclosure.

In a sixty-second aspect of the present disclosure, which may be combined with any other aspect listed herein, the enclosure includes a flexible bag.

In a sixty-third aspect of the present disclosure, which may be combined with any other aspect listed herein, the tube and the at least one capsule are sized to hold the at least one capsule in place regardless of an orientation of the container.

In a sixty-fourth aspect of the present disclosure, which may be combined with any other aspect listed herein, the tube and the at least one capsule are provided in a sterilized form.

In a sixty-fifth aspect of the present disclosure, which may be combined with any other aspect listed herein, the at least one concentrate capsule is of at least one type selected from the group consisting of an electrolyte capsule, an osmotic agent capsule, a pH buffer capsule and a diagnostic agent capsule.

In a sixty-sixth aspect of the present disclosure, which may be combined with any other aspect listed herein, the dialysis fluid container includes a plurality of concentrate capsules located within the tube, the capsules provided in an order in which it is intended for the capsules to be dispensed into the enclosure.

In a sixty-seventh aspect of the present disclosure, which may be combined with any other aspect listed herein, the plurality of capsules includes at least one capsule for each fill cycle of a peritoneal dialysis treatment.

In a sixty-eighth aspect of the present disclosure, which may be combined with any other aspect listed herein, the plurality of capsules includes at least one pH buffer capsule or at least one diagnostic agent capsule located between the plug and at least one dialysis fluid preparation capsule.

In a sixty-ninth aspect of the present disclosure, which may be combined with any other aspect listed herein, the tube is a first tube, the plug is a first plug and the at least one concentrate capsule is a first at least one capsule, and which includes a second tube connected to the enclosure, a second plug located press-fittingly within the second tube, and a second at least one concentrate capsule located within the second tube between the second plug and the enclosure.

In a seventieth aspect of the present disclosure, which may be combined with any other aspect listed herein, the first tube holds at least one first dialysis fluid preparation capsule and the second tube holds at least one second, different dialysis fluid preparation capsule.

In a seventy-first aspect of the present disclosure, which may be combined with any other aspect listed herein, at least one of the first and second tubes additionally holds at least one pH buffer capsule or at least one diagnostic agent capsule.

In a seventy-second aspect of the present disclosure, which may be combined with any other aspect listed herein, the at least one concentrate capsule includes an outer gel sphere or sphereocylinder in which a powder or liquid concentrate is held.

In a seventy-third aspect of the present disclosure, which may be combined with any other aspect listed herein, the powder or liquid is provided in a quantity and concentration that alone or in combination with at least one additional concentrate capsule is proportioned to be mixed with a certain volume of purified water to form a desired dialysis fluid.

In a seventy-fourth aspect of the present disclosure, which may be combined with any other aspect listed herein, a dialysis fluid container system includes: a fluid enclosure; a tube connected to the enclosure; a plug located press-fittingly within the tube; at least one concentrate capsule located within the tube between the plug and the enclosure; an extender sized to fit within the tube to contact and move the plug to in turn move the at least one concentrate capsule along the tube; and an actuator positioned and arranged to index the extender.

In a seventy-fifth aspect of the present disclosure, which may be combined with any other aspect listed herein, the actuator includes at least one driver contacting the extender and an indexer operably coupled to move the at least one driver to in turn index the extender.

In a seventy-sixth aspect of the present disclosure, which may be combined with any other aspect listed herein, the at least one driver includes at least one rotating gear and the extender includes gear teeth sized to mate with the at least one rotating gear.

In a seventy-seventh aspect of the present disclosure, which may be combined with any other aspect listed herein, the at least one rotating gear includes first and second rotating gears, and wherein the actuator includes a third rotating gear that rotates along a same shaft as the first rotating gear and a fourth rotating gear in geared communication with the third rotating gear, the fourth rotating gear rotating along a same shaft as the second rotating gear, and wherein the indexer is coupled to one of the third or fourth rotating gears.

In a seventy-eighth aspect of the present disclosure, which may be combined with any other aspect listed herein, the indexer includes a stepper motor.

In a seventy-ninth aspect of the present disclosure, which may be combined with any other aspect listed herein, the actuator and extender are reusable.

In an eightieth aspect of the present disclosure, which may be combined with any other aspect listed herein, at least a portion of the actuator is mounted to a holder for holding the fluid enclosure.

In an eighty-first aspect of the present disclosure, which may be combined with any other aspect listed herein, a dialysis fluid system includes: a fluid enclosure; a tube connected to the enclosure; a plug located press-fittingly within the tube; at least one concentrate capsule located within the tube between the plug and the enclosure; an extender sized to fit within the tube to contact and move the plug to in turn move the at least one concentrate capsule along the tube and into the fluid enclosure; and fluid lines and a pump positioned and arranged to circulate purified water through fluid enclosure and the fluid lines after the at least one concentrate capsule has been moved into the fluid enclosure to mix the purified water and concentrate held by the at least one concentrate capsule.

In an eighty-second aspect of the present disclosure, which may be combined with any other aspect listed herein, the dialysis fluid system includes a control unit configured to (i) store an amount of the purified water to mix with the at least one concentrate capsule and (ii) cause only a portion of the amount to be mixed initially with the at least one concentrate capsule.

In an eighty-third aspect of the present disclosure, any of the structure and functionality disclosed in connection with FIGS. 1 to 26 may be combined with any of the other structure and functionality disclosed in connection with FIGS. 1 to 26.

In light of the present disclosure and the above aspects, it is therefore an advantage of the present disclosure to provide an improved volume control apparatus and associated methodology for a dialysis system.

It is another advantage of the present disclosure to provide an improved dialysis fluid heating apparatus and associated methodology for a dialysis system.

It is a further advantage of the present disclosure to provide an improved patient line connector and associated methodology for a dialysis system.

It is still another advantage of the present disclosure to provide an improved dialysis fluid concentrate mixing apparatus and associated methodology for an online dialysis system.

It is still a further advantage of the present disclosure to provide an improved online dialysis system.

It is yet another advantage of the present disclosure to provide a regenerative dialysis system.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein, and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

System Overview

Figure 1:
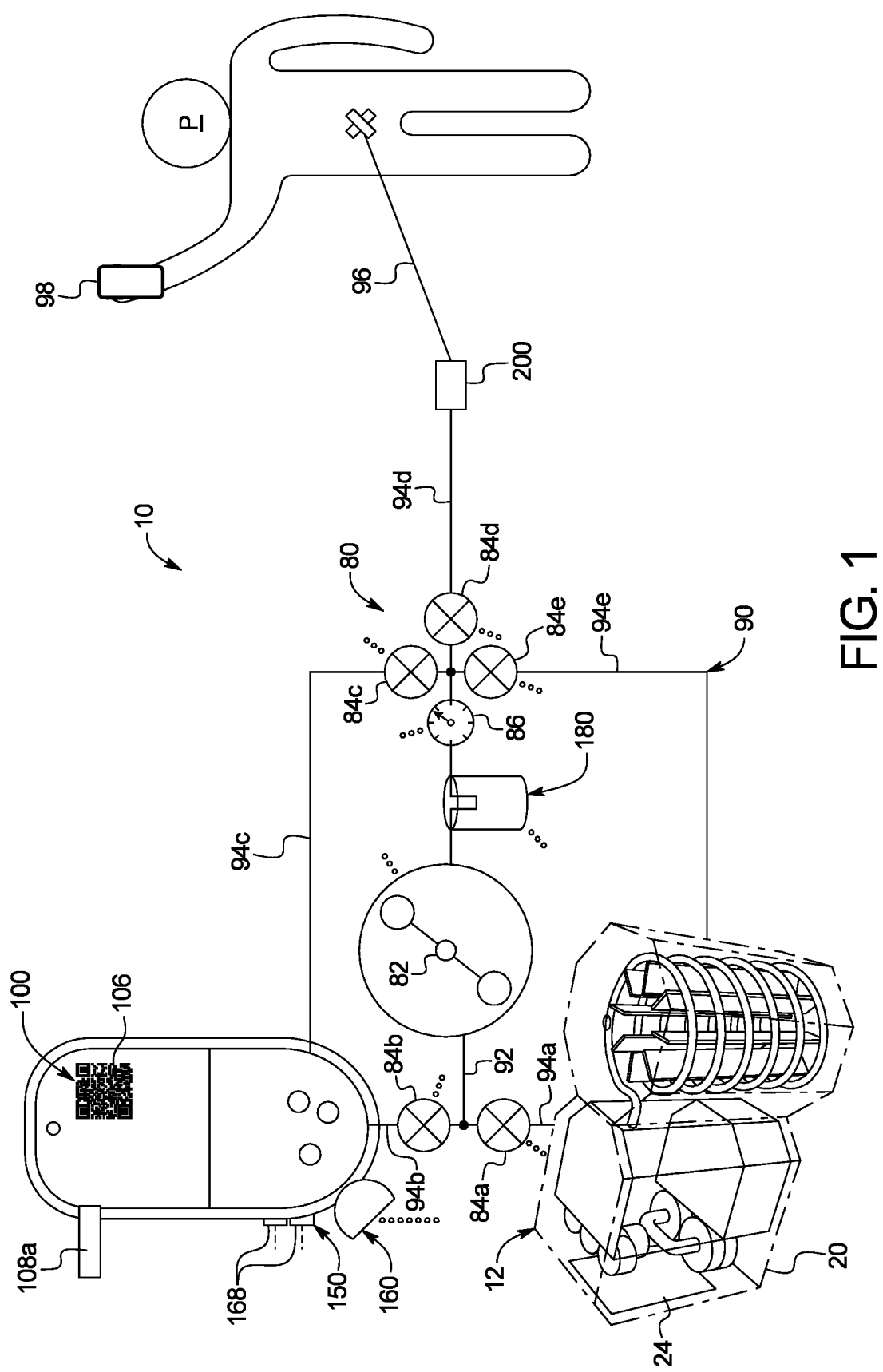
FIG. 1 is a perspective view of one embodiment of an online and regenerative dialysis system of the present disclosure.

Referring now to the drawings and in particular to FIG. 1, a dialysis system 10 is illustrated. Dialysis system 10 as illustrated and described herein is capable of preparing purified water or water for injection ("WFI"), mixing the purified water or WFI with concentrate to form dialysis fluid online, heating the dialysis fluid inline, and delivering the dialysis fluid to patient P via a self-priming patient connector. It should be appreciated however that various alternative embodiments are described herein, which do not have to have each of the above features and corresponding structures. It is expressly contemplated that the features and corresponding structures are patentable separately and in any combination. It should also be appreciated that while the present disclosure is described generally for peritoneal dialysis ("PD"), many of the features and corresponding structure are useful in other modalities, such as hemodialysis ("HD"), hemofiltration ("HF"), hemodiafiltration ("HDF") and/or medical fluid delivery generally.

In the illustrated embodiment of FIG. 1, system 10 includes a distillation unit 12, which purifies tap water or used dialysis fluid into purified water or WFI. As used herein, purified water includes WFI, however purified water may be less sterile than WFI. For example, purified water may be suitable for HD, which pumps dialysis fluid along one side of dialyzer membranes, while WFI may be required for PD, which along with other modalities directs dialysis fluid to patient P.

Purified water is delivered from distillation unit 12 to a dialysis fluid mixing container 100, such as a flexible bag. Dialysis fluid mixing container 100 in the one embodiment is placed within a holder 152 (FIG. 9) of a dialysis fluid volume control subsystem 150. Dialysis fluid is prepared within dialysis fluid mixing container 100 in an embodiment by supplying one or more tube 108a, 108b (FIG. 5) connected to dialysis fluid container 100. As illustrated in detail below, a plug is located press-fittingly near a distal end of the tube. At least one concentrate capsule 110 (FIG. 6) is located within tube 108a, 108b between the plug and dialysis fluid container 100. Concentrate capsules 110 contain powdered or liquid concentrate for mixing with purified water to create dialysis fluid, provide a pH buffer or perform a diagnostic function. In an embodiment, a plurality of tubes 108a, 108b are provided, which each may carry one or more dialysis fluid constituent capsule, such as an electrolyte capsule and an osmotic agent along with other capsules if desired. The amount and concentration of the concentrate within capsules 100 is mixed with a certain volume of purified water to make a desired volume (e.g., fill volume of patient P) and type (per prescription of patient P) of dialysis fluid. The use of the concentrate capsules 110 enables dialysis fluid to be generated without the dialysis system 10 needing to be configured for determining precise measurements of concentrate, thereby saving dialysis machine costs. Instead, the concentrate capsules 110 are precisely formed at the time of manufacture to have a known quantity of concentrate.

As illustrated in detail below (not shown in FIG. 1), at least one actuator is provided, e.g., one for each tube 108a, 108b, which indexes an extender against the plug and at a desired time move the plug so as to push the plug so as to dislodge one or more concentrate capsule from tube 108a, 108b into dialysis fluid container 100. The one or more actuator may be mounted for example on holder 152. The actuator includes an indexer, such as a stepper motor, that under control or control unit 24 causes the extender to be indexed a precise amount to dislodge a desired one or more concentrate capsule 110 into dialysis fluid mixing container 100. Pump actuator 82 under control of control unit 24 may cycle the purified water and one or more concentrate capsule as it dissolves to help the concentrate to become mixed homogeneously.

In the illustrated embodiment, holder 152 includes a pressure sensor 160 positioned and arranged to sense a pressure of a fluid held within dialysis fluid mixing container 100. Pressure sensor 160 outputs to a control unit 24, which uses the sensed pressure to determine a head height of the dialysis fluid located within dialysis fluid container 100, which is constrained to have a certain shape by holder 152. The cross-sectional area of mixing container 100 is known accordingly, allowing control unit 24 to know a volume of dialysis fluid within dialysis fluid container 100. By subtracting volumes before and after a fill or drain of patient P, control unit 24 may determine an accurate amount of fresh dialysis fluid delivered to the patient or used dialysis fluid removed from the patient. By dividing intermediate volume differences by known time durations, control unit 24 may determine instantaneous, or virtually instantaneous, flowrate, and modify same if needed.

Dialysis fluid is pumped by pump actuator 82, which may be a tube or peristaltic pump actuator, through an inline heater 180. Heater 180 is in one embodiment an inductive heater, which heats the dialysis fluid from whatever temperature it is upstream of heater 180 (may have residual heat from distillation unit 12 and/or may be heated during mixing) to a desired body temperature, such as 37° C. Inductive heater 180 as discussed in detail below places one or more susceptors within one or more portion of a cylindrical heating tube 92, which are mounted for operation within an inductive coil 182 that extends around the one or more portion of the cylindrical heating tube in a non-contacting arrangement. Inductive heater 180 further includes power electronics that are in electrical communication with inductive coil 182 and are configured to supply an electrical current to the inductive coil, causing the susceptor to heat. The power electronics are under control of control unit 24 in one embodiment.

Heated dialysis fluid is delivered to patient P via pump actuator 82 and a self-priming patient connector 200. Self-priming patient connector 200 as illustrated in detail below includes a hydrophobic filter and a check valve. The hydrophobic filter is positioned adjacent to one more aperture formed in the housing. The check valve prevents air from entering the patient connector under atmospheric or negative pressure (e.g., during a drain of patient P). The check valve is opened under positive air pressure, e.g., while pump actuator 82 is pumping fresh dialysis fluid along patient line 94d, pushing air out of patient connector 200 via the at least one aperture and the hydrophobic filter, past the opened check valve. Self-venting patient connector 200 is provided initially with a seal at its outlet, which aids in forcing the air out through the at least one aperture and the hydrophobic filter. Once all air in patient line 94d has been purged, the pressure in self-venting patient connector 200 builds under liquid pumping pressure, rupturing the seal or causing a cutting member to pierce the seal. At this point, with patient line 94d fully primed, fresh, heated dialysis fluid may flow to patient P under positive pressure and used dialysis fluid may be removed from patient P under negative pressure. In the illustrated embodiment of FIG. 1, used dialysis fluid is returned to distillation unit 12 via return line 94e to be converted to purified water, e.g., WFI. In an alternative embodiment, used dialysis fluid is delivered via return line 94e instead to drain.

In addition to pump actuator 82, such as a peristaltic pump actuator, a dialysis fluid actuation assembly 80 of system 10 also includes valve actuators 84a to 84e, which may be electrically actuated solenoid pinch valve actuators (or motor driven bi-stable pinch valve actuators) that selectively pinch a fluid line closed or allow that fluid line to be open to allow flow. In an embodiment, valve actuators 84a to 84e are fail safe, such that upon a loss of power, the valves close automatically. FIG. 1 also illustrates that dialysis fluid actuation assembly 80 provides a patient fluid pressure sensor 86, which senses the pressure of fresh dialysis fluid being delivered to and used dialysis fluid being removed from patient P. As indicated by the dotted lines extending therefrom, each of pump actuator 82, valve actuators 84a to 84e, and patient fluid pressure sensor 86 are under control of, or output to, control unit 24. For example, control unit 24 may be programmed to receive feedback from patient fluid pressure sensor 86 to ensure that positive pressure provided by pump actuator 82 pumping fresh dialysis fluid to patient P, and negative pressure provided by pump actuator 82 removing used dialysis fluid from patient P, does not exceed positive and negative patient pressure limits, respectively.

A portion of the components of dialysis fluid actuation assembly 80 are housed within housing 20 along with the inline heater and components of distillation unit 12 discussed herein, while a portion of those components are presented on a surface of housing 20 for operation with a disposable unit 90. Disposable unit 90 includes (i) pumping line 92 that interfaces with an exposed portion of pump actuator 82, inline heater 180 and pressure sensor 86, (ii) a purified water, e.g., WFI, line 94a that interfaces with an exposed portion of valve 84a, (iii) a mixing container inlet/outlet line 94b that interfaces with an exposed portion of valve 84b, (iv) a mixing container inlet/outlet line 94c that interfaces with an exposed portion of valve 84c, (v) patient line 94d that interfaces with an exposed portion of valve 84d, and (vi) return line 94e that interfaces with an exposed portion of return valve 84e. Disposable set 90 also includes a mixing container 100 connected to mixing container inlet/outlet lines 94b and 94c. Disposable set 90 further includes a self-priming patient connector 200 located at a distal end of patient line 94d.

Distillation Unit

Figure 2:
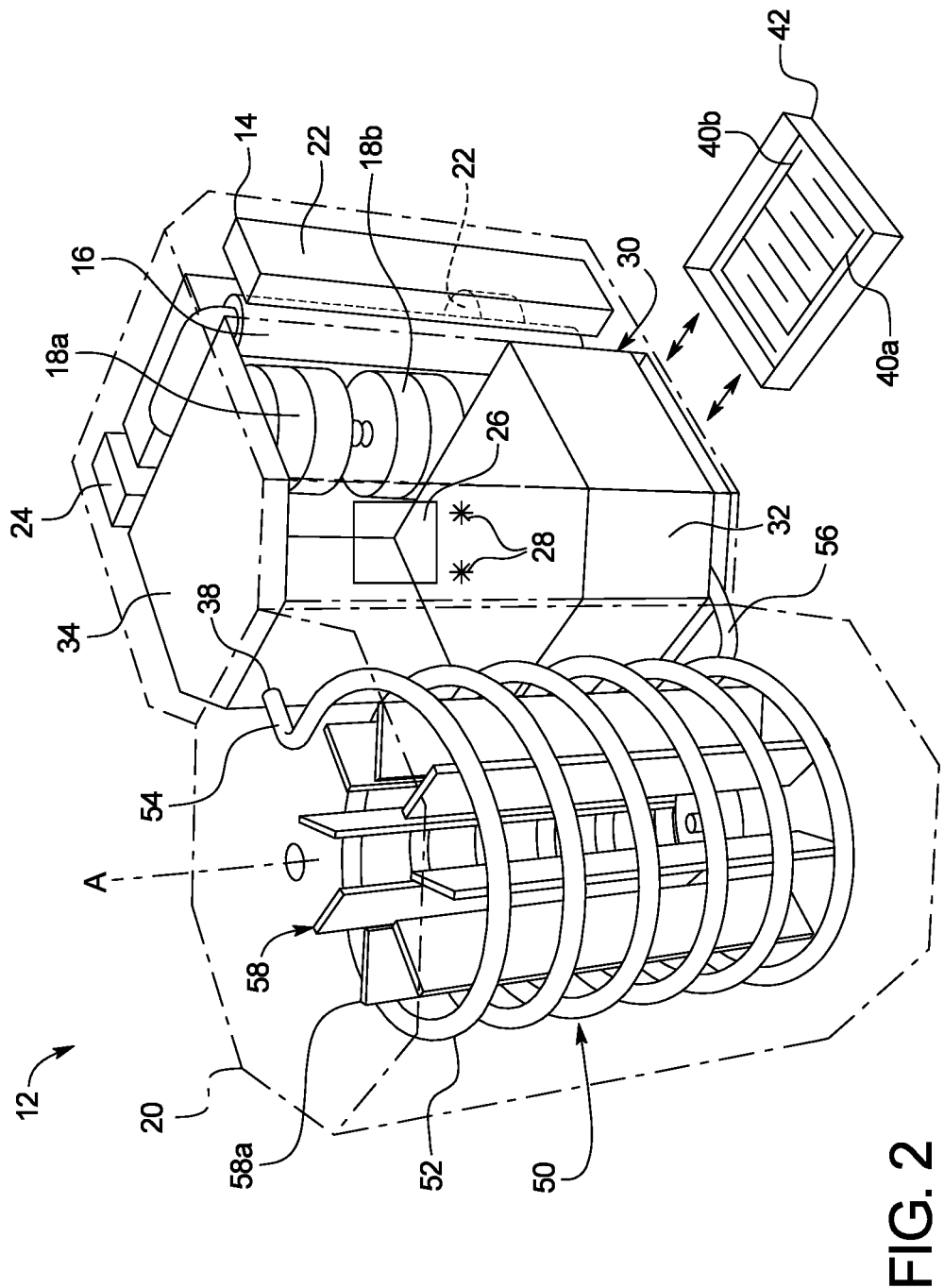
FIG. 2 is a perspective view of one embodiment of a purified water generation unit or distillation unit of the present disclosure, which may be used in the overall system.
Figure 3:
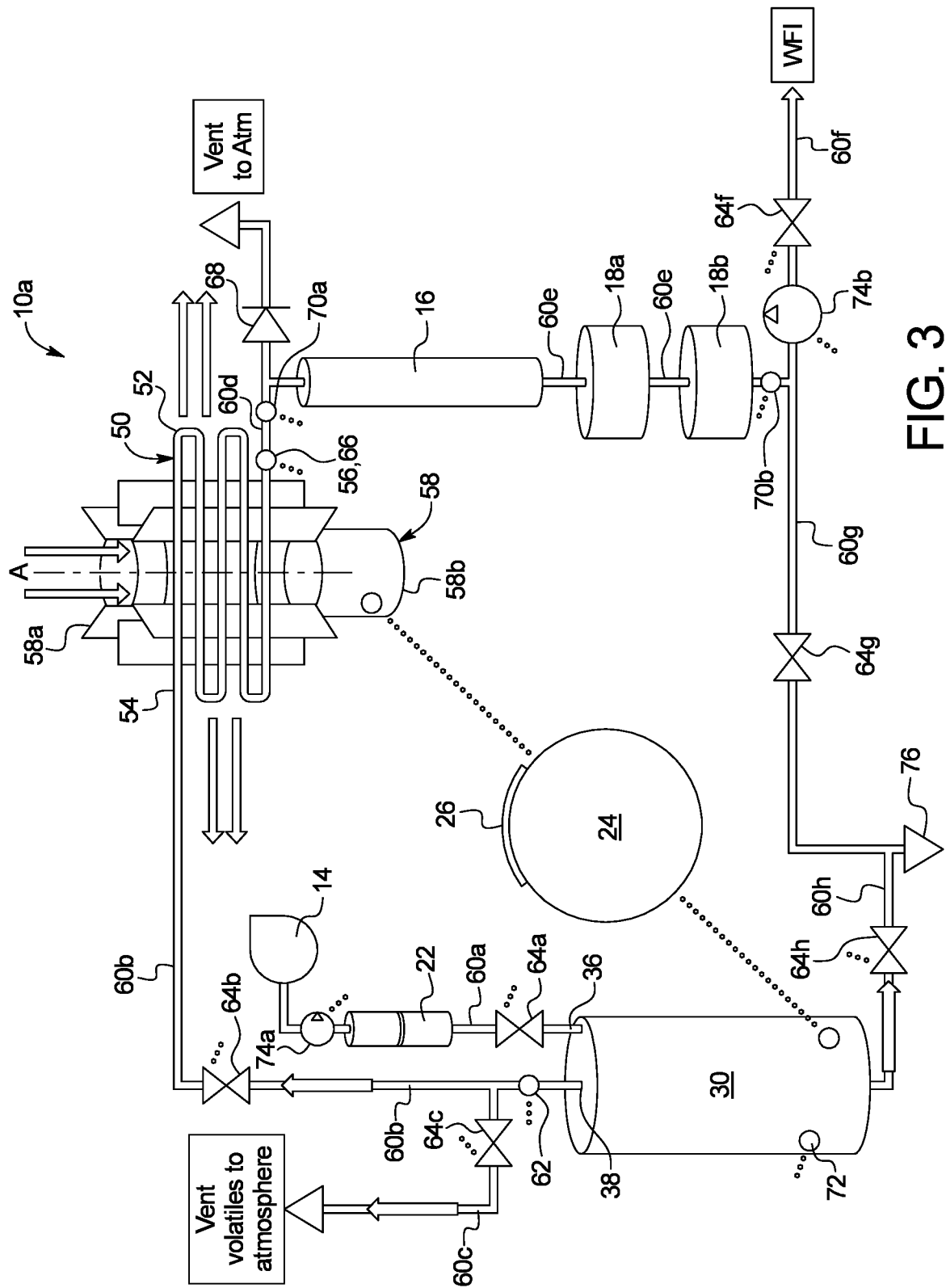
FIG. 3 is a schematic view of a purified water generation unit or distillation unit showing one embodiment of an overall flowpath, sensing, valving, optional pumping and control arrangement.
Figure 4:
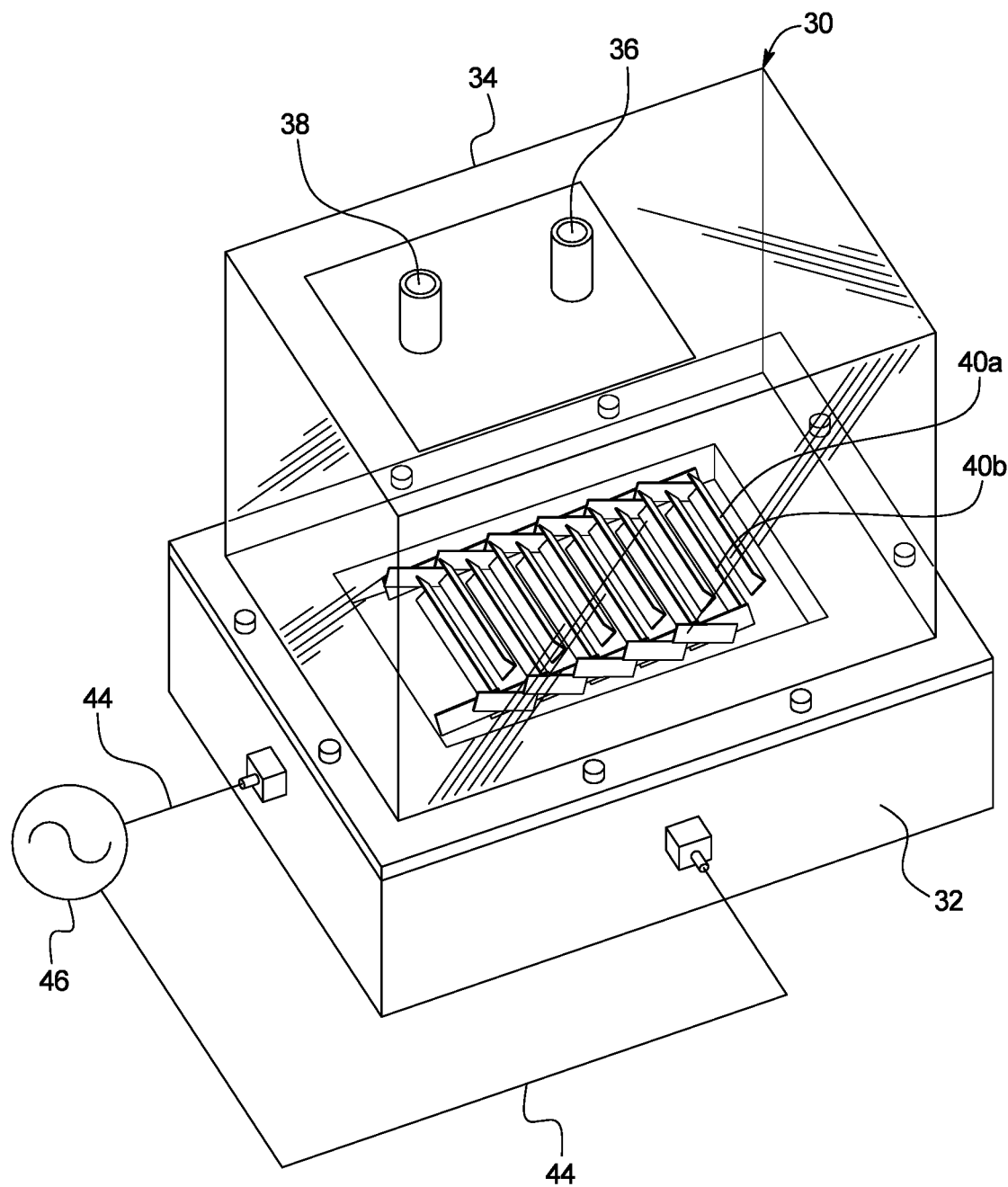
FIG. 4 is a perspective view of one embodiment of a heater for the purified water generation unit or distillation unit of the present disclosure and one possible electrical arrangement for same.

Referring now to FIGS. 2 to 4, a distillation unit 12 configured to produce purified water, e.g., WFI, is illustrated in further detail. The primary components of water distillation unit 12 may include a water (or used dialysis fluid) tank 14 for receiving tap water (or used dialysis fluid) or other unpurified water by hand or via house water pressure, a heater 30 for boiling the unpurified water to create steam, and a condenser 50 to cool the steam to produce highly purified water, wherein impurities from the water are vented and/or collected at the bottom of heater 30 and delivered to drain. In an alternative embodiment, tap water tank 14 is not provided and tap water is instead delivered to heater 30 directly via house water pressure.

One or more type of finishing (polishing and/or sterilizing) filter 16, 18a/18b may be located downstream from condenser 50, such as, an electrodionization ("EDI") filter (or a de-ionization resin filter) 16 and/or one or more ultrafilter 18a and 18b. The downstream finishing filter(s) in an embodiment further purifies the water exiting condenser 50 from a level of pure or ultrapure to being water for injection ("WFI") or of an injectable quality, which is suitable for use to form either peritoneal dialysis ("PD") fluid or a replacement fluid for a blood treatment therapy, such as hemofiltration ("HF") or hemodiafiltration ("HDF").

Optionally, a carbon filter 22 may be placed along unpurified water line 60a between water tank 14 (or house water connection) and heater 30 to remove chloramines from the tap water prior to reaching the heater. Additionally, a pressure sensor 62 may be located so as to sense pressure in a steam line 60b located between heater 30 and condenser 50. A vent line 60c may be located downstream from pressure sensor 62. Valves 64b and 64c may be placed respectively in steam line 60b and vent line 60c to selectively allow an overpressure in the steam line to be vented to atmosphere and/or volatiles that are freed from the heated water to be vented to atmosphere.

A temperature sensor 66 is located along condenser exit or purified water line 60d in one embodiment so as to sense the temperature of the purified water exiting condenser 50 to ensure that the water is safe to be delivered to the point of use, e.g., a mixing location to be combined with concentrates to form a dialysis fluid. A pressure relief valve 68 is also located along purified water line 60d in an embodiment to relieve excess pressure in the purified water prior to reaching at least one finishing filter 16, 18a/18b, if provided, or to the point of use if the at least one finishing filter is not provided. The pressure relief valve 68 may be provided for safety (e.g., may be optional) since typically energy input into the heater 30 is balanced by a capacity of the condenser 50 so that nearly all steam is condensed into the water as the water flows to the purified water line 60d.

Water distillation or purification unit 12 may also include multiple conductivity sensors, such as a first conductivity sensor 70a located adjacent to the temperature sensor 66 in purified water line 60*d* and a second conductivity sensor 70*b* located in sterilizing line 60*e* just prior to the exit of the WFI from water distillation unit 12 via WFI valve 64*f* located along WFI line 60*f*, e.g., just downstream from at least one finishing filter 16, 18*a*/18*b*. A bypass line 60*g* branches off of WFI line 60*f* (or purified water line 60*d*) and extends to a drain 76. An impurities removal valve 64*h* is located to selectively open and close impurities removal line 60*h* to drain 76. In some embodiments, a separate drain may be fluidly coupled to the impurities removal line 60*h* to provide fluid isolation from the bypass line 60*g*. The separation of the lines 60*g* and 60*h* may prevent bacteria or mold from inadvertently reaching purified water.

FIG. 3 illustrates that a water level sensor 72 may be located in thermally insulative base 32 of heater 30 to detect how much unpurified water or used dialysis fluid has been introduced via unpurified water valve 64*a* and/or to provide a low level detection for when more unpurified water needs to be filled via water valve 64*a*. To that end, multiple water level sensors 72, e.g., high and low sensors, may be provided.

It is contemplated for distillation unit 12 to provide at least one pump if needed, such as an unpurified water pump 74*a* only, a purified water pump 74*b* only, or both pumps 74*a* and 74*b*. Pumps 74*a* may be gear pumps or other types of electromechanical pumps, e.g., where unpurified water line 60*a* is non-disposable, e.g., stainless steel. If unpurified water line 60*a* and/or WFI line 60*f* are instead made of disposable tubing or as part of a disposable cassette, pumps 74*a* and 74*b* may instead be peristaltic pumps or pneumatically or electromechanically actuated, volumetric cassette sheeting pumps. In any case, downstream pump 74*b* may provide a sterilized interface for use with the purified water, e.g., peristaltic pumps or pneumatically or electromechanically actuated, volumetric cassette sheeting pumps.

In some embodiments, the unpurified water pump 74*a* and/or the purified water pump 74*b* may be omitted since pressure from boiling water in the heater 30 causes the water vapor to flow to the condenser 50. The control unit 24 may be configured to balance input power to the heater 30 with a condensation rate of the condenser 50 to maintain a desired pressure to produce a desired flow rate of water. While this approach may use more power for the heater 30 to reach a desired pressure, it is offset from not having the unpurified water pump 74*a* and/or the purified water pump 74*b*.

As indicated by the dotted lines extending therefrom, each of the heater 30, condenser 50, pressure sensor 62, valves 64*a* to 64*c* and 64*f* to 64*h*, temperature sensor 66 and conductivity sensors 70*a* and 70*b* may be under microprocessor control of the control unit 24 for overall system 10, which may include one or more processor and one or more memory. In an embodiment, control unit 24 includes a user interface 26 having a display device under control of a video controller in communication with the at least one processor and the at least one memory. One or more speaker 28 is provided to output sounds, e.g., alarms or voice guidance to the user. Control unit 24 determines when purified water, e.g., WFI, is needed and, for example, how much (e.g., data concerning demand). In an embodiment, control unit 24 also controls the temperature of the purified water, e.g., WFI that is outputted. In this manner, distillation unit 12 may lessen the burden on the inline heater described herein.

In one embodiment, the water is heated by applying a large AC electrical potential to a pair of electrodes 40*a* and 40*b*, which are submerged in the tap water or used dialysis fluid, wherein the electrodes are separated from each other such that current has to pass through the tap water to complete an electrical circuit. Electrodes 40*a* and 40*b* are made of a medically compatible and at least somewhat electrically conductive material, such as stainless steel (e.g., 304, 316, or 316L) or titanium. Electrodes 40*a* and 40*b*, in an embodiment, each include baffles that are interleaved within baffles of the other electrode, so as to increase the overall surface area of adjacently juxtaposed electrode material. A combination of a surface area of the electrodes 40*a* and 40*b* and a distance between the electrodes 40*a* and 40*b* determines a resistance of the water therebetween. A conductivity of the water may also affect the resistance. The control unit 24 may vary the amount of power applied to the electrodes 40*a* and 40*b* to compensate for the resistance of the water. The spacing and surface area of the electrodes 40*a* and 40*b* accommodate an expected feed water conductivity and a range of power that can be applied to enable the heater 30 to meet water generation requirements of the system 10.

In another embodiment, the water is heated using inductive heating. In this embodiment, a non-disposable stainless steel metal plate is inductively heated. The metal plate is placed inside of a disposable heating chamber.

As illustrated in FIG. 2, heater 30 in one embodiment includes an electrically and thermally insulative removeable and disposable tray or liner 42 fitted into a rigid base 32, into which disposable electrodes 40*a* and 40*b* are placed and held fixed in a non-contacting relationship. FIG. 4 illustrates that electrical leads 44 are inserted sealingly through a wall of base 32 and are placed into electrical communication with electrodes 40*a* and 40*b*. Electrical leads 44 are connected to a power source 46, which for example is configured to apply 1000 to 2000 Watts of power to electrical leads 44 and therefore to electrodes 40*a* and 40*b* and tap water or used dialysis fluid located between the electrodes.

A cover 34, e.g., an electrically and thermally insulative cover, is removeably, e.g., hingedly, connected to base 32, such that cover 34 allows access to the disposable liner and electrodes for replacement. Cover 34 in one embodiment provides two ports, one port 36 for connection to a water source 14 (tank or tap water directly) via unpurified water line 60*a*, and another port 38 for connection to a steam line 60*b*, which carries steam from heater 30 to condenser 50.

As is known, the process of distillation involves separating components or substances, in the present case volatiles, from a liquid, in one example tap water and in another example used dialysis fluid, using selective boiling and condensation. The volatiles of the present distillation process are either collected at the bottom of base 32 of heater 30 and discharged intermittently from heater 30 to a drain 76 via an impurities valve 64*h* and impurities line 60*h*, are removed via disposable tray or liner 42, and/or are vented through a vent in a vent line 60*c* extending from the top of heater 30. It has been found that the more volatile substances are vented to the atmosphere, while the least volatile substances are flushed to the drain or removed via disposable tray or liner 42. Water is of intermediate volatility. The most volatile substances boil first and the resultant gas is vented. Water boils next and the resulting gas (steam) is condensed back into liquid. The least volatile parts (including some water) never boil and are flushed to drain or removed via the disposable instead.

In one embodiment, condenser 50 includes a condensing coil 52, which is made of a thermally conductive and medically safe material, such as stainless steel (e.g., 304, 316, or 316L) or titanium. Plural heat fins (not illustrated), such as highly thermally conductive copper heat fins, are attached to coil 52, e.g., via soldering, welding, brazing, gluing and/or mechanical connection. The heat fins conduct heat away from coil 52 and the steam located within the coil. The coil includes an inlet 54 and an outlet 56, wherein inlet 54 is located at the top of coil 52 and outlet 56 is located at the bottom of coil 52 in the illustrated embodiment. In this manner, steam from heater 30 enters inlet 54 at the top of coil 52, while highly purified water exits outlet 56 at the bottom of coil 52.

The condenser also includes a fan 58, which is located inside of coil 52 and associated heat fins. Fan 58 in an embodiment has upper and lower fan blade holders (not illustrated) that are attached respectively to upper and lower fixtures via bearings (not illustrated), such as ball bearings. The upper and lower fan blade holders spin around a vertical axis of rotation A extending through the centers of each of the bearings. Multiple blades 58a of fan 58 are in an embodiment vertically disposed paddles or baffles that are formed with (e.g., as a single molded piece) or are connected to the upper and lower fan blade holders so as to extend radially from the vertical axis of rotation A. The upper and lower bearings are placed in a rotationally fixed relationship with upper and lower fixtures, so as to hold fan blades 58a firmly in place but allow the blades to spin freely about the central, vertical axis A of fan 58. In an alternative embodiment, fan blades 58a may be held fixed to a vertical shaft (not illustrated) that extends along and spins around the length of the central, vertical axis of rotation A.

The output shaft of a fan motor 58b is coupled via a direct coupler, or via a geared or belt and pulley relationship as desired (not illustrated), to one of the fan blade holders. In operation, the fan motor 58b, under control of control unit 24 for dialysis system 10 causes the coupled fan blade holder, blades 58a connected to the coupled holder, and an opposing holder holding the other end of fan blades 58a to spin. The spinning of blades 58a pulls air in from above and below and drives air radially outwardly and over the copper heat fins connected to condenser coil 52, causing convective heat transfer away from the steam traveling through condenser coil 52.

In an embodiment, control unit 24 of dialysis system 10 is configured to receive a desired purified water exit temperature from the user or a patient's prescription. Control unit 24 in turn accesses a look-up table or algorithm that correlates the purified water exit temperature with the speed of fan 58 and boiler power of heater 30. Control unit 24 in turn sets the boiler power and fan speed to be the correlated boiler power and fan speed for the desired water exit temperature. In this embodiment, fan motor 58b of fan 58 is a variable speed motor and the boiler power of heater 30 is variable. Providing purified water, e.g., WFI, at a temperature elevated above ambient is advantageous for PD or blood treatment applications, which require the resulting mixed dialysis fluid to be at or near body temperature, e.g., 37° C., as discussed herein for the inductive heater. Here, heating energy required by the inductive heater is conserved.

In an alternative embodiment, fan motor 58b is a single speed motor and the outlet temperature at condenser 50 for the purified water is whatever temperature is achieved via the single speed. It is contemplated in alternative embodiments to provide other types of cooling for the condensing operation, such as water cooling. For example, if tap water or used dialysis fluid storage tank 14 is provided, it is contemplated to place condensing coil 52, e.g., without heat fins, which may again be made from a medically safe material, such as, stainless steel (e.g., 304, 316) or titanium, into tank 14 to (i) cool the steam from heater 30 and (ii) preheat the tap water so that power usage by heater 30 is reduced. Here, control unit 24 is programmed to make sure enough tap water is present in tank 14 to adequately cool condensing coil 52, even if some of the tap water is not eventually purified and is provided instead only for cooling. Multiple water cooled heat exchangers may also be provided if desired to help condense the steam.

FIGS. 1 and 2 illustrate that distillation unit 12 is housed within a housing 20, which may be made of plastic, metal or combinations thereof. It should be appreciated that housing 20 may additionally house or support any of reusable structures described herein, such as holder 152 for volume determination, pump actuator 82, and the inductive coil 182 of the inductive heater 180. Housing 20 as illustrated houses control unit 24 and provides a location for mounting user interface 26 and speakers 58.

Additional information regarding distillation unit 12 may be found in U.S. provisional patent application No. 62/967,129, entitled "Medical Fluid Therapy System And Method Employing Distillation", filed contemporaneously with the present disclosure, the entire contents of which are incorporated herein by reference and relied upon.

Dialysis Fluid Preparation

Figure 5:
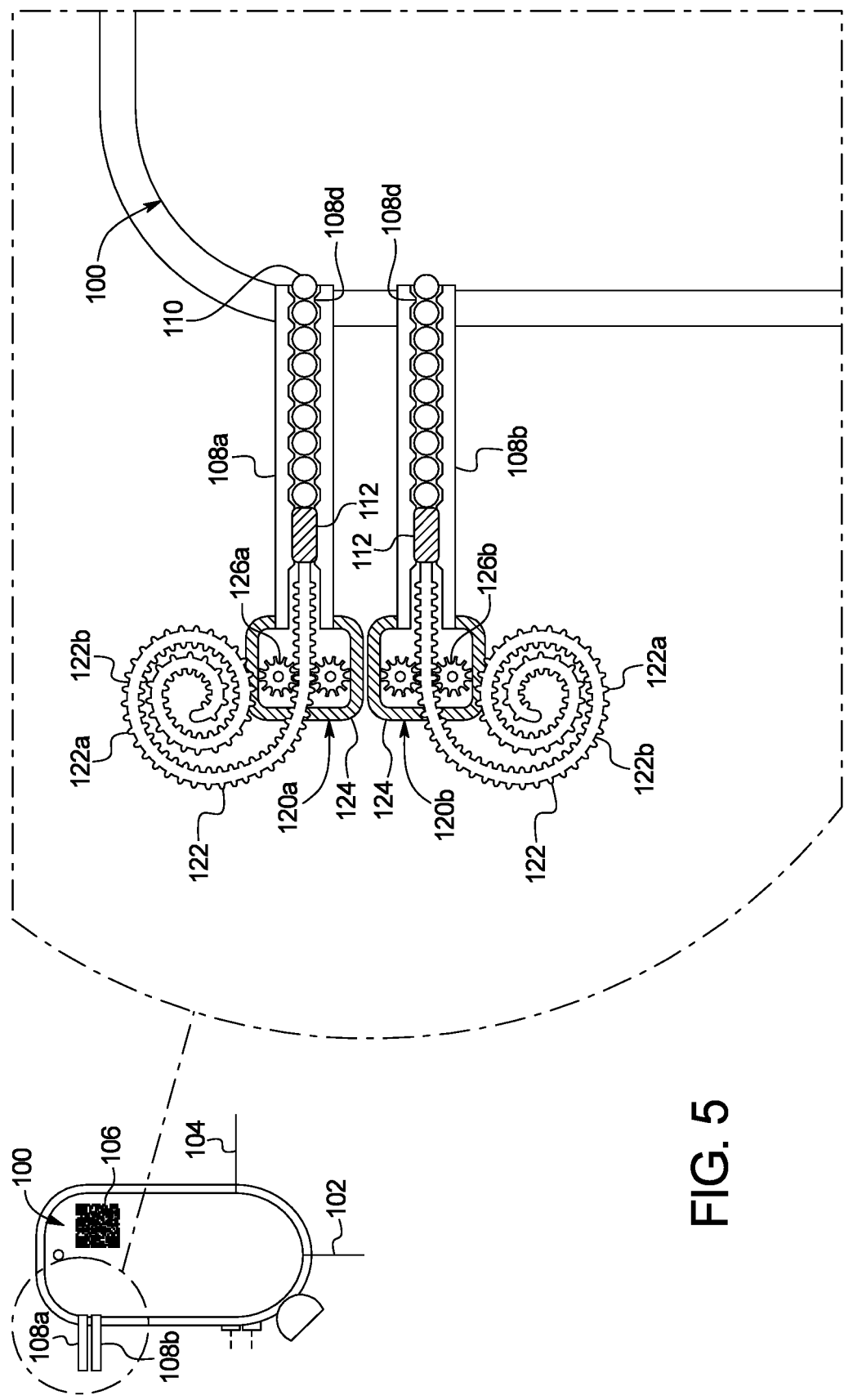
FIG. 5 is a sectioned view illustrating one embodiment of a concentrate dispensing subsystem and associated methodology of the present disclosure.

Referring now to FIGS. 1 and 5, a pump of distillation unit 12, such as purified water pump 74b, with valves 84a and 84b open and all other valves closed, pumps purified water, e.g., WFI, through purified water line 94a and mixing container inlet/outlet line 94b to vertically disposed and sterilized container or bag 100 located within a vertically disposed clamshell holder 152 discussed in detail below. Alternatively, if distillation unit 12 is not provided with a pump, or perhaps only with unpurified water pump 74a, purified water, e.g., WFI, may instead be pumped by system pump actuator 82, with valves 84a and 84c open and all other valves closed, through purified water line 94a, pumping line 92, and mixing container inlet/outlet line 94c to mixing container or bag 100. Mixing container or bag 100 in FIG. 5 is accordingly illustrated as having a first inlet/outlet port 102 and a second inlet/outlet port 104. Ports 102 and 104 may each be used as an inlet or an outlet port, or perhaps only a single port 102 or 104 is provided, which is used as both an inlet and an outlet port.

FIGS. 1 and 5 illustrate that mixing container or bag 100 may be provided with an identifier 106, e.g., a barcode, 2D barcode, QR code or other marking that may be read by a scanner, e.g., a camera or reader. In an embodiment, the reader is a camera provided by patient P's (or caregiver's) smartphone 98 as part of an application ("app") that is used to begin and track a treatment. Control unit 24 in an embodiment includes a wireless transceiver that communicates wirelessly with the user's smartphone 98 to exchange information with the dialysis treatment app. In an embodiment, the user opens the dialysis treatment app, which prompts the user to scan identifier 106, which scan is read and converted by the app into information for sending wirelessly to control unit 24 of system 10. In an embodiment, the app also prompts patient P or caregiver to enter whether the patient is currently full of dialysis fluid, the answer to which is sent to control unit 24, so that the control unit may know whether or not to begin treatment with a drain, and if so, to know how much tap water, if any, needs to be added to tank 14 of distillation unit 12.

In an embodiment, the information transferred from identifier 106, to the app, to control unit 24 includes all information needed for treatment, including but not limited to: (i) number of patient fills, (ii) volume per fill, (iii) number of patient drains (may be different than number of patient fills if the last fill is to remain with patient P after disconnecting from disposable set 90), (iii) solution type, e.g., dextrose or glucose level, for each fill, and (iv) dwell time following each patient fill. In an embodiment, control unit 24 knows the prescription, or perhaps multiple approved prescriptions for patient P and analyzes the above information (including concentrate contents) to make sure it falls under or complies with at least one of patient P's prescriptions, such that if it is attempted to use a non-approved container 100, control unit 24 causes user interface 26 and/or speakers 28 to alarm and prevent treatment from proceeding until a proper container 100 is loaded and scanned. Similarly, the information provided by identifier 106 may include the identification of the particular mixing container 100, such that if it is attempted to use the same container 100 a second time, which no longer contains concentrate, control unit 24 will cause user interface 26 and/or speakers 28 to alarm and prevent treatment from proceeding until a new container 100 is loaded and scanned.

In case the patient or caregiver does not have or is not comfortable with using a smartphone, it is contemplated to also provide the scanner as part of user interface 26 at housing 20, to which the user presses identifier 106 of mixing container 100, which is empty of fluid. Here, the app is not necessary. User interface 26 is alternatively a wireless smart device, such as a tablet. In any embodiment for user interface, the information discussed above is obtained by control unit 24 from identifier 106.

At least some of the information provided above corresponds to the concentrates provided with mixing container 100. As illustrated in FIGS. 1 and 5, sterilized mixing container or bag 100 is provided with one or more sterilized tube 108a, 108b that is preloaded with one or more concentrate capsule 110. A slideable plug 112, e.g., rubber plug, is located at a distal end of each sterilized tube 108a, 108b. Plug 112 is fitted in an airtight manner within each tube 108a, 108b, so as to maintain the sterility of the bag, tube and concentrate capsules. Although not illustrated, a tear away cap may be proved at the distal end of each tube 108a, 108b, for transport and to ensure sterility prior to use.

In the illustrated embodiment, slideable plugs 112, concentrate capsules 110, and tubes 108a, 108b are sized so that plugs 112 and capsules 110 are held press-fittingly within tubes 108a, 108b, so that neither the plugs nor the capsules move until a plug 112 is acted upon as discussed below. The press-fitting of capsules 110 is enough to hold the capsules in place regardless of the orientation of mixing container 100. In an alternative embodiment, a thin rupturable seal (not illustrated) may be formed or fitted within each tube 108a, 108b, capturing and holding concentrate capsules 110 between plug 112 and the seal prior to use.

Figure 6:
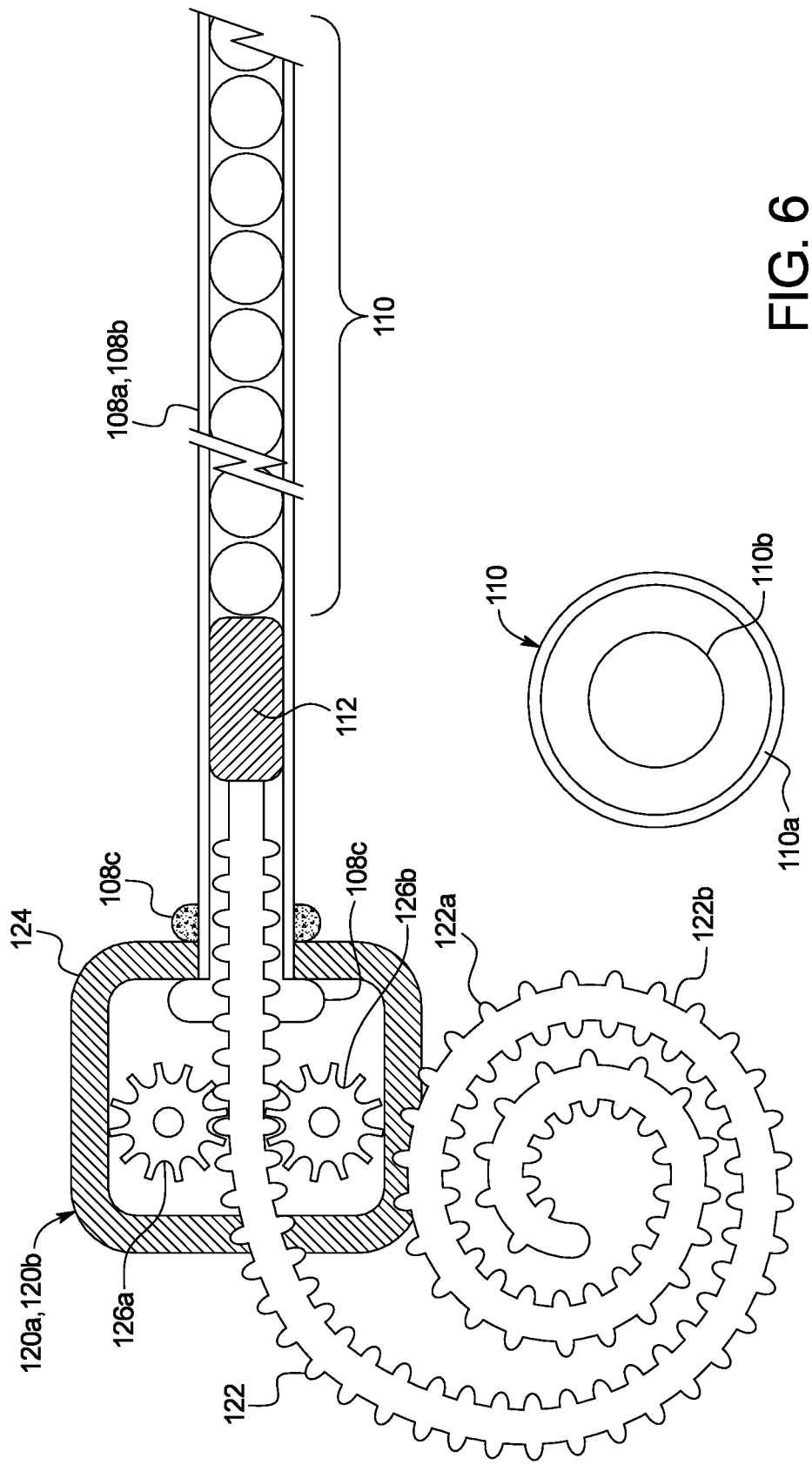
FIG. 6 is a front elevation view of one embodiment of a dispensing actuator of the subsystem of the present disclosure.

As illustrated in FIGS. 5 and 6, housing 20 of dialysis system 10, e.g., at clamshell holder 152, provides dispensing actuators 120a, 120b, for example, a dispensing actuator 120a, 120b for each concentrate capsule containing tube 108a, 108b. In FIG. 5, when the user loads sterilized mixing container 100 having concentrate tubes 108a, 108b into clamshell holder 152, the user also connects the end of each concentrate tube 108a, 108b with one of the dispensing actuators 120a, 120b. In the illustrated embodiment of FIG. 5, the user inserts each concentrate tube 108a, 108b over an extender 122 located within each dispensing actuator 120a, 120b, so that slideable plug 112 within each concentrate tube 108a, 108b is abutted against one of the ends of the extender 122a, 122b.

FIG. 6 illustrates an alternative embodiment, in which a portion of dispensing actuators 120a, 120b is disposable.

Here, capsule containing tubes 108a, 108b are each provided with a distal flange 108c that is press-fitted onto a disposable housing 124. Disposable housing 124 holds extender 122, which is likewise disposable.

In either FIG. 5 in which extender 122 is reusable or FIG. 6 in which extender 122 is disposable, the extender includes gear teeth 122a extending from a stem 122b in one embodiment. Gear teeth 122a mesh with mating teeth of one or more driver or rotating gear 126a, 126b located within each dispensing actuator dispensing actuators 120a, 120b. In FIG. 5, one or more driver or rotating gear 126a, 126b is reusable, while in FIG. 6, one or more rotating gear 126a, 126b is disposable. In either case, one or more driver or rotating gear 126a, 126b is driven by an indexer, for example, a stepper motor, which indexes extender 122 over short and precise distances to in turn translate plug 112 within the sterilized concentrate tubes 108a, 108b a short distance, which dispenses one or more concentrate capsule 110 into the WFI, which has been pumped into sterilized mixing container 100.

Figure 7:
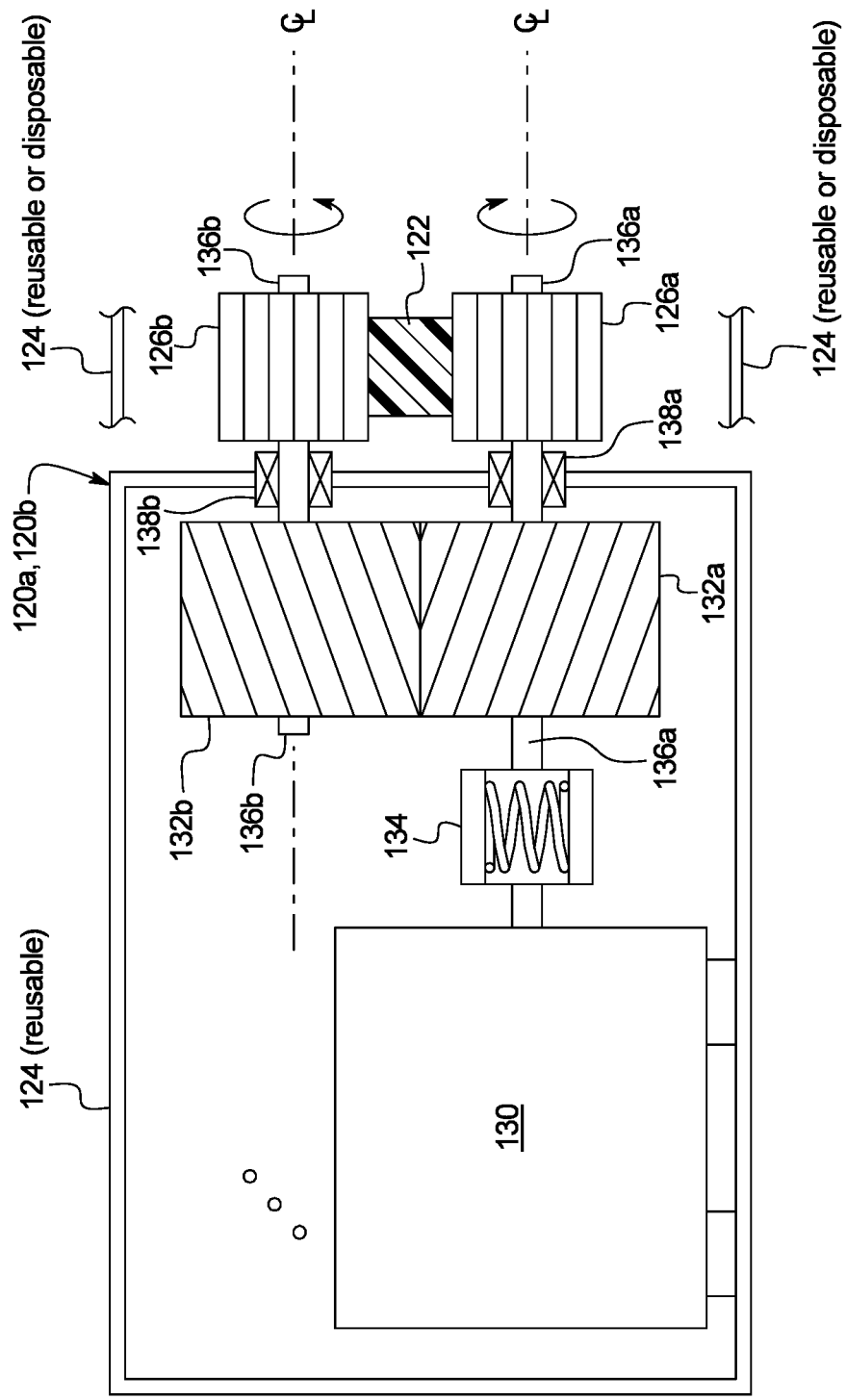
FIG. 7 is a side-sectioned elevation view of the dispensing actuator of the subsystem of the present disclosure.

FIG. 7 illustrates an embodiment in which a single indexer 130, e.g., a stepper motor, turns both rotating gears 126a, 126b in opposite directions to advance extender 122 in a desired direction. Indexer 130 is under control of control unit 24 as indicated by the dotted line extending from the indexer. FIG. 7 also illustrates that a third gear 132a and a fourth gear 132b are provided, which may be worm gears that are in geared or meshed relationship with each other. In an embodiment, third gear 132a and fourth gear 132b are reusable.

Indexer or stepper motor is coupled via a coupler 134, e.g., a spring-loaded coupler to increase accuracy, to a shaft holding one of third gear 132a or fourth gear 132b, here a shaft 136a holding third gear 132a and gear 126a. A second shaft 136b holds both fourth gear 132b and gear 126b. Driver or gears 126a and 126b are illustrated as holding extender 122, shown in cross-section, which is located within housing 124. Shafts 136a and 136b each extend through a wall of housing 124 and are be held in place with respect to housing 124 via a pair reusable ball bearings 138a and 138b mounted to housing 124 at a desired spaced apart distance, and which provide apertures through which shafts 136a and 136b extend. In the reusable embodiment of FIGS. 5 and 7, control unit 24 is programmed to retract extenders 122 from tubes 108a, 108b after treatment to a starting position for the next treatment. Here, indexer 130 is driveable in two directions.

In the embodiment in which housing 124, drivers or gears 126a and 126b, and extender 122 are disposable, i.e., for FIG. 6, shafts 136a and 136b are broken (e.g., to the right of bearings 138a and 138b) into reusable and disposable sections, which are translated together upon the user installing mixing container 100 and disposable set 90 for treatment. The reusable and disposable sections of shafts 136a and 136b may have mating male and female sawteeth connectors that slide together to transfer torque during operation. In the disposable embodiment of FIGS. 6 and 7, housing 124, drivers or gears 126a and 126b, and extender 122 are discarded after treatment.

In a further alternative embodiment, worm gears 132a and 132b in FIG. 7 are not provided. Shaft 136b held by bearing 138b is still provided and mounts driver or gear 126b for rotatable operation with extender 122. Here, gear 126b is not driven and follows the movement of extender 122, but nonetheless forces extender 122 against driven gear 126a, which is still held in position by bearing 138a, which accepts shaft 136a extending to motor coupler 134.

Regardless of whether the embodiment of FIG. 5 or 6 is used, it is contemplated for control unit 24 to provide a current or torque monitor that provides a signal indicative of whether plug 112 is fully abutted against the most distal concentrate capsule 110 when mixing is to commence. Pushing plug 112 concentrate capsules 110 through concentrate tubes 108*a*, 108*b* should require a measurably higher torque and currant than pushing plug 112 alone. Control unit 24 is programmed accordingly in one embodiment to look for the higher motor current prior to starting the indexing sequence. To aid the indexing sequence, it is contemplated to provide an annular flap or protrusion 108*d* (FIGS. 5 and 6) at the proximal end of concentrate tubes 108*a*, 108*b*, which serves to hold concentrate capsules 110 in place prior to mixing and to provide a current spike as each capsule is pushed past the annular flap or protrusion 108*d* and into the WFI for mixing.

Control unit 24 of dialysis system 10 is programmed to cause the stepper motor or other indexer 130 to index extenders 122 a preset distance one or more time during treatment to mix one or more supply of fresh dialysis fluid. Each index may cause one or more concentrate capsule 110 to be delivered to the WFI. As mentioned above, multiple dispensing actuators 120*a*, 120*b* may be provided, e.g., one for indexing electrolyte capsules 110 and another for indexing osmotic agent capsules 110. The two actuators 120*a*, 120*b* may also be used to dispense other types of capsules 110, such as pH buffers and diagnostic agents. Or, additional actuators 120*c* to 120*n* may be provided to dispense additional capsules 110.

As illustrated in FIG. 6, concentrate capsules 110 may include an outer gel coating 110*a* forming a sphere or spherocylinder (cylinder with semispherical ends). The gel coating may hold a powder or liquid concentrate 110*b* depending on the type of concentrate. The powder or liquid may have a highest possible concentration so that capsule 110 is as small as possible. The quantity and concentration of powdered or liquid concentrate 110*b* are selected to as to be mixed with a known volume of WFI located within the sterile mixing container 100 held by the clamshell holder 152 to form a desired dialysis fluid when fully mixed, e.g., a 1.5%, 2.5% or 4.25% dextrose PD solution.

Referring again to FIG. 1, control unit 24 of system 10 may be configured to perform the following three-part mixing sequence: (i) partially fill mixing container 100 with WFI by (a) opening valves 84*a* and 84*b*, and with all other valves closed, using purified water pump 74*b* of distillation unit 12 to pump a first programmed amount of WFI into mixing container 100 or (b) opening valves 84*a* and 84*c*, and with all other valves closed, using system pump actuator 82 to pump a first programmed amount of WFI into mixing container 100; (ii) index extenders 122 of dispensing actuators 120*a*, 120*b* so as to push a programmed amount and type of concentrate capsules 110 into the first programmed amount of WFI held within mixing container 100, and with valves 84*b* and 84*c* open, and with all other valves closed, using system pump actuator 82 to vigorously recirculate the WFI and the dry or liquid concentrate from capsules 110, while heating the ongoing mixture to, e.g., 37° C. to dissolve coatings 110*a* of capsules 110; and (iii) fill mixing container 100 with the remainder of the designated volume of WFI by (a) opening valves 84*a* and 84*b*, and with all other valves closed, using purified water pump 74*b* of distillation unit 12 to pump a second programmed amount of WFI into mixing container 100 or (b) opening valves 84*a* and 84*c*, and with all other valves closed, using system pump actuator 82 to pump a second programmed amount of WFI into mixing container 100, wherein the cool WFI brings the resulting dialysis fluid temperature to below, but perhaps near, 37° C. As discussed above, distillation unit 12 may output heated purified water, e.g., WFI, such that heating during the recirculation in (ii) above can be minimized. The control unit 24 performs the above-operations by ensuring the mixture temperature in the container 100 is optimal for mixing/dissolving and not too high, which could damage the concentrates. The control unit 24 may set a temperature of the mixture to slightly higher than 37° C. such that the addition of cooler WFI (e.g., the second programmed amount of WFI) to the container 100 causes the mixture to cool to the ~37° C. target temperature.

It is contemplated for control unit 24 during the recirculation in (ii) above to cause system pump actuator 82 to reverse direction at least one time. Also, it is possible that concentrate capsules 110 are larger than the inner diameters of mixing container inlet/outlet lines 94*b* and 94*c*, so that the capsules fall to the bottom of mixing container 100 rather than potentially clogging one of the lines. As coatings 110*a* dissolve, powder or liquid concentrates 110*b* are swept away by the WFI moving upwardly through inlet/outlet port 102, carried through mixing container 100, and recirculated through the tubing including pumping line 92.

As discussed above, proportioning of WFI and concentrate is performed on a volumetric basis, that is, providing the WFI and each needed concentrate in a predefined ratio to arrive at a desired dialysis fluid, e.g., 1.5%, 2.5% or 4.25% dextrose PD solution. It is also contemplated to confirm that the dialysis fluid has been mixed properly by comparing its conductivity to a known conductivity for the desired dialysis fluid. To this end, it is contemplated to pump a sample of the mixed dialysis fluid past one of the conductivity sensors of distillation unit 12, e.g., downstream conductivity sensor 70*b* using purified water pump 74*b*, after which the sample is sent to drain 76 or tank 14 of distillation unit 12. If the sample is bad the test may be repeated, and if the samples continuously fail, the entire batch within mixing container 100 may be delivered to drain 76 or tank 14 for reprocessing, all under control of control unit 24.

As mentioned above, it is contemplated to provide one or more diagnostic capsule 110, which may be stored as the last capsule in an electrolyte or osmotic agent tube 108*a* or 108*b* (or in a separate tube), and which is inserted into a known amount of effluent or used dialysis pumped via pump actuator 82 from patient P into mixing container 100. It is contemplated to let diagnostic capsule 110 dissolve into the effluent, after which patient P in one embodiment brings the effluent bag to a clinic for analysis. In some instances, a diagnostic capsule 110 may be dispensed after every drain for collection of additional effluent data over multiple dialysis cycles.

Figure 8:
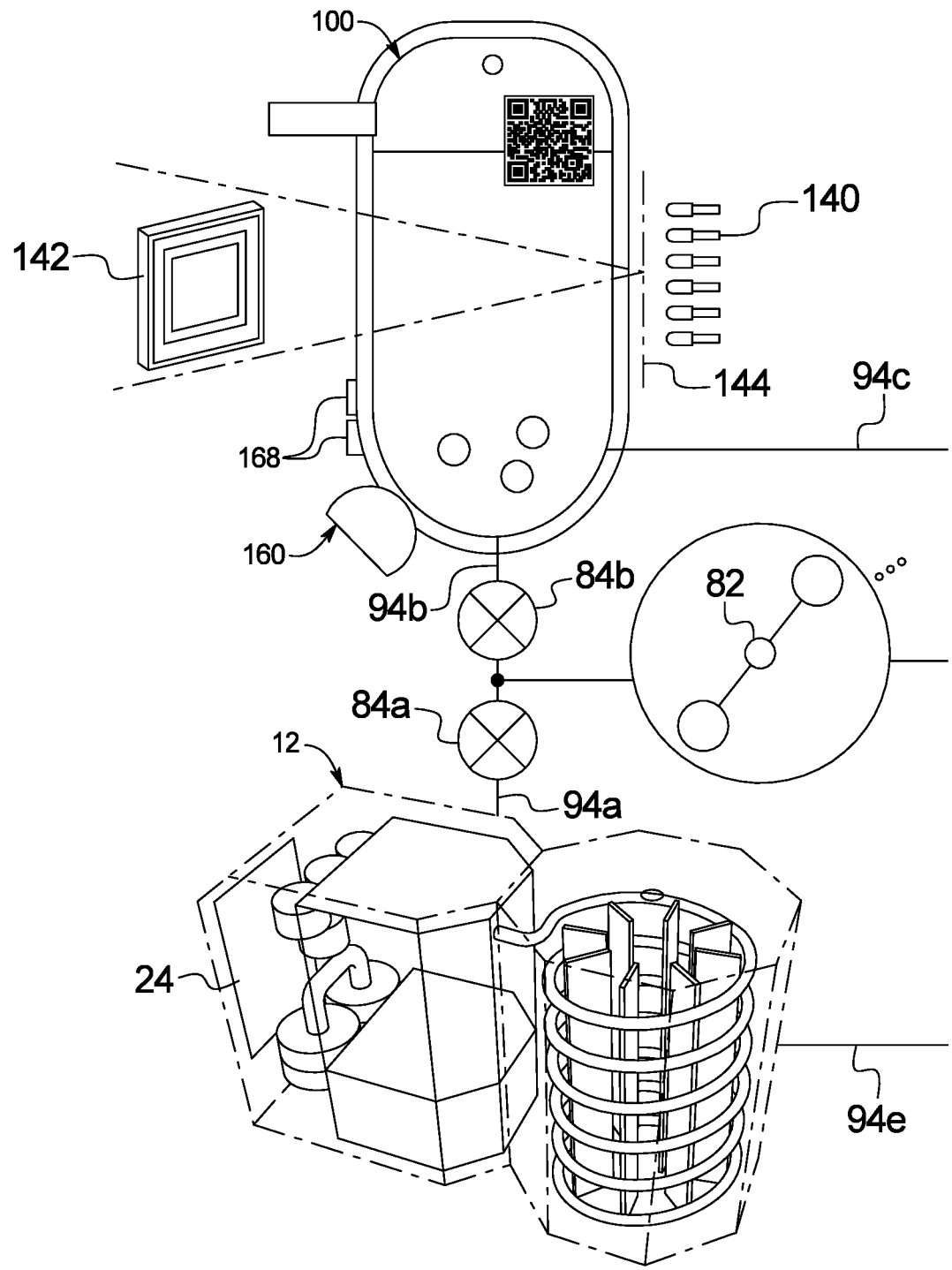
FIG. 8 is a perspective view of one embodiment for an onsite diagnostic equipment used to analyze a patient's effluent fluid.

FIG. 8 illustrates an alternative embodiment in which system 10 provides onsite diagnostic equipment that analyzes patient P's effluent solution. Here, after inserting the one or more diagnostic capsule 110, control unit 24 may cause the effluent and capsule to mix in a manner described above (may or may not be heated). Once diagnostic concentrate 110*b* is dispersed homogenously within the effluent, the effluent solution is analyzed. FIG. 8 illustrates that in one embodiment an optical sensor array 140 is provided, which includes a plurality of photodiodes 142 that each have discrete wavelength light sources, and which each shine through one or more aperture 144 provided in a wall of holder 152 discussed next. Optical sensor array 140 may be mounted to holder 152 in a same manner as, and possibly with, reusable housing 124 and associated indexing equipment discussed in connection with FIG. 7.

Optical sensor array 140 analyzes the effluent solution and dissolved diagnostic capsules 110 by modulating a light array across a spectrum of wavelengths through the aperture 144 and measuring the incident light with the photodiode sensor array, which provides more nuanced data as opposed to white light or a color camera. The optical sensor array 140 may use multiple wavelengths of light for varying reasons. In some instances, diagnostic capsules 110 may cause a color change (e.g., for white blood cell detection, which correlates to peritonitis). In other instances, different wavelengths of light propagate differently through effluent, thereby exposing differing distortions of an aperture pattern. The use of different wavelengths of light provide an additional dimension of data that may be used to characterize changes that indicate peritonitis or other conditions of concern. Diagnostic capsules 110 may for example, be formulated specifically to detect white blood cells or other markers of peritonitis, e.g., by measuring turbidity. Diagnostic capsules 110 may additionally be formulated to look for urea, electrolytes, and phosphates, for example.

Viewing FIGS. 1 and 8, it is contemplated that control unit 24 of system 10 be connected to a server either directly via a modem and internet connection provided with the control unit, or via the wireless connection with patient P's smartphone 98 employing the app that starts treatment and collects effluent sample data and forwards it to the server. The server is in turn accessed by any one or more of the providers of the system, a clinician, a doctor's office, a service portal, or a patient website. The effluent data may be tracked, e.g., by the patient's clinician or doctor, to determine the effectiveness of therapy, look for peritonitis or other patient condition needing attention, and possibly to send an updated patient prescription from the clinician or doctor, through the server, to the dialysis system to run a modified treatment.

In some embodiments, the effluent data for a population of patients undergoing PD may be used to train a machine-learning system. In these embodiments, the effluent data is collected in addition to confirmed indications of peritonitis for the population of patients. The machine-learning system processes the effluent data and the indications of peritonitis to determine effluent patterns that are indicative of a future onset of peritonitis. After training, the machine-learning system analyzes new effluent data for patients to provide warnings if the data indicates peritonitis may occur in the near future for an identified patient.

Volume Control

Referring now to FIGS. 9 to 12, an embodiment for a dialysis fluid volume control subsystem 150 of overall system 10 is illustrated. Dialysis fluid volume control subsystem 150 provides a non-invasive measurement of volume and flowrate, which allows for any type of dialysis fluid pump to be used. From a simplicity of disposable standpoint, the most desirable pump is a peristaltic pump, which simply requires pumping tube 92 to operate with reusable peristaltic pump actuator 82. Peristaltic pumps are known to be less accurate than other types of fluid pumps, such as membrane pumps, and to become less accurate over time as the peristaltic pump tubing degrades. Dialysis fluid volume control subsystem 150 allows system 10 to be completely decoupled from the inaccuracy associated with peristaltic pumping.

Volume control subsystem 150 includes a holder 152, which may be held by, mounted to, or formed integrally with housing 20. Holder 152 in the illustrated embodiment is formed as a clamshell having a first clamshell panel 154 and a second clamshell panel 156. Clamshell panels 154 and 156 may be made of metal and/or plastic, and which may be commensurate with the material(s) of housing 20. Clamshell panels 154 and 156 in an embodiment are rigid and vertically disposed and accept flexible, vertically disposed and sterilized mixing container or bag 100 as discussed above for holding fresh dialysis fluid, used dialysis fluid, saline, purified water and concentrates for mixing dialysis fluid, or other medical fluids.

As whichever fluid fills the vertically disposed bag 100, the bag where the fluid is located conforms exactly (or near exactly) to the shape of vertically disposed clamshell holder 152. The filling fluid also increases pressure within sterilized bag 100. Volume control subsystem 150 capitalizes on the known relationship between pressure and head height. With all other dimensions of the fluid within bag 100 known due to the known dimensions of vertically disposed clamshell holder 152, except for the height of fluid within the bag, solving for the head height based on a measured pressure of the fluid allows control unit 24 to calculate the volume of fluid in bag 100 at a given time. Control unit 24 also calculates a difference between head heights of two different fluid levels and divides the difference by a time between pressure measurements to determine flow rate.

In an embodiment, one or more pressure sensor 160 (see also FIG. 1) is located at the bottom of clamshell holder 152, e.g., is fixed within an opening or mounting structure formed in the lower portion of clamshell panel 154 in the illustrated embodiment. Pressure sensor 160 may include a pressure pouch 162 that is mounted to or into clamshell panel 154 of clamshell holder 152, wherein pressure pouch 162 makes contact with the vertically disposed container or bag 100. Pressure pouch 162 and a transmission tube 164 attached thereto hold air or other pressure transmission medium, which transfers the pressure due to medical fluid within vertically disposed bag 100 to a pressure transducer 166, such as a load cell, strain gauge, and/or compensated microelectromechanical systems ("MEMS") pressure sensor. Load cell or strain gauge 166 outputs a signal indicative of the pressure and thus the head height of medical fluid within bag 100 to control unit 24, which determines head height and multiplies the head height by the cross-sectional area of the clamshell to determine volume, and divides the volume over a time delta (e.g., time between pressure measurements) to determine flowrate. Two or more pressure sensors 160 may be provided, each outputting to control unit 24, for redundancy and accuracy, and to detect a malfunctioning sensor, if desired.

In one embodiment, volume control subsystem 150 is configured not to completely fill vertically disposed bag 100, so that the bag does not apply pressure to the medical fluid located therein. Also, the top of the bag is not constrained by clamshell holder 152 as illustrated in FIGS. 9 to 12 so as not to pressurize the bag. Additionally, vertical bag 100 and clamshell holder 152 overlap so that the liquid filled cross-sectional area is defined by the known dimensions of the clamshell holder as opposed to the welds or seams of the container or bag.

It is contemplated to install one or more liquid level sensor 168 in or on a lower portion of a panel 154 or 156 of rigid clamshell holder 152 to maintain a baseline level of medical fluid within flexible bag 100. In the illustrated embodiment, liquid level sensor 168 is located to align with bag 100 where it just starts to angle inward from vertical. The baseline level of fluid serves multiple purposes. First, the bottom of clamshell holder 152, and thus flexible bag 100 contained therein, may be angled, rounded or otherwise changing in cross-section to help direct fluid to inlet/outlet port 102 or 104, and so that bag 100 does not have to be formed with a flat bottom. The change in cross-section may cause flexible bag 100 to not be perfectly aligned with clamshell holder 152. Second, the contacting of one or more pressure sensor 160 with the bottom of bag 100 may cause misalignment between the bag and the clamshell holder. In an embodiment, the liquid below the baseline level is not taken into account in the volume or baseline determination, such that each of the discrepancies just described existing below the baseline level may be ignored. Instead, a difference in head height levels above the baseline level is used to determine an amount of fluid delivered to or removed from flexible bag 100.

Liquid level sensor 168 may for example be a non-invasive capacitive sensor that senses the level of medical fluid within flexible container or bag 100 and outputs to control unit 24 as indicated by the dotted line extending therefrom. Suitable level sensors for sensor 168 are disclosed in the following patent applications owned by the assignee of the present disclosure: U.S. provisional application No. 62/884,862, filed Aug. 9, 2019 and U.S. provisional application No. 62/830,906, filed Apr. 9, 2019, the contents of each of which are incorporated herein by reference and relied upon. An output from sensor 168 is triggered for example upon a patient fill (fresh dialysis fluid to patient P) or upon an effluent drain (used dialysis fluid to drain 76 or tank 14 of distillation unit 12) when the corresponding liquid level falls to the level at which sensor 168 is positioned against bag 100. Upon the output from sensor 168 being triggered, control unit 24 stops treatment and causes user interface 26 and/or speakers to issue and alarm. An alarm may alternatively or additionally be sent to patient P's smartphone 98. The remedy to the alarm may be to take stock of how much treatment has taken place, flush all remaining fluid from bag 100 to drain 76 or tank 14 of distillation unit 12 and start over. In some embodiments, the liquid level sensor 168 may include or be used in connection with a tilt sensor (e.g., an accelerometer). An output from the tilt sensor may be used to compensate for tilt within a certain range for level sensing. If a detected tilt exceeds a specified threshold, the control unit 24 may generate an alarm.

The establishment of a baseline level via sensor 168 also ensures that a fill of fresh or used dialysis fluid into flexible bag 100 is commenced with the liquid level at or above the baseline level. In an embodiment, two or more level sensors 168 (see FIG. 1) are provided to establish one more warning level above the baseline level, which triggers a signal that control unit 24 uses to take evasive action prior to the fluid level reaching the baseline level. An upper baseline level sensor 168 may also be provided to ensure that flexible bag 100 does not fill completely and begin to pressurize.

Figure 9:
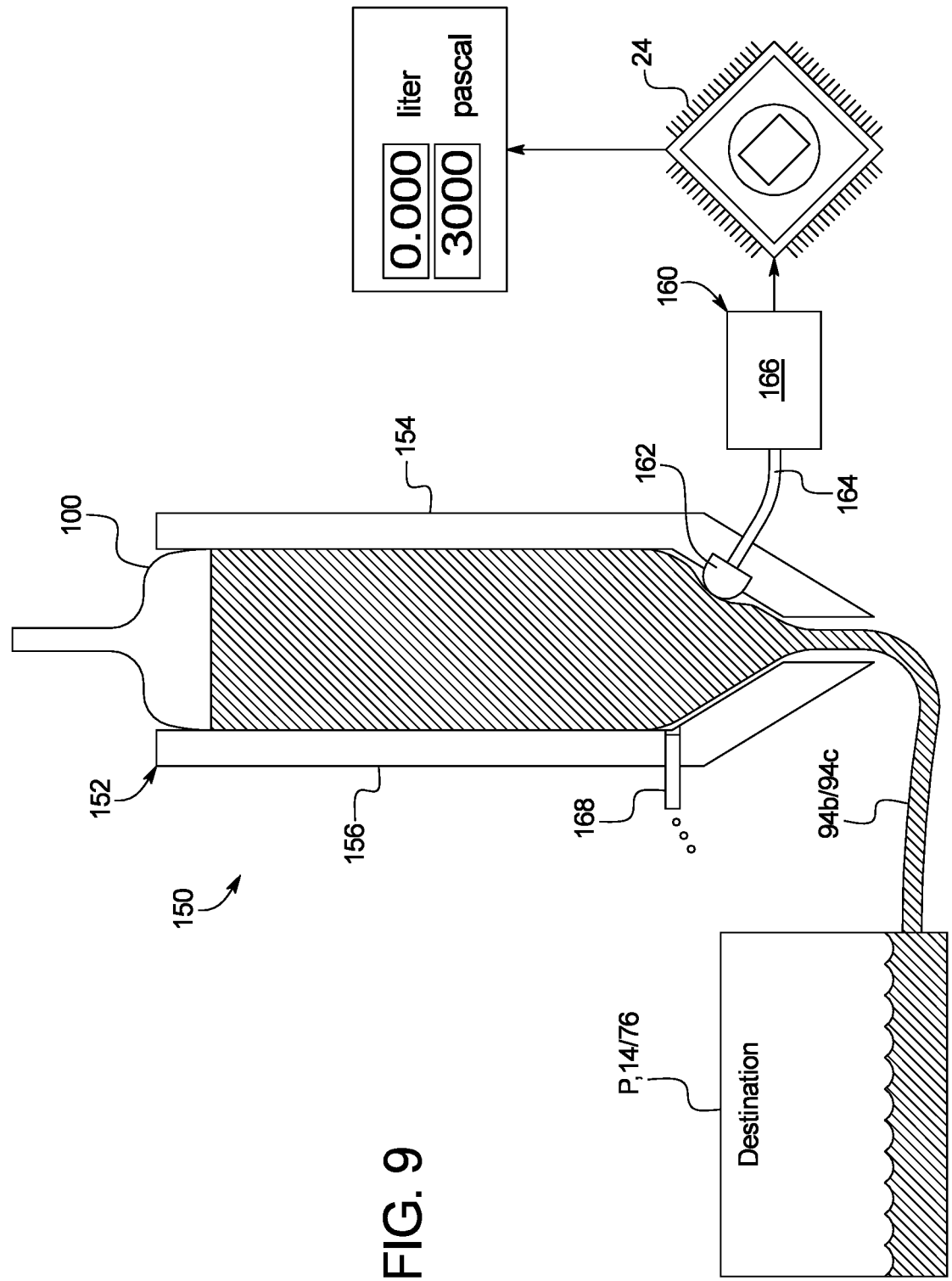
FIG. 9 is a side view of one embodiment of a dialysis fluid volume control subsystem of the present disclosure showing a fluid level at a first level.
Figure 10:
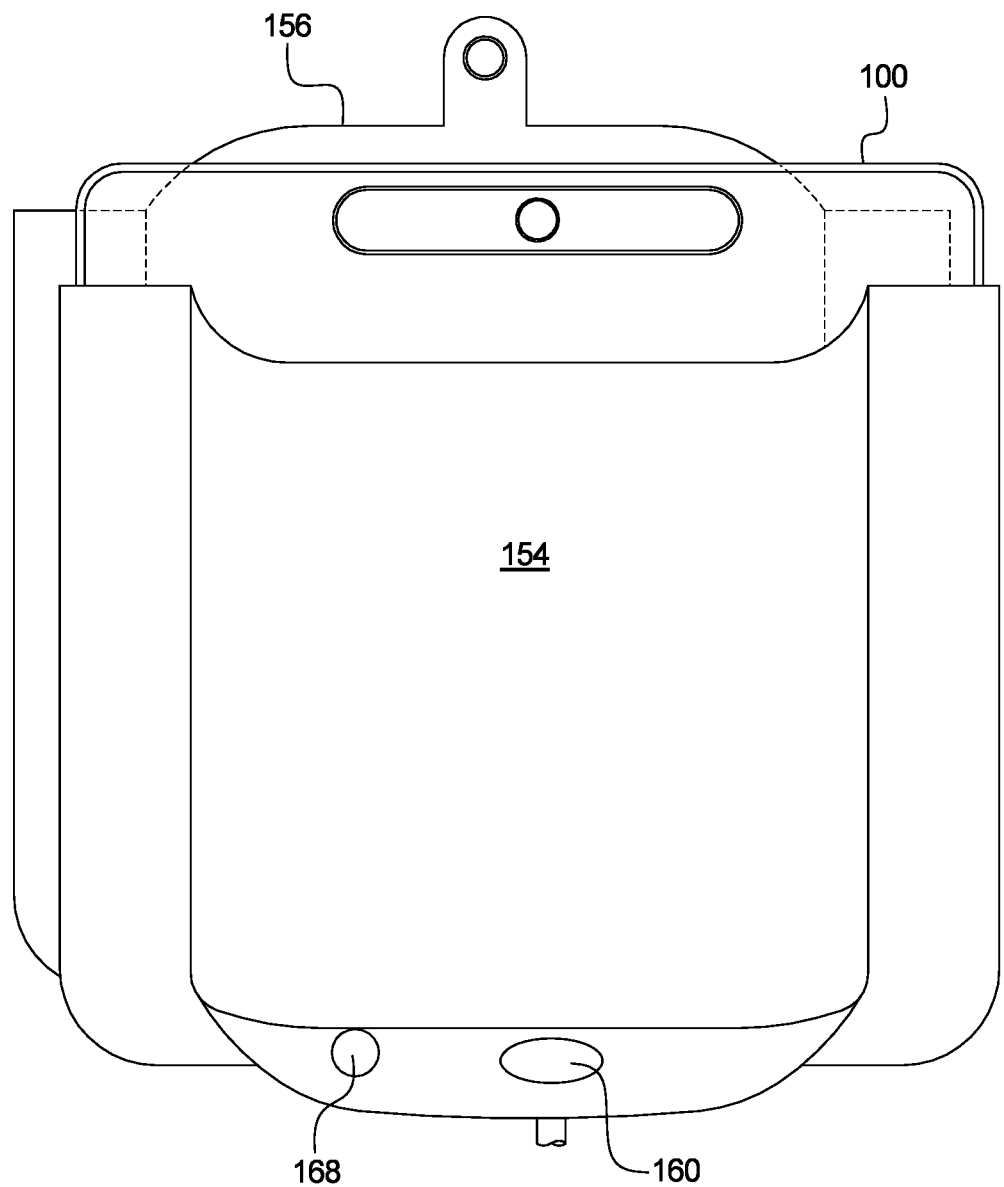
FIG. 10 is a front view of one embodiment of a dialysis fluid volume control subsystem of the present disclosure.
Figure 11:
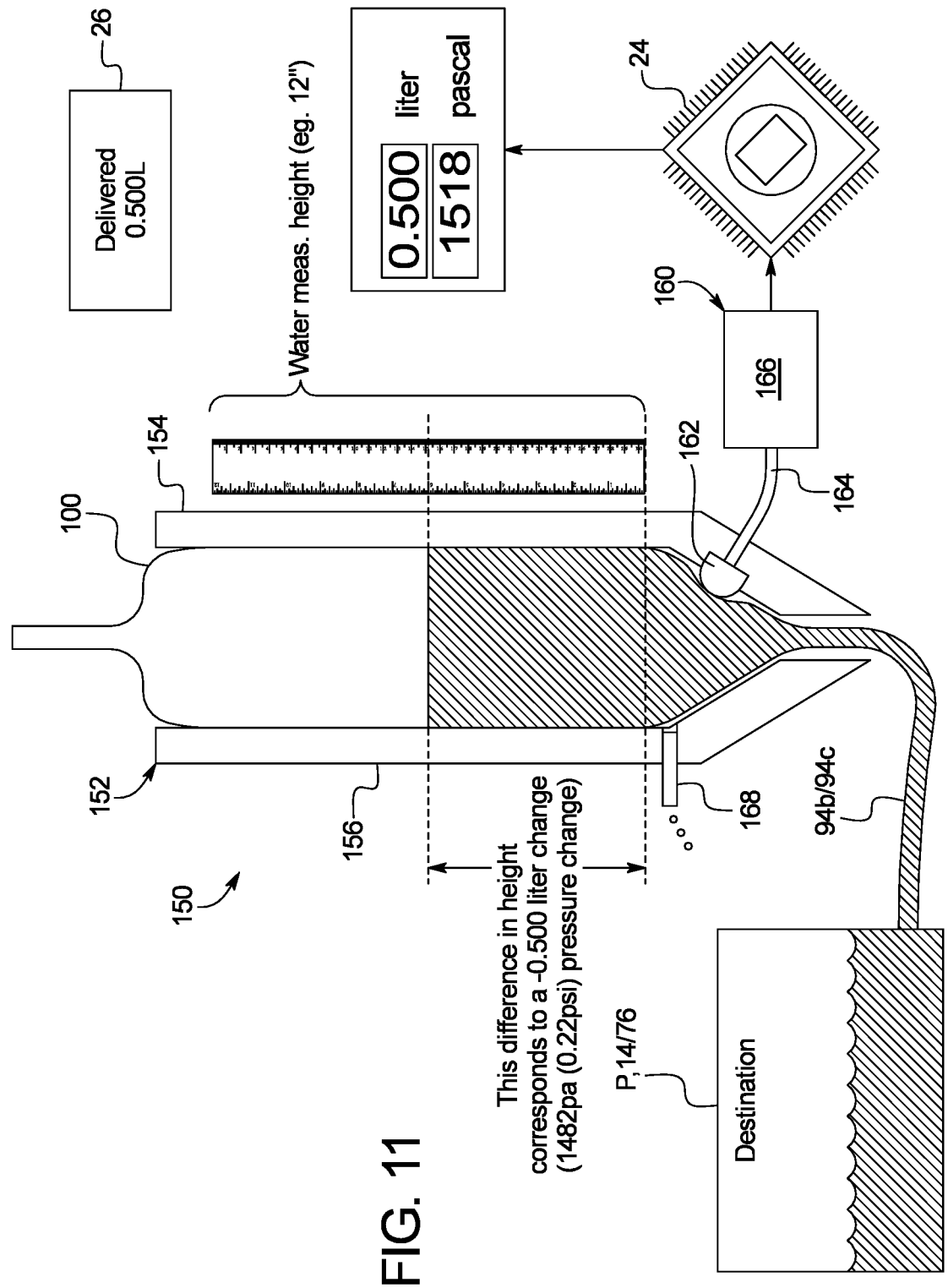
FIG. 11 is a side view of one embodiment of a dialysis fluid volume control subsystem of the present disclosure showing a fluid level at a second level.
Figure 12:
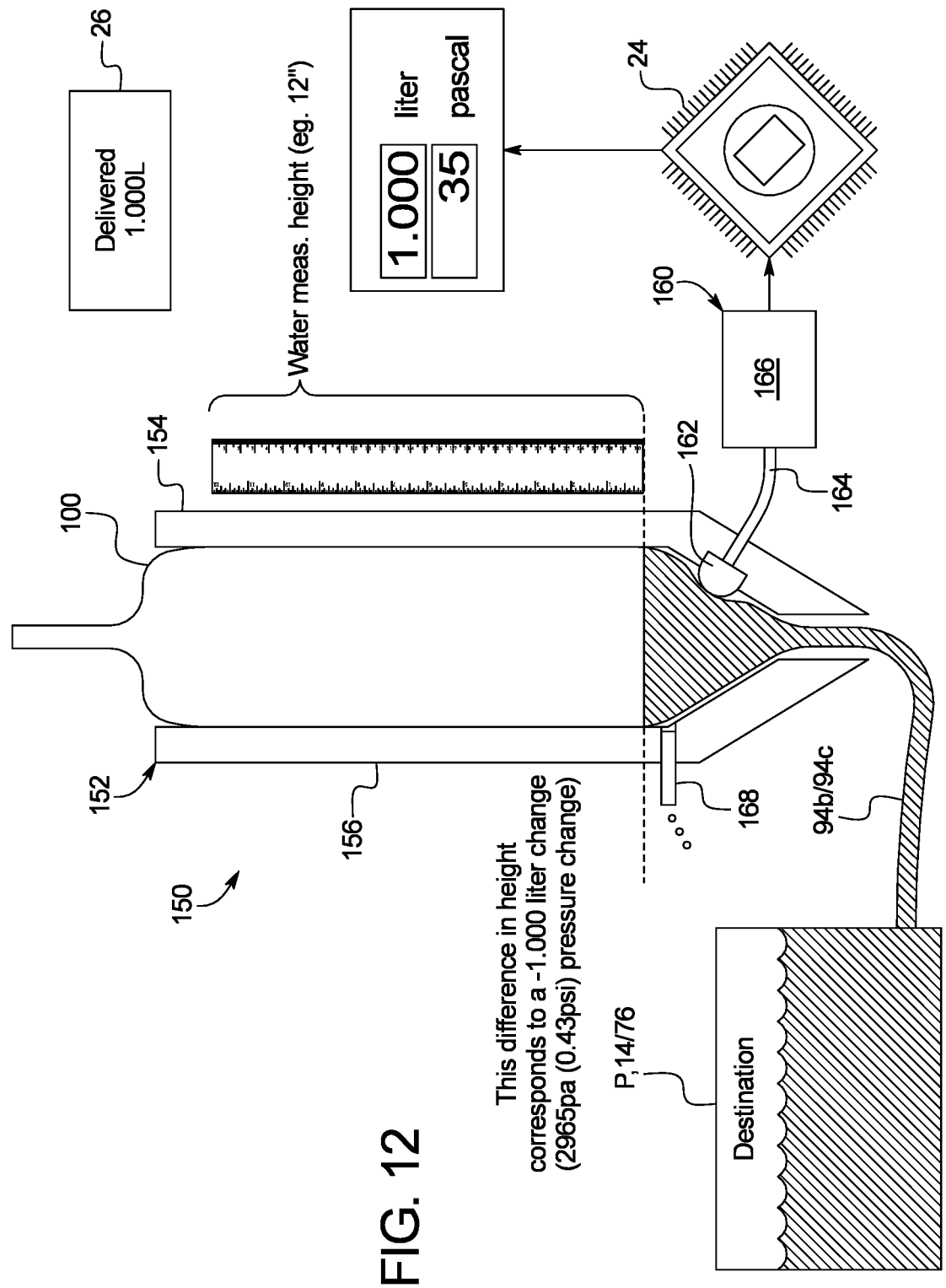
FIG. 12 is a side view of one embodiment of a dialysis fluid volume control subsystem of the present disclosure showing a fluid level at a third level.

FIGS. 9, 11 and 12 illustrate an example of a volume determination. The head height of the column of fluid in bag 100 is determined by the pressure measured by pressure sensor 160 divided by the density of the fluid in bag 100 multiplied by the local gravity. Control unit 24 stores different densities for different fluids. For example, 0.9% saline is 1.005 g/ml versus water, which is 1.000 g/ml. Saline therefore produces a slightly higher pressure than water per unit height. Likewise, different fresh dialysis fluids may have different densities, which are stored at control unit 24. The density of effluent dialysis fluid may be patient specific, and it is therefore contemplated to determine same on a patient-by-patient basis for entry into control unit 24. When preparing dialysis fluid, control unit 24 uses different densities at different times as purified water, e.g., WFO, is mixed with concentrate 100b to form dialysis fluid.

In FIG. 9, bag 100 is full, no fluid has been delivered and the pressure of fluid as measured by pressure sensor 160 and outputted to control unit 24 is 3000 Pascals. In FIG. 11, bag 100 is partially full and the measured pressure as measured by pressure sensor 160 and outputted to control unit 24 has dropped to 1518 Pascals, a 1482 Pascal (0.22 psig) change, which corresponds to a 15.2 cm (6 inch) drop in head height. That distance multiplied by the known and constant cross-sectional area within bag 100, as created by clamshell holder 152, results in a 0.50 liter of fluid being delivered (as indicated by user interface 26) to patient P, tank 14 of distillation unit 12 or drain 76. In FIG. 12, bag 100 is mostly empty (but still above baseline as set by level sensor 68) and the measured pressure as measured by pressure sensor 160 and outputted to control unit 24 has dropped to 35 Pascals, an overall 2965 Pascal (0.43 psig) change, which corresponds again to a 15.2 cm (6 inch) drop in head height. That distance multiplied by the known and constant cross-sectional area within bag 100, as created by clamshell holder 152, results in an additional 0.50 liter of fluid being delivered to patient P, tank 14 of distillation unit 12 or drain 76, as indicated by user interface 26.

In FIG. 12, the remaining 35 Pascals of pressure is due to the remaining fluid residing in the funnel or changing cross-sectional area of bag 100 and clamshell holder 152. As discussed above, it is contemplated to stop depleting fluid from bag 100 prior to the fluid level dropping into the funnel area and to provide level sensor 168 as a backstop to ensure that the fluid level does not fall into the funnel area. The subsequent drain of patient P and filling of bag 100 begins at the 35. Pascals of pressure and builds to a pressure corresponding to a prescribed drain volume, e.g., fill volume+fill volume*(0.07) to take into patient P's ultrafiltration. In the above example, the drain volume would be two liters plus two liters*(0.7) or 2.14 liters. Control unit 24 in the example drains patient P until obtaining a pressure reading from pressure sensor 160 of a pressure corresponding to 2.14 liters above 35 Pascals.

In an embodiment after the patient drain, all fluid within bag 100, including the remaining fluid corresponding to the 35. Pascal pressure is removed to drain 76 or tank 14 of distillation unit. The above procedure is then repeated. It is accordingly contemplated to formulate concentrate capsules 110 to make more than the prescribed fill volume's worth of fresh dialysis fluid to allow (i) the changing head height evaluations discussed above to occur in the constant cross-sectional area portion of bag 100 and holder 152 and (ii) fluid for disposable set 90 to be primed with fluid for recirculation and mixing.

Figure 13:
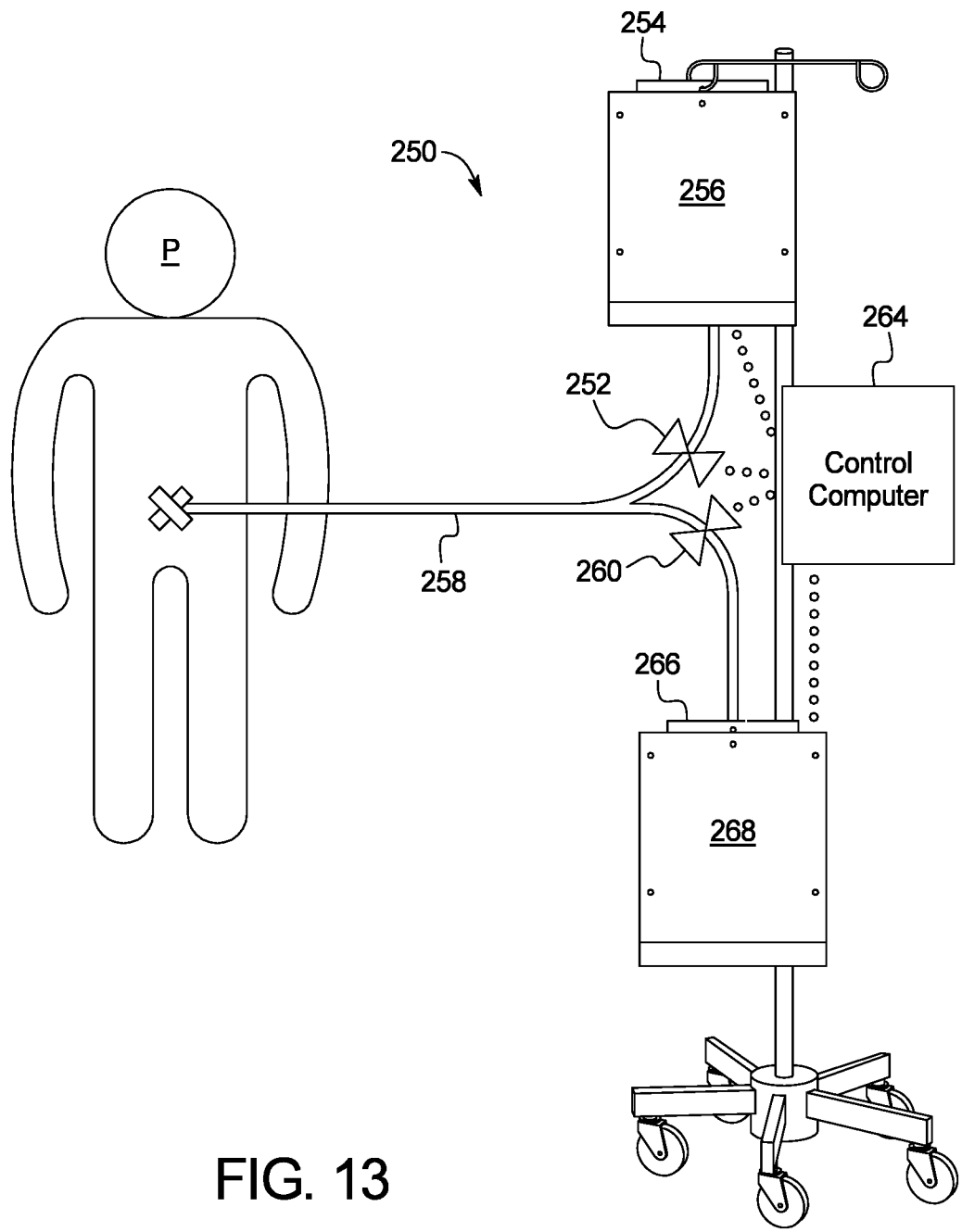
FIG. 13 is a perspective view of an alternative gravity fed system that employs the dialysis fluid volume control subsystem of the present disclosure.

In any of the changing head height evaluations discussed above, instantaneous flowrate may be measured at any time during fluid flow by taking first and second pressure measurements, determining the volumes corresponding to the pressure measurements, and dividing by the time between the measurements. Flowrate is controlled by adjusting the speed of pump actuator 82 in one embodiment As discussed herein, dialysis fluid volume control subsystem 150 allows for a relatively inaccurate but simple peristaltic pump actuator 82 to be used. In an alternative embodiment illustrated in connection with FIG. 13, a low cost gravity fed system 250 is provided that does not use a pump, but instead, under computerized control of a fresh valve 252 via control unit 264, allows fresh fluid to flow from a fresh flexible bag 254 held within a fresh fluid clamshell holder 256 to patient P for treatment via a patient line 258, and used fluid to flow from patient P, under computerized control of used valve 260 via control unit 264, to a used flexible bag 266 held within a used fluid clamshell holder 268. Fresh and used fluid clamshell holders 256 and 268 and corresponding flexible bags 254 and 266 operate just as described above, except that they are one-way with fluid only flowing out or into containers or bags 254 and 266. Fresh fluid clamshell holder 256 and flexible bag 254 allow control unit 264 to monitor volume and flowrate of fresh dialysis fluid to patient P. Used fluid clamshell holder 268 and flexible bag 266 allow control unit 264 to monitors volume and flowrate of used dialysis fluid removed from patient P. The difference between the two is the patient's ultrafiltration ("UF") removal.

Inline Heating

Figure 14:
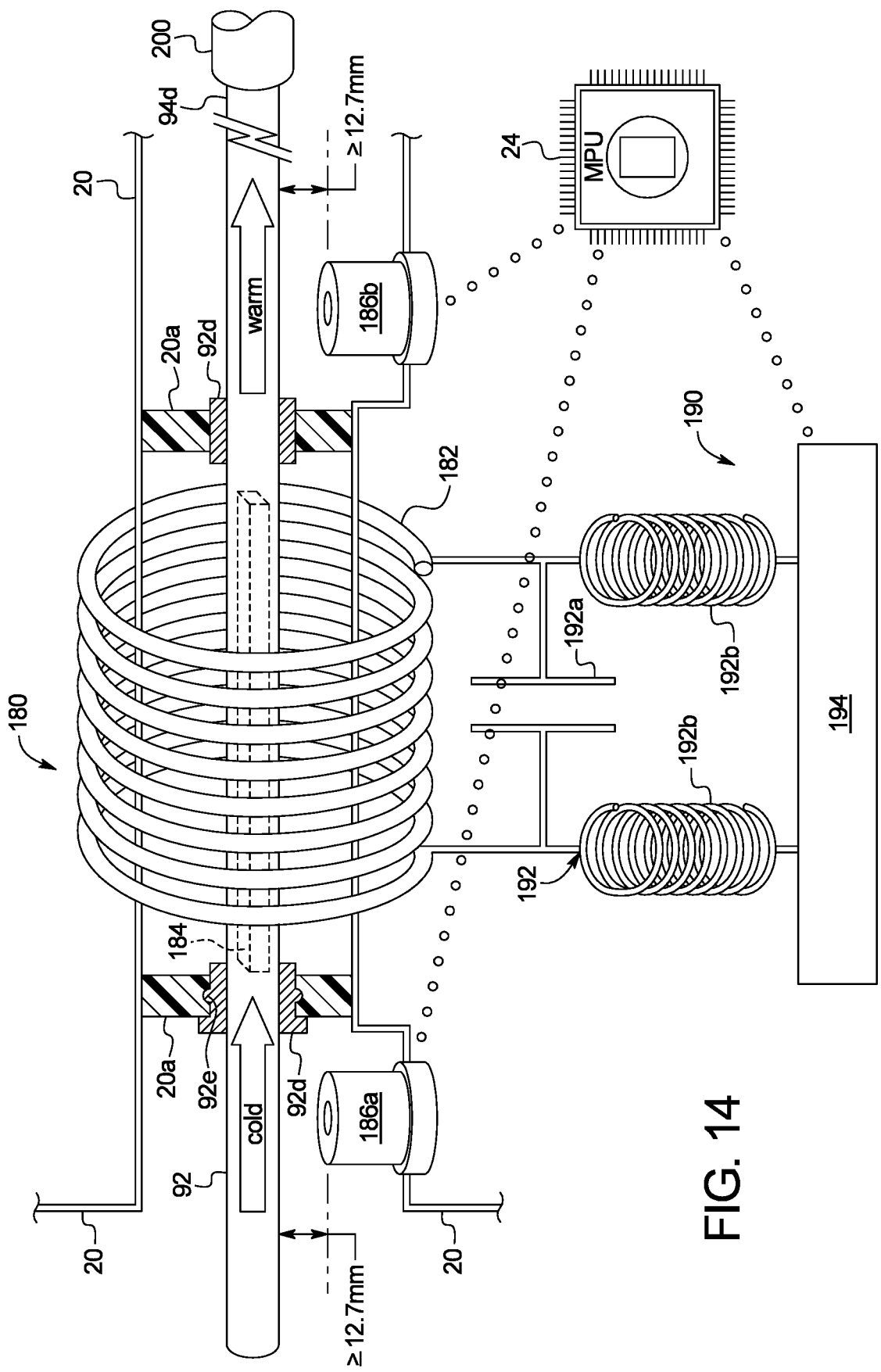
FIG. 14 is an elevation view of a first inline fluid heater configuration of the present disclosure.
Figure 15:
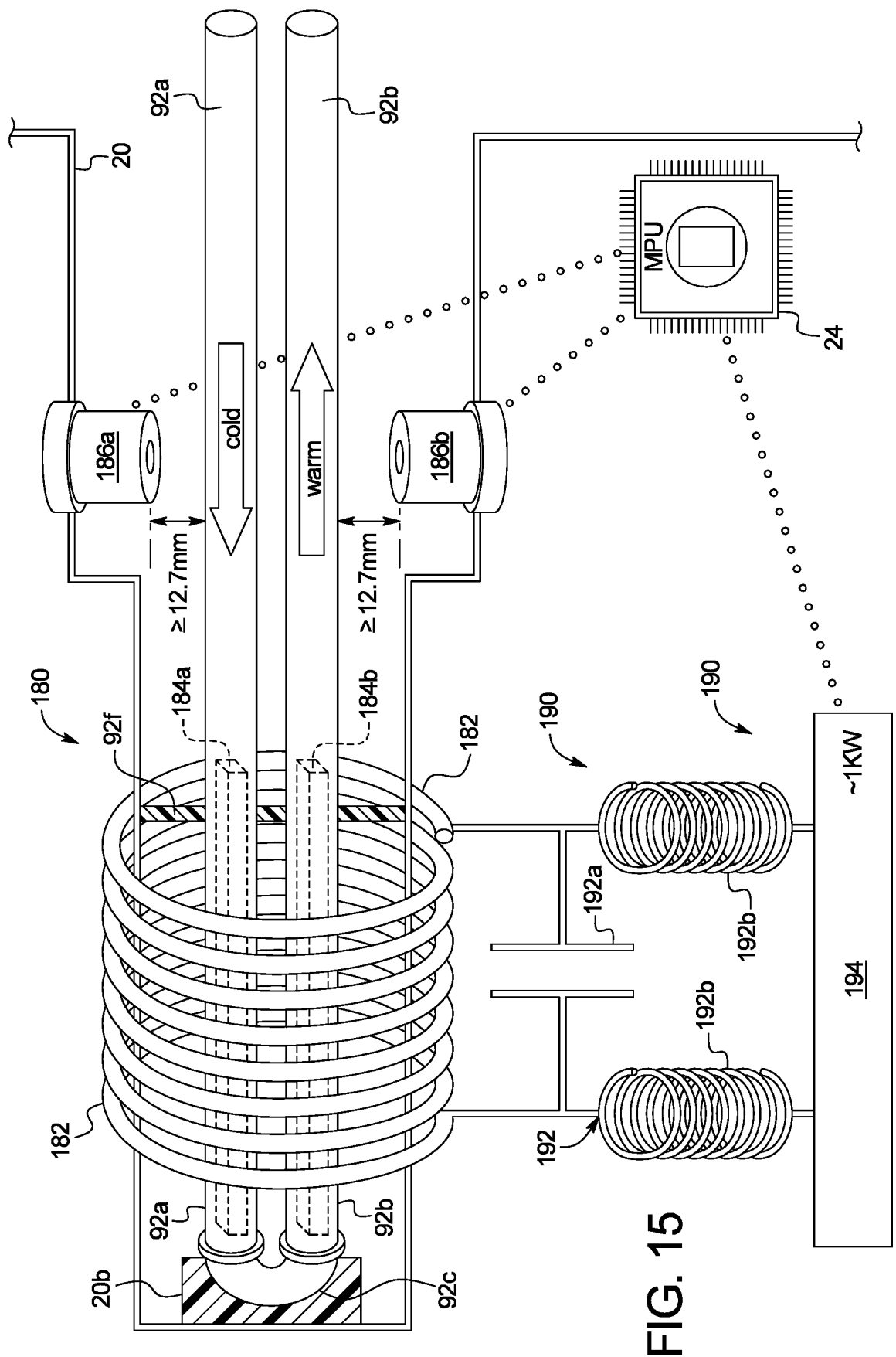
FIG. 15 is an elevation view of a second inline fluid heater configuration of the present disclosure.
Figure 16:
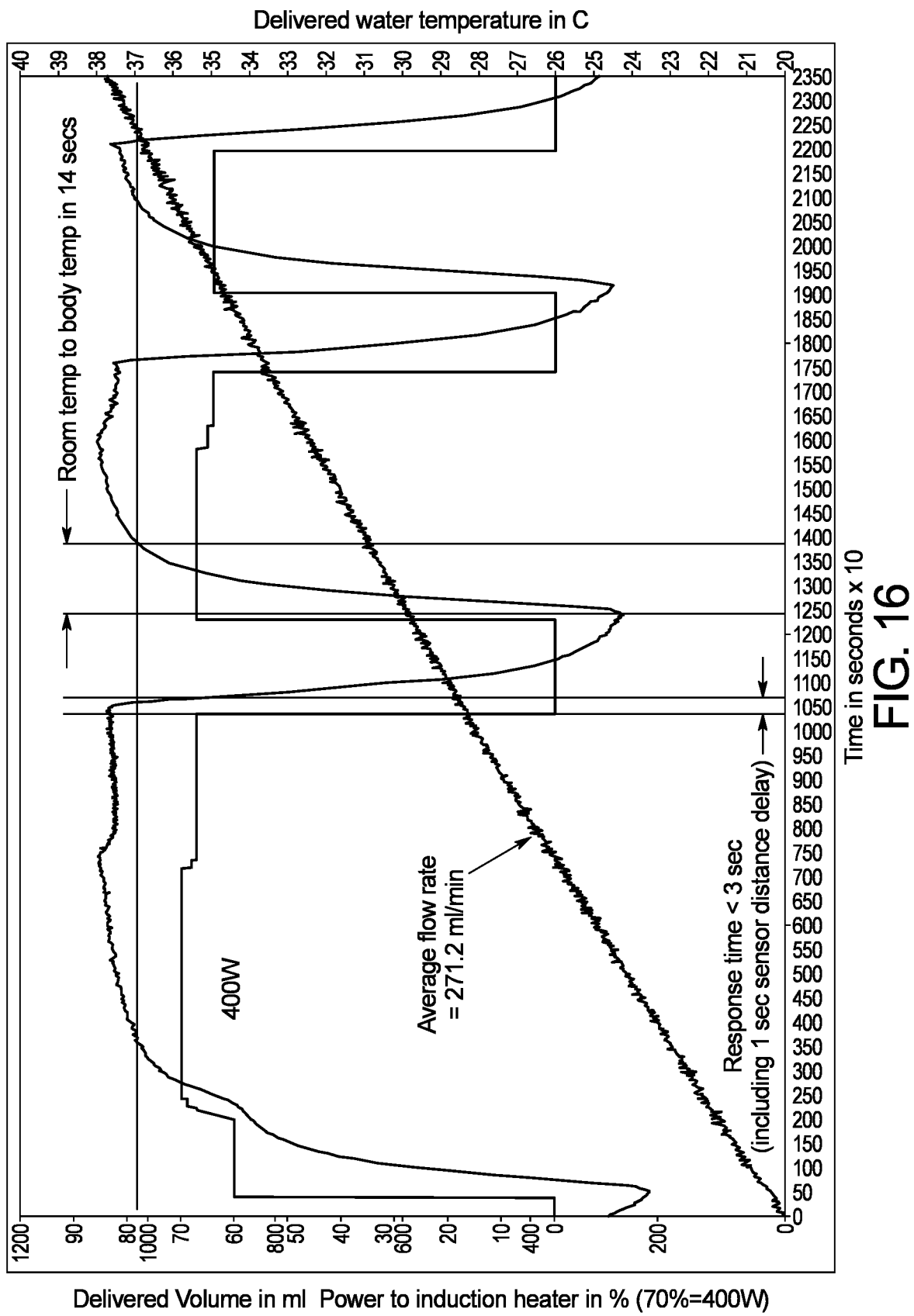
FIG. 16 is a graph illustrating an example output of the inline fluid heater of the present disclosure.

Referring now to FIGS. 14 to 16, various embodiments of an inline heater 180 are illustrated. Inline heater 180 is illustrated in FIG. 1 as being located between pump actuator 82 and patient P to heat the dialysis fluid flowing through cylindrical heating and pumping tube 92 to patient temperature, e.g., 37° C., prior to delivery to the patient. As discussed previously, dialysis fluid entering inline heater 180 may be preheated to close to patient temperature be either one or both of (i) heating due to distillation unit 12 or (ii) heating during dialysis fluid mixing. In any case, inline heater 180 is also capable of heating the dialysis fluid from ambient temperature to body temperature.

Inline heater 180 in the illustrated embodiment is an inductive heater having an inductive coil 182 within which the disposable component of the heater is disposed, wherein the disposable component, like that of pump, is a single tube or a tube that is folded or provided with a fitting such that the tube reverses direction 180 degrees. Tube 92 (FIG. 14), or each leg 92a and 92b of the dual tube (FIG. 15), is provided with a susceptor 184 (FIG. 14) or susceptors 184a, 184b (FIG. 15), which may be any medically safe material having the the ability to absorb electromagnetic energy and convert the energy to heat. In an embodiment, susceptors 184, 184a, 184b are made of a medically safe material that exhibits properties of an efficient susceptor, such as 400 series stainless steel, 18-0 magnetic stainless steel, titanium, and combinations and alloys thereof. Susceptors 184, 184a, 184b may have a smooth contour to limit their effect on pressure drop in heating and pumping line 92, a changing contour, e.g., mesh or brillo pad, to increase surface area contact with the fluid to be heated, or a combination of both. In a further alternative embodiment, susceptors 184, 184a, 184b may be made of a twisted strip of metal, which increases surface area contact and contact time without creating undue pressure drop along heating and pumping tube 92.

Tube 92 and tube segments 92a, 92b (FIG. 15) including susceptors 184, 184a, 184b are fitted within an inductive coil 182, which may be a conductive copper coil. Copper coil 182 is located within housing 20 of the dialysis machine and is covered by a plastic (or other material that is not heated by the energized coil) machine panel 20 having guides 20a (FIG. 14), and 20b (FIG. 15), so that a user cannot accidently touch coil 182. Inductive coil 182 is connected electrically to power electronics 190, which may include a resonant circuit 192 and driver electronics 194. Driver electronics 194 operate under the control of computerized control unit 24, which causes power to be supplied to resonant circuit 192 and induction coil 182 when needed, e.g., when fresh dialysis fluid is flowing to patient P, or when WFI and concentrate 110b are being recirculated for mixing, and when feedback from one or more dialysis fluid temperature sensor indicates to control unit 24 that fluid heating is needed.

Resonant circuit 192 in an embodiment is an LC circuit that oscillates at its natural resonant frequency. Resonant circuit 192 includes a capacitor 192a that stores energy in an electric field (E) between its plates, which depends on a voltage across its plates, and an inductor 192b, which stores energy in its magnetic field (B), which depends on a current through the magnetic field. Driver electronics 194 induces a voltage across inductor 192b, which causes a current to charge capacitor 192a with a voltage. Charged capacitor 192a in turn powers inductive coil 182, which in turn induces a current in susceptors 184, 184a, 184b, causing the susceptors to heat and transfer heat to the fluid flowing within tubes 92, 92a, 92b.

In an embodiment, an upstream temperature sensor 186a is mounted to machine housing 20 and is located so as to sense the temperature of cool (or cooler) dialysis fluid (or mixing WFI and concentrate 110b) upstream of susceptor 184 or susceptors 184a and 184b. A downstream temperature sensor 186b is mounted to machine housing 20 and is located so as to sense the temperature of heated dialysis fluid (or mixing WFI and concentrate 110b) downstream of susceptor 184 or susceptors 184a and 184b and heading to patient P. Temperature sensors 186a and 186b may be non-contact (e.g., thermopile) sensors, so that there is no invasive or direct fluid contact. Control unit 24 uses the temperature sensor feedback and controls power to the resonant circuit 192 and inductive coil 182 using on/off control, proportional-integral-derivative ("PID") control, fuzzy logic control and combinations thereof. In an embodiment, the power supplied to the power electronics is around one kilowatt.

In some embodiments, power for the inductive coil 182 can be determined using a flow rate and an initial temperature of fluid flowing within pumping tube 92 or within flexible bags 254 and 266 using, for example, a thermistor (e.g., the upstream temperature sensor 186a). For example, 100 watts applied by the inductive coil 182 may raise a temperature of fluid flowing at a rate of 100 ml/minute by 1° C. In this example, to raise the fluid temperature by 5° C., 500 watts would have be applied. This relation between flow rate and initial temperature may depend on a cross-sectional area of the tube 92 being known and fixed.

Inductive inline heater 180 is in general a safe system during use. Susceptors 184, 184a, 184b, in an embodiment, increase in temperature only a few degrees above the target temperature, e.g., 37° C., and are cooled immediately by the dialysis fluid (or WFI mixing with concentrate 110b). Likewise, the temperatures of the tube 92 carrying susceptor 184 (FIG. 14) or tubes 92a and 92b carrying respective susceptors 184a and 184b (FIG. 15) do not heat appreciably higher than the target temperature. Temperature sensors 186a and 186b have been found to operate well when positioned more than 12.5 mm (one-half inch) from tubes 92, 92a, 92b carrying the fluid to be sensed. Close and precise positioning of disposable tubes 92, 92a, 92b with respect to the temperature sensors is therefore not overly critical. The inductive, inline heating of heater 180 of the present disclosure is advantageous for at least one reason including: being non-invasive or non-contact, having a quick heating response time, operating with a low cost and space saving disposable, having a high power coupling resulting in efficient heating, using lower cost electronics, control and sensing, and heating accurately.

Referring specifically to FIG. 14, inductive heater 180 includes inductive coil 182 within which heating and pumping tube 92 is inserted for operation. Heating and pumping tube 92 in which susceptor 184 is located may have an inner diameter of from about 4.00 mm (0.16 inch) to about 12.7 mm (0.50 inch). Temperature sensor 186a is located upstream from inductive coil 182 and susceptor 184, while temperature sensor 186b is located downstream from inductive coil 182 and susceptor 184. Temperature sensors 186a and 186b output to control unit 24, which also controls power electronics 190 having resonant circuit 192 and driver electronics 194.

FIG. 14 further illustrates that temperature sensors 186a and 186b are mounted in housing 20 so as to extend from the housing towards heating and pumping tube 92. In the illustrated embodiment inductive coil 182 is located within housing 20 on the other side of the housing wall from tube 92 so that patient P cannot touch the coil. Again, the housing wall separating coil 182 and tube 92 is made of a material, e.g., plastic, that does not affect the magnetic field created by the coil. Housing 20 in the illustrated embodiment is provided with standoffs or guides 20a that define apertures large enough for a patient connector 200 (discussed next) connected to the end of patient line 94d to pass through. It should be appreciated that the standoffs or guides 20a may be optional since centering the tube 92 within the coil 182 may not be critical or needed.

When patient P or a caregiver has inserted heating and pumping tube 92 through housing 20 to the point that susceptor 184 is roughly centered within inductive coil 182, collars 92d located on tube 92 come into registration with the apertures defined by guides 20a. In the illustrated embodiment, tube 92 is slid from left to right. Collar 92d to the right is accordingly configured so that it can slide through the aperture of guide 20a to the left. Collar 92d to the left however is provided with a flanged backstop and/or a detent 92e, which provides visual and/or tactile feedback that susceptor 184 is roughly centered within inductive coil 182 and tends to hold heating and pumping tube 92 in that position during treatment. Guides 20a are also located near temperature sensors 186a and 186b so that pumping and heating tube is maintained a desired distance from the temperature sensors, e.g., at least 12.7 mm (0.5 inch). It should be appreciated that coil 182 and the opening in housing 20 may be oriented horizontally as illustrated or vertically if desired. If vertically, heating and pumping tube 92 may be inserted into housing 20 upwardly or downwardly.

Referring specifically to FIG. 15, inductive heater 180 includes inductive coil 182 within which heating and pumping tubes 92a and 92b are inserted for operation. Heating and pumping tubes 92a and 92b in which susceptors 184a and 184b are respectively located may have an inner diameter of from about 4.00 mm (0.16 inch) to about 12.7 mm (0.50 inch). Temperature sensor 186a is located upstream from inductive coil 182 and susceptors 184a and 184b, while temperature sensor 186b is located downstream from inductive coil 182 and the susceptors. Temperature sensors 186a and 186b output to control unit 24, which also controls power electronics 190 having resonant circuit 192 and driver electronics 194.

FIG. 15 further illustrates that temperature sensors 186a and 186b are mounted in housing 20 so as to extend from the housing towards heating and pumping tubes 92a and 92b, respectively, and be spaced apart from the pumping tube a desired distance, e.g., at least 12.7 mm (0.5 inch). In the illustrated embodiment, inductive coil 182 is located within housing 20 on the other side of the housing wall from tubes 92a and 92b so that patient P cannot touch the coil. Again, the housing wall separating coil 182 and tubes 92a and 92b is made of a material, e.g., plastic, that does not affect the magnet field created by the coil. Housing 20 in the illustrated embodiment is provided with at least one standoff or guide 20b that holds tubes 92a and 92b in a desired position. In the illustrated embodiment, standoff or guide 20b is configured with an indentation or cutout sized and shaped to accept and hold connector 92c, connecting heating tubes 92a and 92b.

Guide 20b holds one end of susceptors 184a and 184b in place relative to inductive coil 182. A locating flange 92f is provided with heating tubes 92a and 92b to hold the other ends of susceptors 184a and 184b in place relative to inductive coil 182. Locating flange 92f is advantageous because it can also space heating tubes 92a and 92b a desired distance apart from one another such that the tubes remain substantially parallel as illustrated in FIG. 15. However, locating flange 92f is disposable along with heating tubes 92a and 92b, adding to disposable cost. Therefore, a second standoff or guide, similar to guides 20a in FIG. 14, may be provided alternatively at the opposite end of susceptors 184a and 184b to hold tubes 92a and 92b. In FIG. 15 the user inserts heating tubes 92a and 92b until they dead end against guide 20b, which may be an easier insertion than inductive heater 180 of FIG. 14. As with FIG. 14, coil 182 and the opening in housing 20 may be oriented horizontally as illustrated or vertically if desired. If vertically, heating and pumping tubes 92a and 92b may be inserted into housing 20 upwardly or downwardly.

FIG. 16 illustrates an output from a prototype inductive inline heater 180 using the components discussed above.

Self-Priming Patient Connector

Referring to FIG. 1, prior to delivering dialysis fluid to patient P, disposable set 90, and most importantly patient line 94d, is primed so that air is not delivered to patient P and volumetric accuracy is not compromised. Known priming typically involves manual steps and cognitive thought that may tax certain patients and make the therapy less appealing. The present disclosure sets forth a patient line connector 200 that, once connected to the patient's transfer set 96, self-primes and then opens to allow dialysis fluid to be delivered to and removed from patient P. The patient does not have to handle connector 200 during the priming operation in one embodiment other than connecting transfer set 96.

FIGS. 17 to 20 illustrate one embodiment of a self-priming patient connector 200 of the present disclosure, which includes a housing 202 having a fluid inlet 204 connected to patient line 94d and a fluid outlet 206 connected to the patient's transfer set 96. Housing 202 may be made of any suitable medical grade material, e.g., medical grade plastic, such as polyvinyl-chloride ("PVC") or suitable medical grade non-PVC material. Housing 202 in FIGS. 17 and 18 also includes a plastic membrane or seal 208 initially covering outlet 206 and a valve housing 210 defining openings 212a, 212b, 212c, 212d . . . 212n, where opening 212a is covered by a hydrophobic (air passing but liquid retaining) membrane 214. Solid seal 208 may, for example, be made of a polyvinylidene chloride ("PVDC"), e.g., approximately, 0.01 mm thick, while hydrophobic membrane 214 may for example be made of a 0.2 micron polytetrafluoroethylene ("PTFE") material. Seal 208 and membrane 214 may, for example, be ultrasonically sealed to housing 202 and housing 210, respectively.

Figure 17:
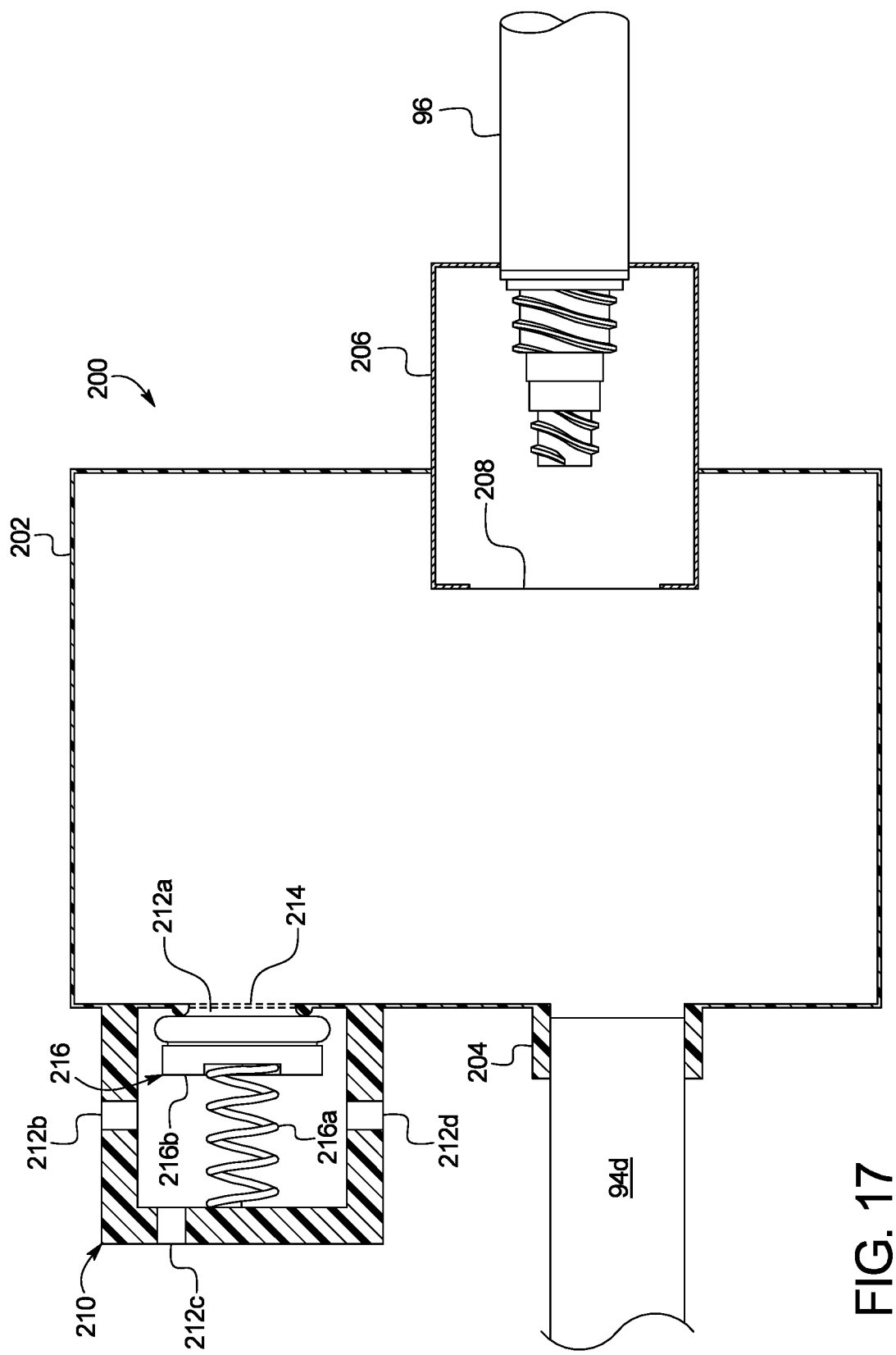
FIGS. 17 and 18 are schematic views of a first embodiment for a self-priming patient connector of the present disclosure.
Figure 18:
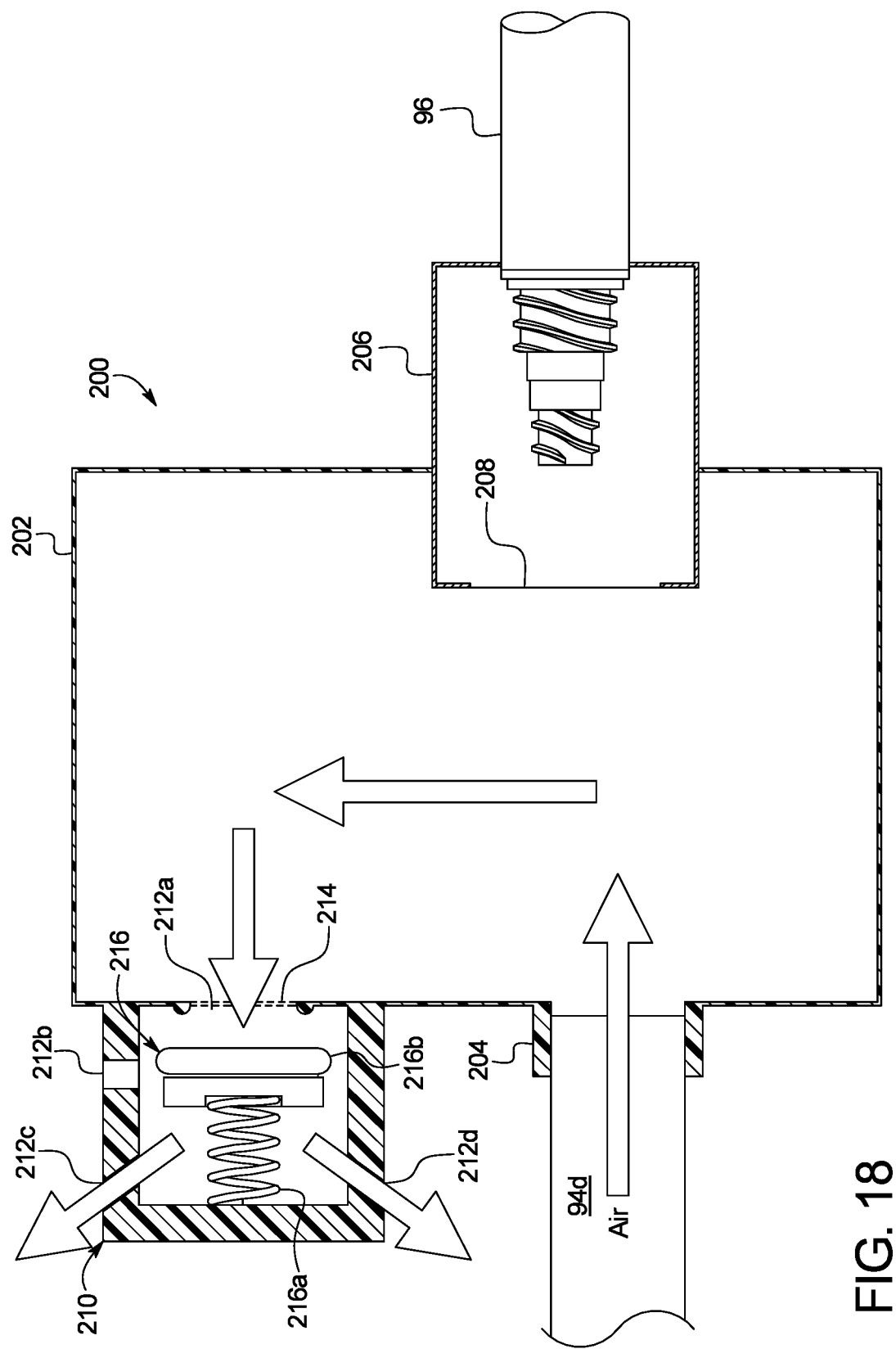

A check valve 216 is provided, which includes a spring 216a (e.g., plastic or stainless steel) and a stopper 216b, wherein spring 216a is compressed between opposing walls of housing 210, so that stopper 212b under atmospheric or negative pressure, e.g., a patient drain, as illustrated in FIG. 17, prevents air from entering housing 202 via hydrophobic membrane 214. FIG. 18 illustrates that under positive pressure during priming, spring 216a is compressed and check valve 216 opens, allowing the priming fluid, e.g., fresh dialysis fluid, to push air out of patient line 94d and patient connector 200, through hydrophobic membrane or vent 214, through valve housing 210 and apertures 212a to 212c, to atmosphere. Hydrophobic membrane 214 allows the air to pass to atmosphere in a sterile manner so that the safety of patient P is not compromised. Once no more air resides within patient line 94d or connector housing 202, hydrophobic membrane 214 becomes wetted with the priming fluid (e.g., fresh dialysis fluid), which prevents the fluid from passing through the membrane, such that pressure builds within patient line 94d and connector housing 202, wherein housing outlet 206 is blocked via hydrophobic membrane 214 and solid seal 208.

In an embodiment, spring 216a is selected such that a relatively small amount of air pressure, e.g., less than 0.5 psig, is able to compress the spring to release air from patient connector 200. In the illustrated embodiment of FIG. 19, the material and/or thickness of solid seal 208 are selected so that the seal ruptures open under the pressure that builds after all (or substantially all) of the air in patient line 94d and patient connector housing 202 has been vented through hydrophobic membrane 214. It is contemplated that solid seal 208 is configured in one embodiment to rupture at around 5 psig, leaving a healthy delta, e.g., on an order of magnitude, between the spring 216a opening pressure and the solid seal 208 rupturing pressure. The difference provides a robust and repeatable patient connector 200. Seal 208 may be provided with score lines or grooves of narrowed thickness (not illustrated), so that the solid seal ruptures in a uniform and repeatable way. For example, the score lines may form an X or cross, which tends to rupture at the junction of the score lines and then tear along the score lines outwardly towards a cylindrical wall of housing 202.

The seal 208 may include, for example, a thin film polymer such as polyvinylidene chloride ("PVCD") or high-density polyethylene ("HDPE"). The seal 208 may alternatively include a thick film that dissolves on contact with dialysis fluid, such as polyvinyl acetate ("PVAC") on a plastic scaffold or polyvinyl alcohol ("PVA") without a scaffold. The seal 208 may further include a soluble glucose/dextrose film on a plastic scaffold that dissolves on contact with dialysis fluid. In further embodiments, the seal 208 may include a reactive material (e.g., an alkali metal) on a thin film polymer. The reactive material reacts with dialysis fluid upon breaching the thin film polymer.

Figure 19:
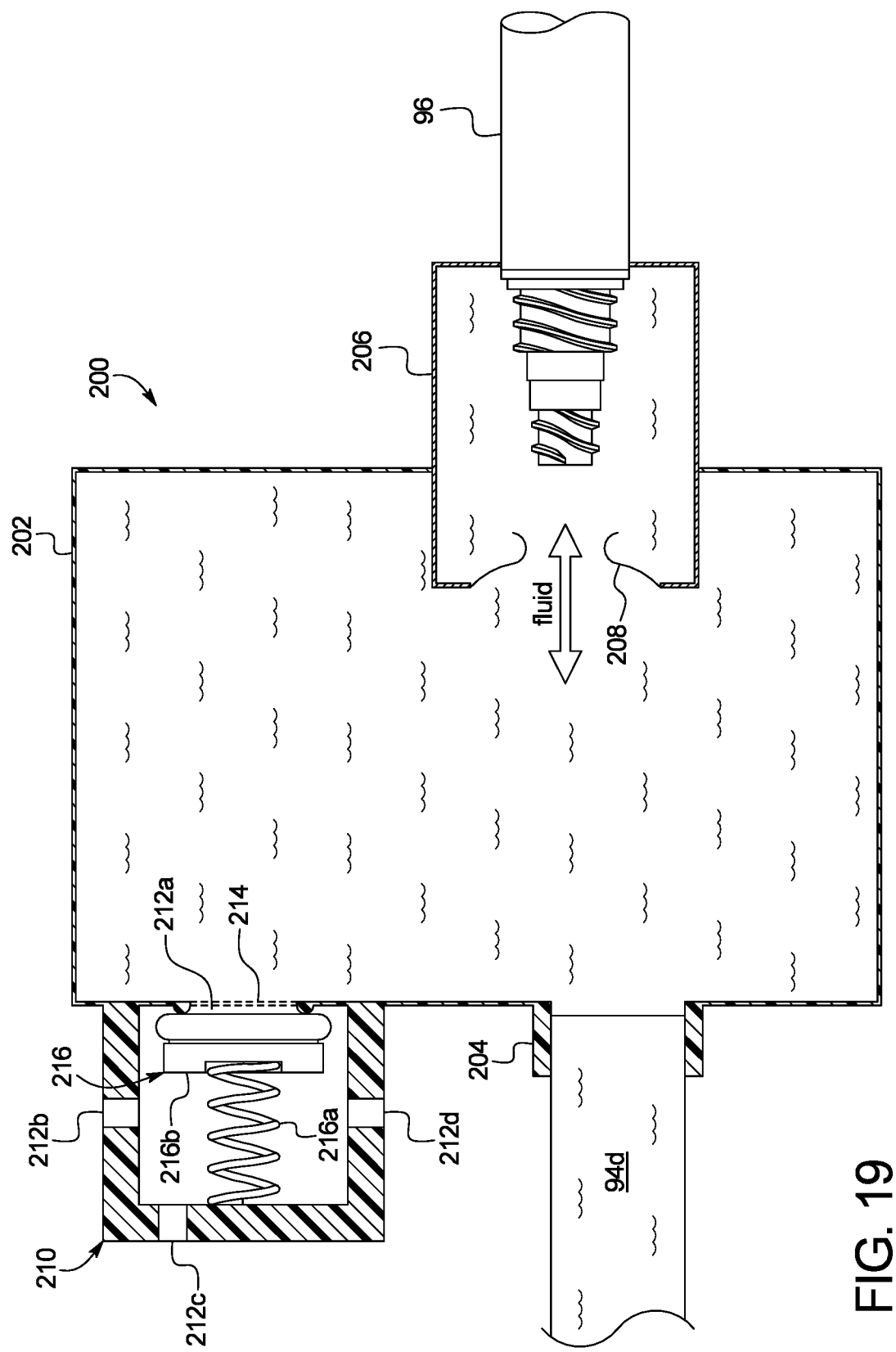
FIG. 19 is a schematic view of the self-priming patient connector of FIGS. 17 and 18 having a solid seal configured to rupture under fluid pressure.

In FIG. 19, with hydrophobic membrane 214 fully wetted, no pressurization can occur through the membrane to valve housing 210. Spring 216a accordingly decompresses, pressing stopper 216b against patient connector housing 202. Fluid pressure within patient connector housing 202 builds, reaching the rupturing pressure of solid seal 208 (e.g., about 5 psig), causing same to open. Thereafter, fresh dialysis fluid may flow to patient P, while used dialysis fluid may be removed from patient P. As discussed herein, the first step of a peritoneal dialysis treatment is often to drain effluent from the patient due to a last fill from a previous treatment or day exchange. Here, fresh dialysis fluid is used to reach the opened seal condition of FIG. 19, after which used dialysis fluid is removed from patient P, pushing the priming fluid in the other direction towards drain 76 or storage tank 14 of distillation unit 12.

Figure 20:
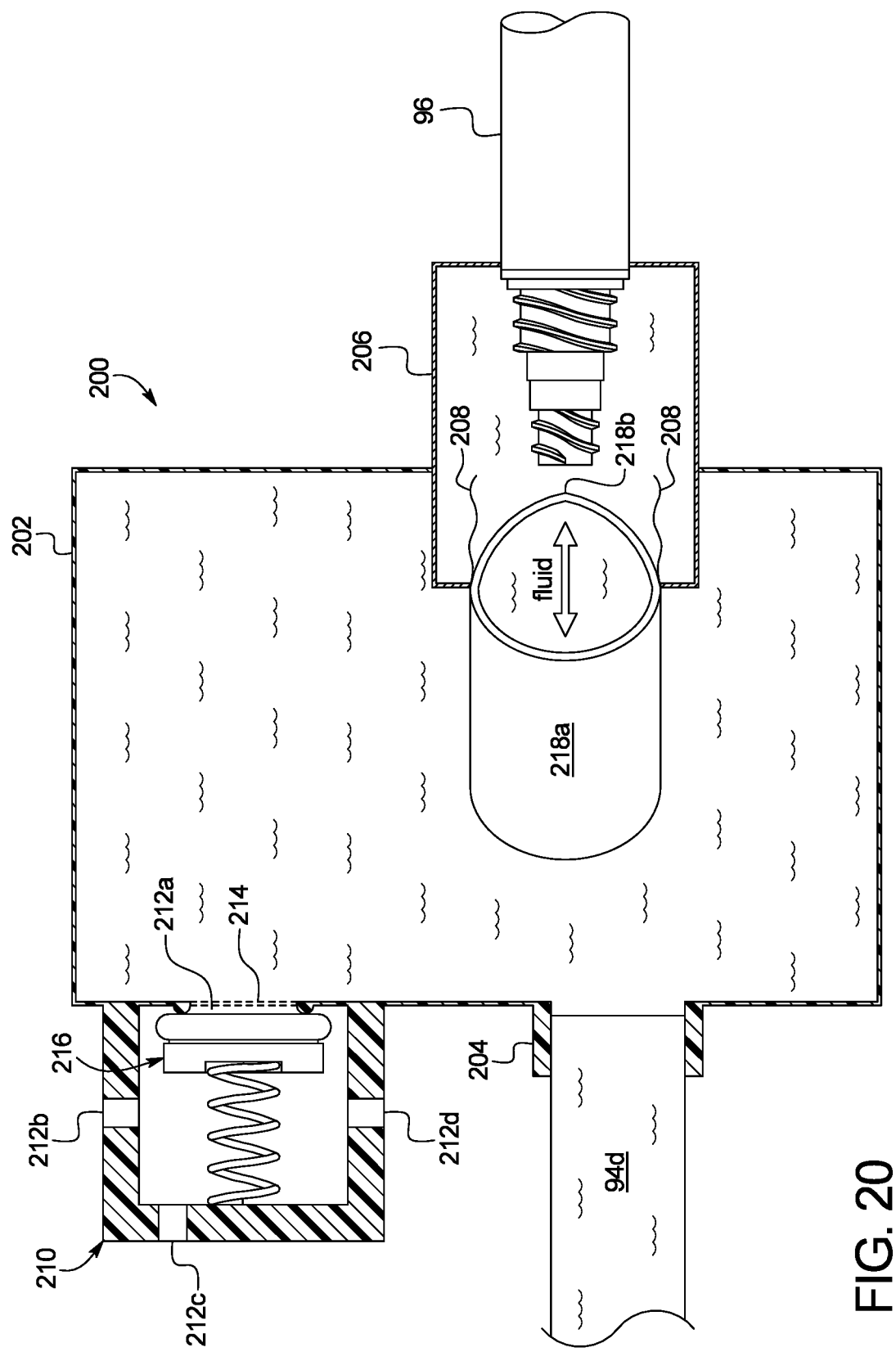
FIG. 20 is a schematic view of the self-priming patient connector of FIGS. 17 and 18 having a cutting member positioned to cut a solid seal open under fluid pressure.

FIG. 20 illustrates an alternative embodiment in which a cutting member 218 is provided, which is not moved under air pressure (e.g., less than 0.5 psig) while air is being purged through hydrophobic membrane 214, but is moved after the air has been purged from connector housing 202 and upon the building of fluid pressure (e.g., about 5 psig) trapped in part by hydrophobic membrane 214 and solid seal 208. Cutting member 218 in the illustrated embodiment is in the form of a cylinder 218a that tapers to a spike 218b made of a resilient and low coefficient of friction material, such as teflon, and which is confined to translate within patient connector 200 over a short distance that is enough to puncture and tear the solid seal. In the illustrated embodiment, cutting member 218 causes the puncture to occur along the outer rim of solid seal 208, so that a tear subsequently takes place along tapering cylinder 218a as it translates through the seal. In an embodiment, a portion of seal 208 remains attached to patient connector 200, so that the seal is not carried to an undesirable place and so that the seal does not inadvertently reseal the outlet 206 of patient connector 200 closed.

Figure 21:
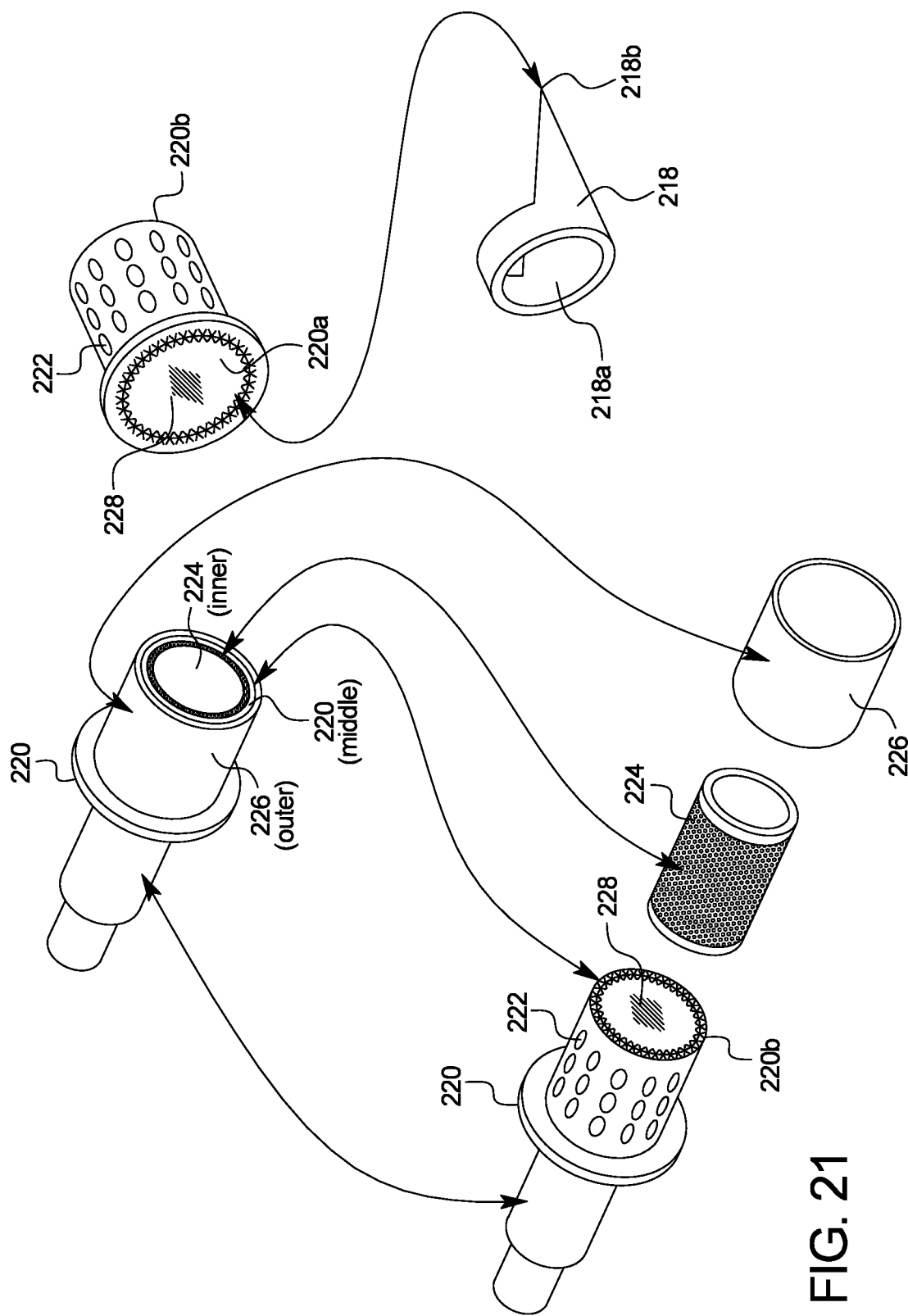
FIG. 21 is an exploded perspective view of a second embodiment for a self-priming patient connector of the present disclosure.

FIG. 21 illustrates an alternative self-priming patient connector 200 of the present disclosure, which may be used with either the ruptured seal 208 embodiment of FIG. 19 or the punctured or cut solid seal 208 embodiment of FIG. 20. Patient connector 200 includes an outer cylindrical housing 220 that is perforated or provided with a series of holes 222 that allow air to be vented from patient line 94d and patient connector 200 under positive pressure from the priming fluid. Cylindrical housing 220 may be made of PVC, non-PVC, PTFE, or other suitable medical grad plastic. Alternative hydrophobic membrane 224 (e.g., PTFE) is also provided as a cylinder having an outer diameter that fits snugly within an inner diameter of perforated outer housing 220. An alternative check valve 226 is provided in the form of an elastomeric sleeve, which is stretched so as to be compressed over the outside of outer housing 220, covering the series of holes 222 when patient connector 200 is placed under atmospheric or negative pressure. Under positive air pressure, elastomeric sleeve 226 is stretched open to allow air vented through hydrophobic membrane 224 and the series of holes 222 to escape to atmosphere. When negative pressure is applied to patient line 94d, e.g., for draining patient P, elastomeric sleeve 226 is press-fit due to its elastic nature (or otherwise connected) and sucked under the negative pressure (assuming membrane 224 is not wetted) to the outside of outer housing 220, covering holes 222.

In the illustrated embodiment, cylindrical housing 220 includes an inlet 220a and an outlet 220b. Inlet 220a (upper right in FIG. 21) or outlet 220b (lower left in FIG. 21) is initially covered or sealed via solid seal 228, e.g., ultrasonically welded to housing 220, which may be scored or grooved as described above for the rupture embodiment. Cutting member 218 in the form of a cylinder 218a that tapers to a spike 218b may or may not be provided. Patient connector 200 of FIG. 21 operates at least substantially the same as described above for connector 200 of FIGS. 17 to 20. Priming fluid delivered through patient line 94d pressurizes air in the patient line and connector 200 to, e.g., less than 0.5 psig, which is enough to expand elastomeric check valve sleeve 226, allowing air to escape patient connector 200 to atmosphere via hydrophobic membrane 224 and holes 222. When all or substantially all of the air has been purged from connector 200, hydrophobic membrane 224 becomes wetted such that pressurization through hydrophobic membrane 224 ceases and elastomeric check valve sleeve 226 returns to its unstretched position, covering holes 222. The fresh dialysis fluid builds in pressure to, e.g., about 5 psig, after which either (i) solid seal 228 configured to rupture ruptures or (ii) cutting member 218 is translated to cut and open solid seal 228. Fresh and used dialysis fluid may then flow in either direction through patient connector 200.

In an alternative implementation of the patient connector 200 of FIG. 21, if cylindrical hydrophobic membrane 224 is sufficiently rigid and is able to be connected sealingly to solid plastic inlet and outlet tubes, ports, etc., then cylindrical housing 220 may be eliminated, such that elastomeric check valve sleeve 226 fits sealingly directly onto hydrophobic membrane 224. Elastomeric check valve sleeve 226 here compresses onto membrane 224 to prevent air from entering patient connector 200 under atmospheric and negative pressures.

Figure 22:
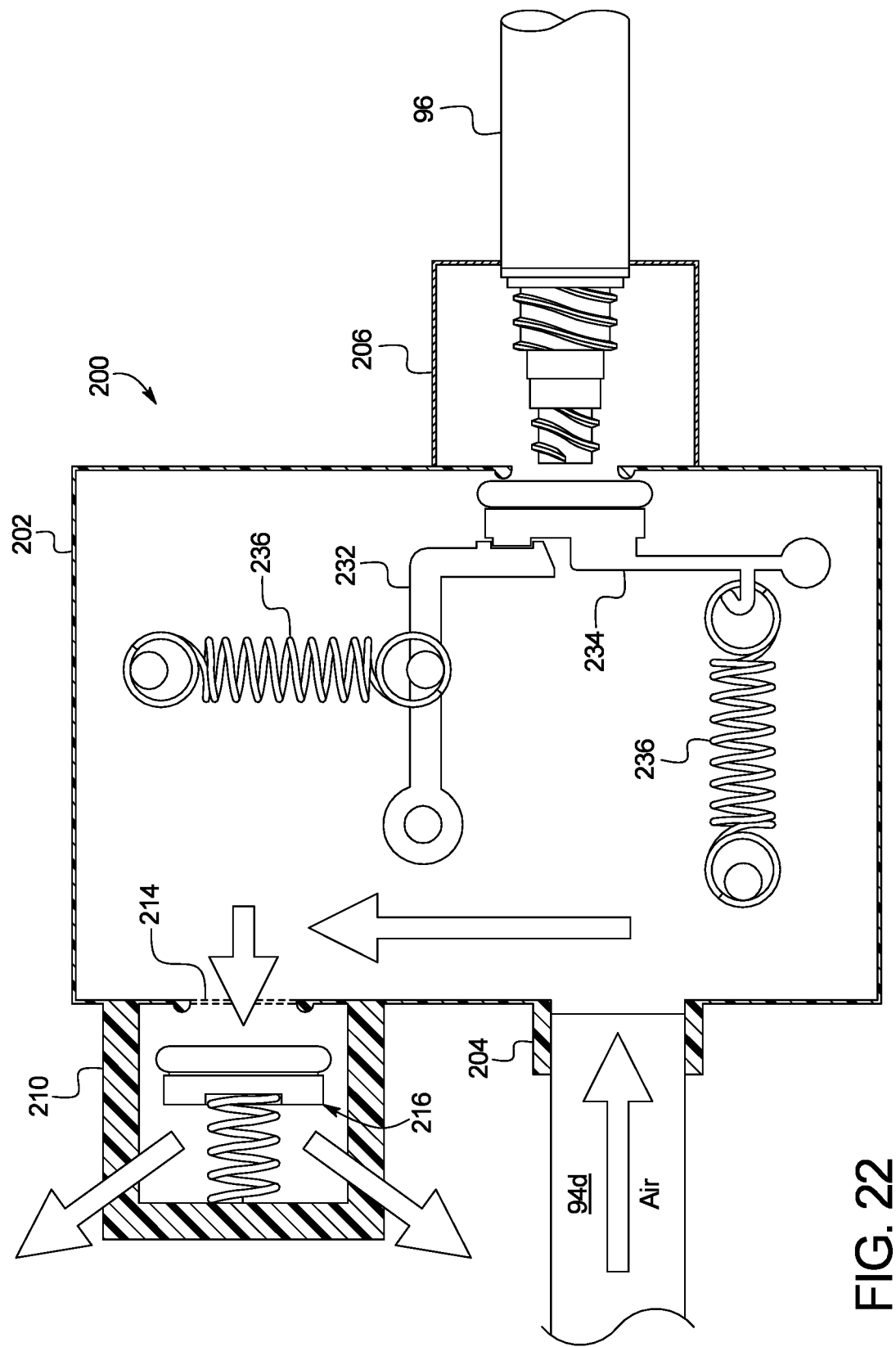
FIGS. 22 to 24 are schematic views of a third embodiment for a self-priming patient connector of the present disclosure.
Figure 23:
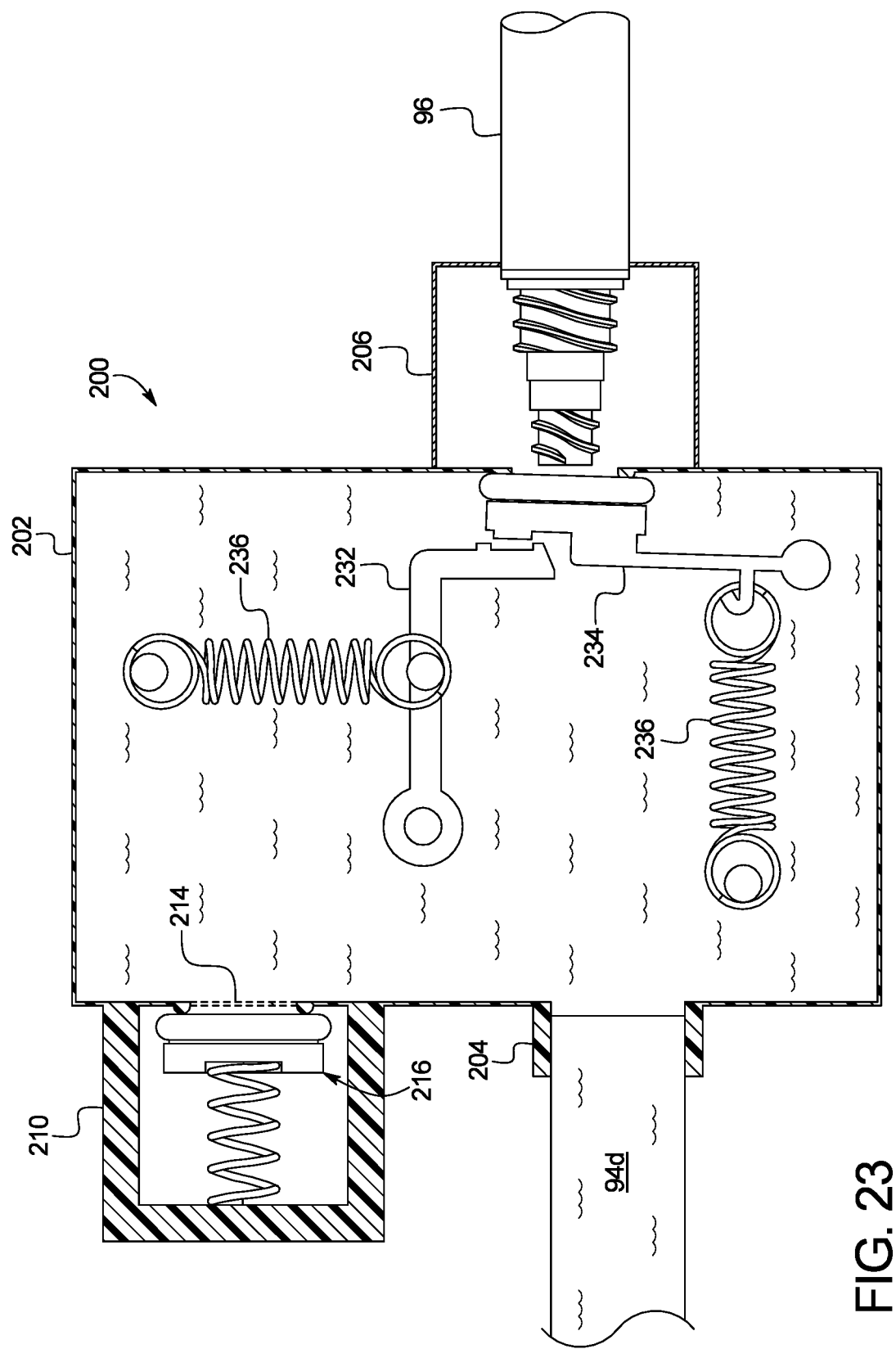
Figure 24:
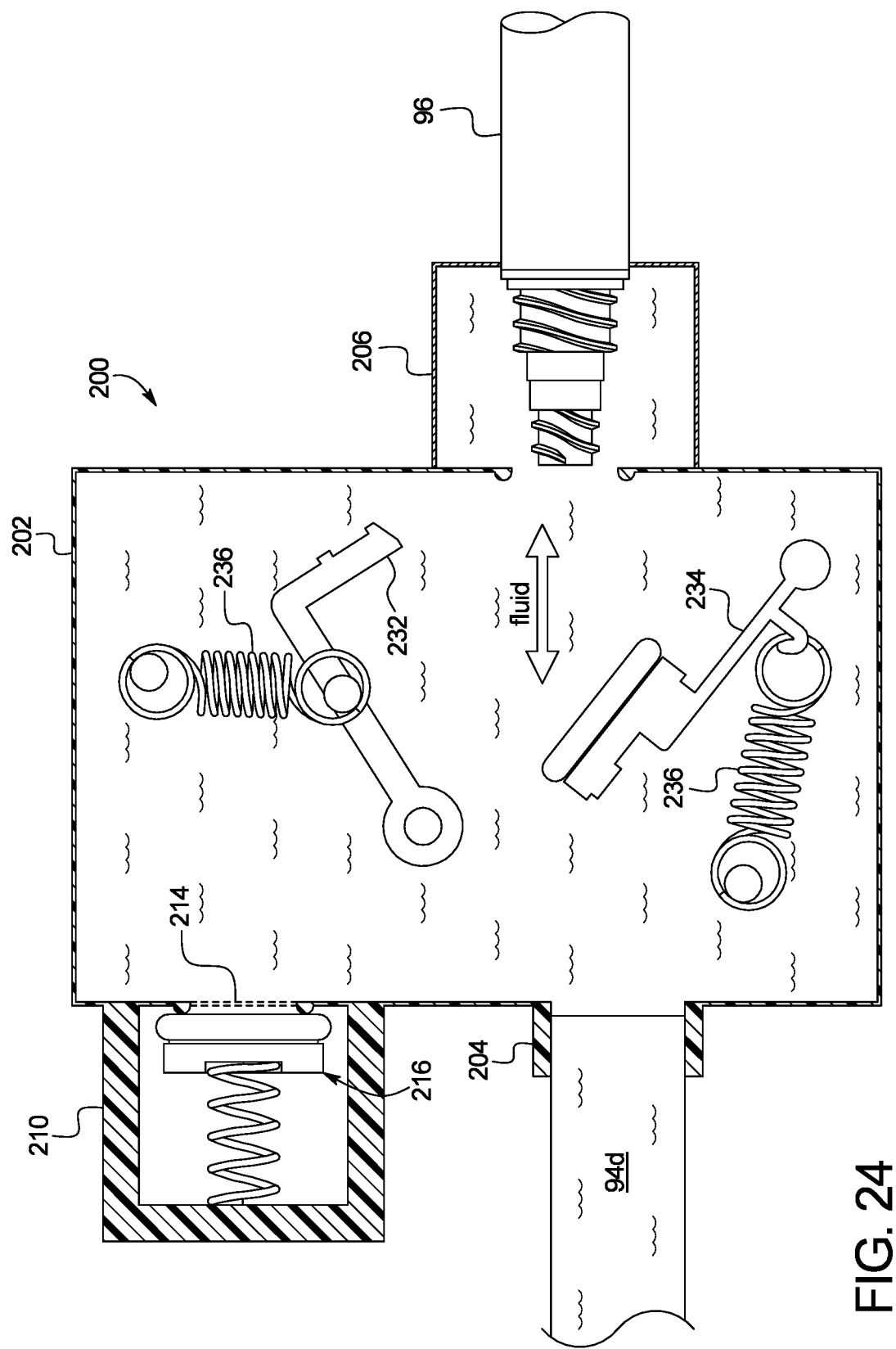

FIGS. 22 to 24 illustrate a further alternative implementation of self-priming patient connector 200 of the present disclosure, which is not used with a ruptured or cut solid seal 208 or 228. Housing 202, connector inlet 204, connector outlet 206, check valve housing 210, hydrophobic membrane 214 and check valve 216 in FIGS. 22 to 24 include all of the structure, functionality and alternatives described above. Patient connector 200 of FIGS. 22 to 24 includes first and second members 232 and 234 that are hinged to an inner wall of housing 202. Members 232 and 234 are also each spring biased, e.g., with a stainless steel or medically safe plastic spring 236, wherein springs 236 are themselves hinged to connector housing 202 and are each initially pulled apart and thus biased to close and to rotate their respective member 232 and 234 along its hinge point. Members 232 and 234 are also initially latched together as illustrated in FIG. 22 in a manner preventing the springs from rotating the first and second members. Member 234 in FIG. 22 is positioned to block dialysis fluid flow into connector outlet 206 and patient P's transfer set 96. The latching of members 232 and 234 forms a latched member 234 and a latching member 236.

In FIG. 22, air is vented through and hydrophobic membrane 214, check valve 216 and valve housing 210 to atmosphere as described above, such that all or most all air from patient line 94d may escape during priming when patient line 94d is placed under positive pressure. Air is prevented from entering the patient connector 200 and line 94d when placed under negative pressure. The pressure in patient connector 200, e.g., less than 0.5 psig, while air is being vented through hydrophobic membrane 214 is not enough to rotate latched member 234 so as to come free from latching member 232. However, in FIG. 23, when the priming fluid, e.g., fresh dialysis fluid, reaches and wets hydrophobic membrane 214, the pressure in the patient connector increases enough, e.g., to about 5 psig, to release latched member 234 from the latching member 232. FIG. 24 illustrates that after members 232 and 234 are unlatched, both members are thereafter rotated via the stretched springs 236, returning to their unbiased positions. Members 232 and 234 remain in the rotated open positions regardless of whether they are thereafter placed under positive or negative fluid pressure to allow dialysis fluid to flow in either direction through patient connector 200 and transfer set 94. As illustrated in FIGS. 22 to 24, solid seal 208 or 228 is not used.

In an alternative embodiment, springs 236 are removed and latching member 232 and latched member 234 are replaced by a bendable, e.g., plastic, latching member and a bendable, e.g., plastic, latched member. The bendable latching member is bent to place a mechanical force on the bendable latched member, bending the latched member to close connector outlet 206 in a manner illustrated in FIG. 22. The latched member may be provided with a foam or otherwise compressible sealing head that seals connector outlet 206 closed. The pressure in patient connector 200, e.g., less than 0.5 psig, while air is being vented through hydrophobic membrane 214 is not enough to compress the compressible sealing head, so that the bendable latched member does not come free from the bendable latching member. However, when the priming fluid, e.g., fresh dialysis fluid, reaches and wets hydrophobic membrane 214, the pressure in the patient connector increases enough, e.g., to about 5 psig, to compress the compressible sealing head enough to release the bendable latched member from the bendable latching member. Upon unlatching, the bendable latching member, biased to unbend and return to a straight shape, unbends and returns to its straight shape. With bendable latching member completely out of the way, bendable latched member, biased to unbend and return to a straight shape, unbends and returns to its straight shape, opening connector outlet 206 for dialysis fluid flow in either direction.

Patient connectors 200 of the present disclosure reduce the manual effort involved with priming. Connectors 200 also remove a potential source of contamination. Patient connectors 200 also eliminate or reduce spillage associated with current priming techniques. Patient P is allowed the freedom to connect to patient line 24d whenever the patient desires instead of being tied to a sequence of priming steps. Indeed, it is contemplated for system 10 that with the peritoneal dialysis app provided on patient P's smartphone 98, patient P may load set 90 onto the machine of system 10, make sure enough tap water is present in tank 14 of distillation unit 12, connect patient line 94d to patient connector 200, and then lie in bed and begin treatment using the peritoneal dialysis app.

Dialysis Fluid Regeneration

Referring again to FIG. 1, it is contemplated for system 10 to regenerate and reuse used dialysis fluid removed from patient P. In the version of system 10 in FIG. 1, after a patient dwell, control unit 24 causes valves 84d and 84b to be open and with all other valves closed, run pump actuator 82 in a reverse direction to pull used dialysis fluid from patient P, through patient transfer set 96, patient connector 200, patient line 94d, pumping and heating line 92, and inlet/outlet line 94b into mixing bag 100. When patient P is fully drained, control unit 24 causes dialysis fluid volume control subsystem 150 to determine the volume of the patient drain, which is stored to later determine an overall amount of ultrafiltration removed for the treatment.

After the drain volume measurement, control unit 24 causes valves 84b and 84e to be open and with all other valves closed, run pump actuator 82 in a forward direction to pull used dialysis fluid from mixing bag 100, through inlet/outlet line 94c, and return line 94e to tank 14 of distillation unit 12. Once inside distillation unit 12, the patient effluent is boiled and condensed into purified water, e.g., WFI, which is sent to mixing bag 100 for mixing with one or more concentrate capsule 110 to form a prescribed formulation of peritoneal dialysis fluid as has been described herein. The above cycle is repeated as many times as prescribed, and wherein a final patient fill may be left within patient P as a last fill, removed to tank 14 of distillation unit 12, or delivered to drain 76.

Figure 25:
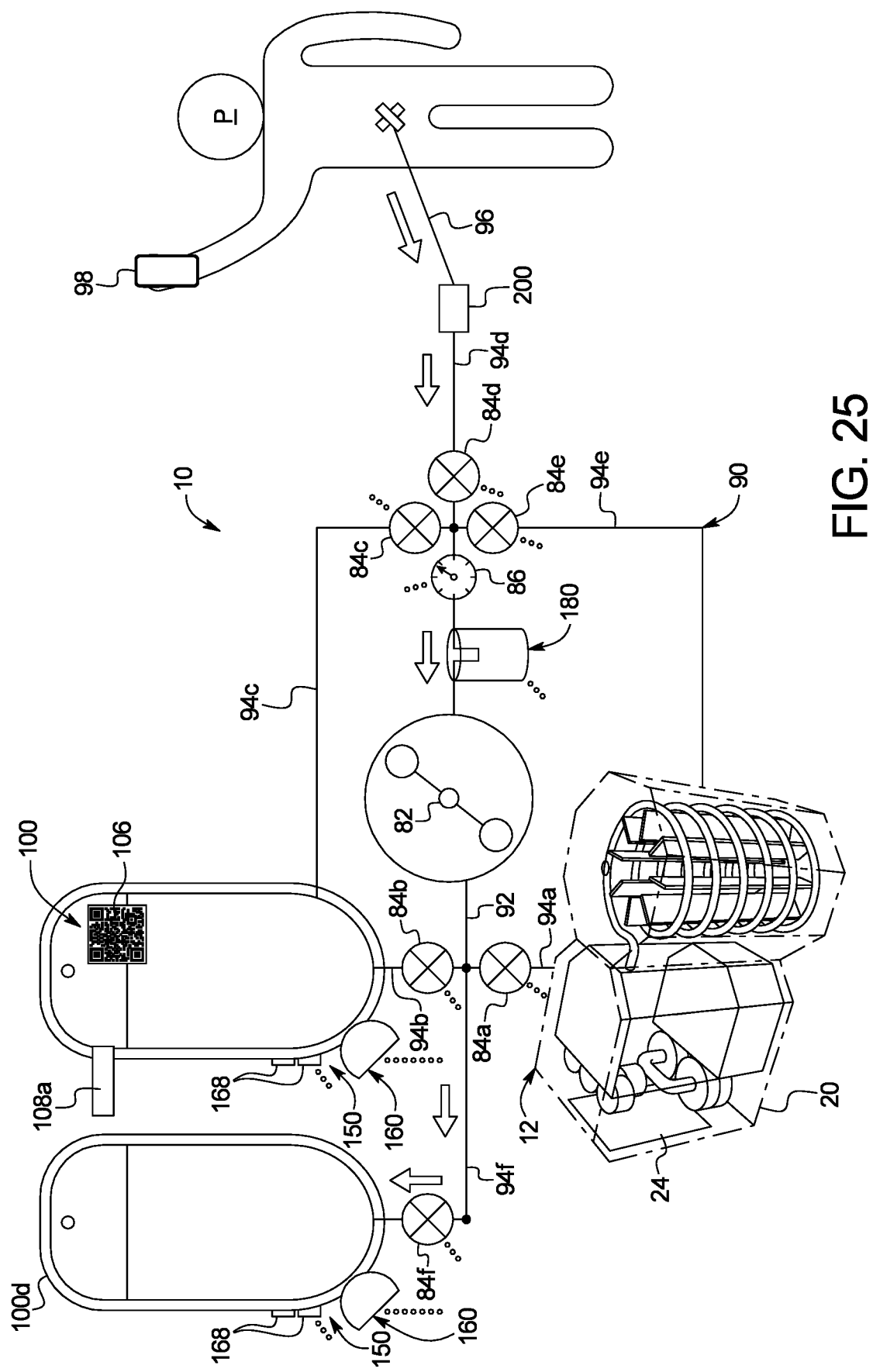
FIG. 25 is a perspective view of a first alternative embodiment of an online and regenerative dialysis system of the present disclosure, which includes a dedicated drain container or bag.

Referring now to FIG. 25, in an alternative regeneration and reuse embodiment, system 10 is modified so as to have a dedicated drain container or bag 100*d*, which is placed in fluid communication with pumping and heating line 92 via a drain container line 94*f*, which is selectively opened and closed by a valve 84*f*, such as a normally closed solenoid pinch valve under control of control unit 24. Here, drain bag 100*d* operates with its own dialysis fluid volume control subsystem 150 having pressure sensor 160 and one or more level sensor 168, each outputting to control unit 24. Mixing bag 100 becomes a dedicated fresh dialysis fluid bag.

In the version of system 10 in FIG. 25, during a patient dwell under control of control unit 24, distillation unit 12 prepares a next batch of purified water, e.g., WFI, which is delivered via any of the fluid pathways described herein to mixing bag 100. The WFI is mixed with at least one concentrate capsule 110 and heated in the recirculation loop as described herein to form fresh dialysis fluid at close to patient temperature, which is stored in mixing bag 100 until the patient dwell is complete. Patient dwells may last on the order of two hours, which provides adequate time to distill and condense the WFI and mix and heat one to 2.5 liters of fresh dialysis fluid, a typical patient fill range.

After the patient dwell, control unit 24 causes valves 84*d* and 84*f* to be open and with all other valves closed, run pump actuator 82 in a reverse direction to pull used dialysis fluid from patient P, through patient transfer set 96, patient connector 200, patient line 94*d*, pumping and heating line 92, and drain container line 94*f* into drain bag 100*d*. When patient P is fully drained, control unit 24 causes dialysis fluid volume control subsystem 150 operating with drain bag 100*d* to determine the volume of the patient drain, which is stored at control unit 24 to later determine an overall amount of ultrafiltration removed for the treatment.

When patient P is fully drained, control unit 24 also causes valves 84*b* and 84*d* to be open and with all other valves closed, run pump actuator 82 in a forward direction to push a next prescribed fill volume's worth of fresh dialysis fluid through inlet/outlet line 94*b*, pumping and heating line 92 where inline heater 180 heats the fresh dialysis fluid to patient temperature, through patient line 94*d*, self-priming connector 200 and transfer set 96, to patient P to begin a next dwell period. Dialysis fluid volume control subsystem 150 operating with mixing bag 100 determines the volume of the subsequent patient fill, which is stored in control unit 24 to show that the prescribed treatment has been followed and to later determine an overall amount of ultrafiltration removed for the treatment. System 10 in FIG. 25 accordingly wastes virtually no time between when patient P is fully drained of effluent and when the patient begins to receive the next fill.

After the drain volume measurement at drain bag 100*d*, control unit 24 causes valves 84*f* and 84*e* to be open and with all other valves closed, run pump actuator 82 in a forward direction to pull used dialysis fluid from drain bag 100*d*, through drain container line 94*f*, and return line 94*e* to tank 14 of distillation unit 12. Once inside distillation unit 12, the patient effluent is boiled and condensed into purified water, e.g., WFI, which is sent to now empty mixing bag 100 for mixing with one or more concentrate capsule 110 to form a prescribed formulation of peritoneal dialysis fluid as has been described herein. The above cycle is repeated as many times as prescribed, wherein a final patient fill may be left within patient P as a last fill, removed to tank 14 of distillation unit 12, or delivered to drain 76.

The regeneration of used dialysis fluid has a number of advantages compared to sending all used dialysis fluid to the drain bag 100*d*. For instance, regeneration reduces the amount of total water consumed, and may eliminate the need for an online water source. This enables therapy water to be independent from (or minimally dependent on) external water sources. This also reduces the amount of disposables and consumables used such that consumables are only primarily used for the concentrates. Further, regeneration is safe for a patient because source water from a peritoneal cavity is by definition safe to put back into the patient since it was already there. Additionally, effluent does not have to be cleaned to a high degree to provide effective therapy (e.g. 95% effective cleaning will result in about 5% longer therapy to reach the same dialysis adequacy Kt/V (clearance*time/body water volume)). Moreover, waste can be concentrated to minimize disposal frequency (e.g., ~2.1 kilograms/week).

Figure 26:
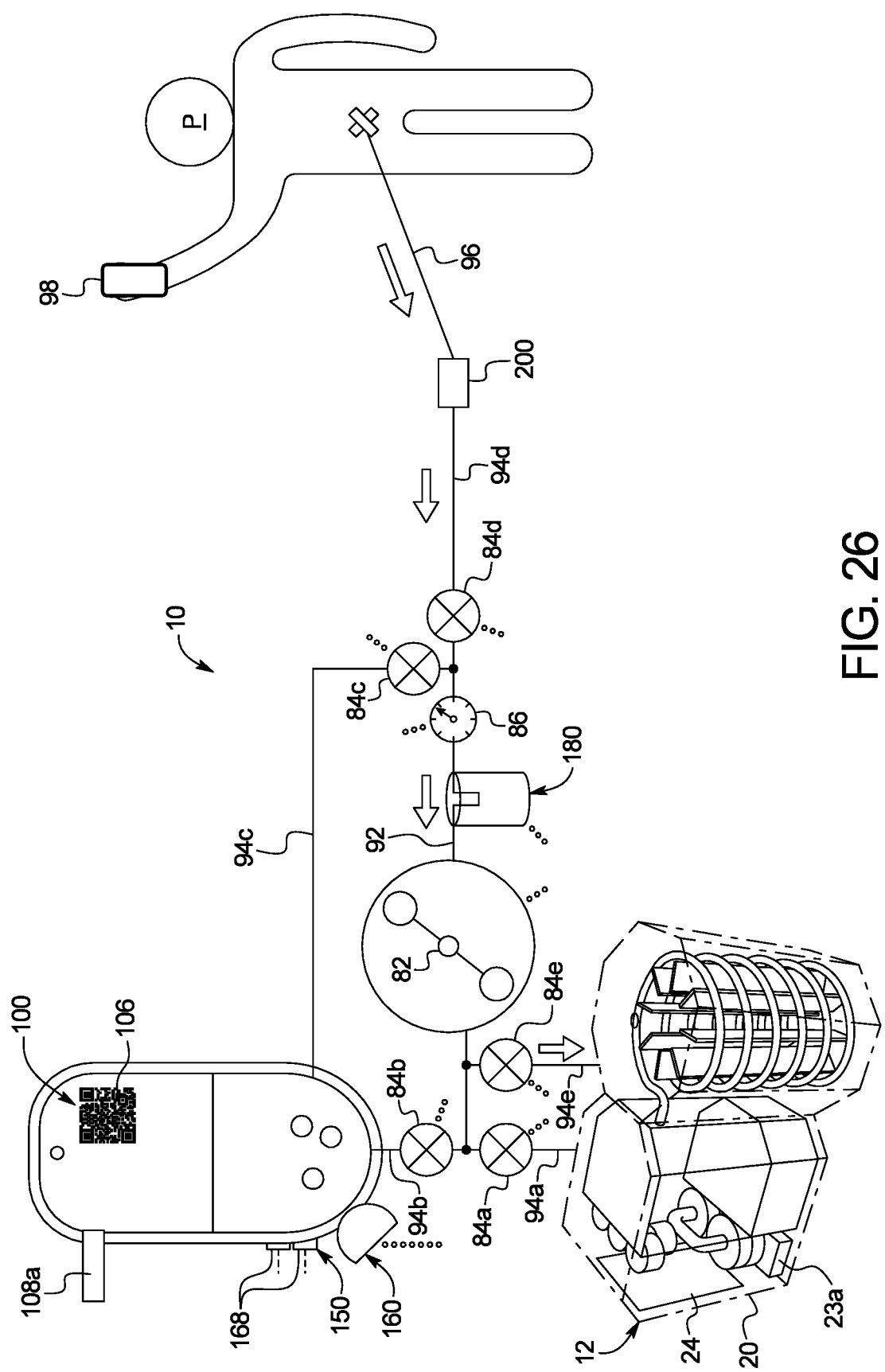
FIG. 26 is a perspective view of a second alternative embodiment of an online and regenerative dialysis system of the present disclosure, which includes an alternative structure for determining an amount of a patient drain.

Referring now to FIG. 26, in another alternative regeneration and reuse embodiment, system 10 is modified so as to be able to pump effluent fluid from patient P directly to tank 14 of distillation unit 12. To do so, return valve 84*e* and return line 94*e* are moved to the other side of pump actuator 82 along pumping and valving line 92. The move allows control unit 24 to cause pump actuator 82 to pump effluent directly from patient P to tank 14. It should be appreciated that the move of return valve 84*e* and return line 94*e* to the other side of pump actuator 82 could also be made for system 10 in FIGS. 1 and 25 if desired. Another modification is the addition of a structure for determining the volume or amount of effluent removed from patient P, which is located somewhere along patient line 94*d*, pumping and valving line 92, return line 94*e*, and/or within distillation unit. For example, one or more flowmeter (not illustrated) outputting to control unit 24 may be located so as to operate with any of patient line 94*d*, pumping and valving line 92, return line 94*e*, wherein the control unit integrates the flowrate signal over the course of the drain to determine total drain volume.

Another option is to place a weigh scale 230 within housing 20 in a manner so as to weigh the contents within storage tank 14 of distillation unit 12. Weigh scale 230 may for example be placed beneath storage tank 14. Or, storage tank 14 may hang from weigh scale 230. Weigh scale 230 weighs the difference in weight of fluid contained within storage tank 14 before and after the patient drain and therefore does not have to be empty at the beginning of the drain. Weigh scale 230 outputs an effluent weight signal to control unit 24, which converts the weight to a volume knowing the density of the effluent, so that the drain volume may be used in the overall ultrafiltration volume calculation. It should be appreciated that weigh scale 230 is useful for reasons other than determining drain volume. Weigh scale 230 may also be used with control unit 24 and user interface 26 (and/or smartphone 98) to inform patient P how much tap water needs to be added to tank 14 at the beginning of treatment, e.g., so that there is enough fluid within storage tank 14 to prepare a first batch of purified water, e.g., WFI, for a first patient fill, and a second batch of purified water, e.g., WFI, for a second patient fill while waiting for a first patient dwell to be completed.

In the version of system 10 in FIG. 26, during a patient dwell under control of control unit 24, distillation unit 12 prepares a next batch of purified water, e.g., WFI, which is delivered via any of the fluid pathways described herein to mixing bag 100. The WFI is mixed with at least one concentrate capsule 110 and heated in the recirculation loop as described herein to form fresh dialysis fluid at close to patient temperature, which is stored in mixing bag 100 until the patient dwell is complete.

After the patient dwell, control unit 24 causes valves 84*d* and 84*e* to be open and with all other valves closed, run pump actuator 82 in a reverse direction to pull used dialysis fluid from patient P, through patient transfer set 96, patient connector 200, patient line 94*d*, pumping and heating line 92, and return line 94*e* into storage container 14 of distillation unit 12. Control unit 24 in one embodiment uses one or more flowmeter (not illustrated) operating with any of patient line 94*d*, pumping and valving line 92, and/or return line 94*e* to integrate the drain volume over the course of the patient drain, which is stored at control unit 24 to later determine an overall amount of ultrafiltration removed for the treatment. In another embodiment, after patient P is fully drained, control unit 24 receives a weight difference signal from weigh scale 230 (difference in weight before and after the patient drain) and uses the drain weight to determine drain volume, which is stored at control unit 24 to later determine an overall amount of ultrafiltration removed for the treatment.

When patient P is fully drained, control unit 24 also causes valves 84*b* and 84*d* to be open and with all other valves closed, run pump actuator 82 in a forward direction to push a next prescribed fill volume's worth of fresh dialysis fluid through inlet/outlet line 94*b*, pumping and heating line 92 where inline heater 180 heats the fresh dialysis fluid to patient temperature, through patient line 94*d*, self-priming connector 200 and transfer set 96, to patient P to begin a next dwell period. Dialysis fluid volume control subsystem 150 operating with mixing bag 100 determines the volume of the subsequent patient fill, which is stored in control unit 24 to show that the prescribed treatment has been followed and to later determine an overall amount of ultrafiltration removed for the treatment. System 10 in FIG. 26 also wastes virtually no time between when patient P is fully drained of effluent and when the patient begins to receive the next fill.

Once inside distillation unit 12, the patient effluent is boiled and condensed into purified water, e.g., WFI, which is sent to now empty mixing bag 100 for mixing with one or more concentrate capsule 110 to form a prescribed formulation of peritoneal dialysis fluid as has been described herein. The above cycle is repeated as many times as prescribed, wherein a final patient fill may be left within patient P as a last fill, removed to tank 14 of distillation unit 12, or delivered to drain 76.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, while pump actuator 82 is described as being a peristaltic pump actuator, pump actuator 82 may alternatively be a volumetric pump actuator, membrane pump actuator, platen pump actuator, or other type of pump actuator.

The invention is claimed as follows:

1. A patient connector for dialysis comprising:
   a cylindrical housing including an inlet and an outlet and defining at least one aperture;
   a seal initially blocking the outlet;
   a cylindrical hydrophobic filter covering the at least one aperture along an inner wall of the cylindrical housing, the cylindrical hydrophobic filter located coaxially within the cylindrical housing so as to cover the at least one aperture along the inner wall of the cylindrical housing; and
   a check valve positioned and arranged to prevent air from being vented from the cylindrical housing via the at least one aperture and through the cylindrical hydrophobic filter when the cylindrical housing is under atmospheric pressure or negative pressure, the check valve configured to allow air to be vented from the cylindrical housing via the at least one aperture and through the cylindrical hydrophobic filter when the cylindrical housing is under positive pressure,
   wherein the check valve includes an elastomeric sleeve that press-fits over the cylindrical housing so as to cover the at least one aperture, the elastomeric sleeve expanding under positive pressure to allow air to be vented from the cylindrical housing through the cylindrical hydrophobic filter and the at least one aperture.

2. The patient connector of claim 1, wherein the cylindrical housing defines a plurality of apertures and the elastomeric sleeve is cylindrical and sized to cover each of the plurality of apertures.

3. The patient connector of claim 1, wherein the cylindrical hydrophobic filter is configured to allow air under positive pressure from a patient line connected to the patient connector to be vented through the at least one aperture and to disallow a liquid from escaping through the at least one aperture after the liquid has traveled through the patient line to reach the patient connector.

4. The patient connector of claim 3, wherein the seal initially blocking the outlet is configured to rupture under pressure from the liquid after reaching the patient connector and building pressure against the seal.

5. The patient connector of claim 3, further comprising a cutting member located within the cylindrical housing so as to be moved by the liquid reaching the patient connector to open the seal.

6. The patient connector of claim 3, further comprising a cylindrical spike translated by the liquid reaching the patient connector to pierce the seal.

\* \* \* \* \*